United States Patent
Kunz et al.

(10) Patent No.: US 12,304,958 B2
(45) Date of Patent: May 20, 2025

(54) ANTIBODIES TARGETING ACTRIIA AND ACTRIIB

(71) Applicant: SixPeaks Bio AG, Basel (CH)

(72) Inventors: Christian Kunz, Basel (CH); Amélie Wiederkehr, Ranspach le bas (FR); Lisa Wellinger, Basel (CH); Anne Laure Lainé, Huningue (FR); Emily Radke, West Lebanon, NH (US); Caitlin Stein, Clarkston, MI (US); Arvind Sivasubramanian, Santa Clara, CA (US)

(73) Assignee: Six Peaks Bio AG, Basel (CH)

( * ) Notice: Subject to any disclaimer, the term of this patent is extended or adjusted under 35 U.S.C. 154(b) by 0 days.

(21) Appl. No.: 18/945,784

(22) Filed: Nov. 13, 2024

(65) Prior Publication Data

US 2025/0109208 A1 Apr. 3, 2025

Related U.S. Application Data

(63) Continuation of application No. 18/898,854, filed on Sep. 27, 2024, now abandoned.

(30) Foreign Application Priority Data

Sep. 28, 2023 (EP) .................................... 23200478

(51) Int. Cl.
*C07K 16/28* (2006.01)

(52) U.S. Cl.
CPC ...... *C07K 16/2863* (2013.01); *C07K 2317/33* (2013.01); *C07K 2317/52* (2013.01); *C07K 2317/565* (2013.01)

(58) Field of Classification Search
None
See application file for complete search history.

(56) References Cited

U.S. PATENT DOCUMENTS

| 2016/0031993 A1* | 2/2016 | Berger | A61P 21/04 |
| | | | 435/69.6 |
| 2018/0230221 A1* | 8/2018 | Tanko | A61P 17/02 |

FOREIGN PATENT DOCUMENTS

WO 2010/125003 11/2010

OTHER PUBLICATIONS

Bogdanovich et al., "Functional Improvement of Dystrophic Muscle by Myostatin Blockage" Nature 2002 420: 418-421.
Bradley et al., "Myostatin as a Therapeutic Target for Musculoskeletal Disease" Cell. Mol. Life Sci. 2008 65:2119-2124.
Morvan et al., "Blockade of Activin Type II Receptors with a Dual Anti-ActRIIA/IIB Antibody is Critical to Promote Maximal Skeletal Muscle Hypertrophy" Proc. Natl Acad. Sci. USA 2017 114:12448-12453.

* cited by examiner

*Primary Examiner* — Phuong Huynh
(74) *Attorney, Agent, or Firm* — Licata & Tyrrell P.C.

(57) ABSTRACT

The present disclosure relates to antibodies and antibody fragments that are specific for ActRIIA and ActRIIB. The antibodies are improved versions of bimagrumab. Antibodies of the present invention have an improved affinity against ActRIIA, translating into improved in vitro potency and efficacy, an improved PK and PD profile and a higher stability making the antibodies suitable for s.c. administration. Optionally they carry Fc modifications making the antibodies safe for prolonged treatments.

14 Claims, 14 Drawing Sheets
Specification includes a Sequence Listing.

SEQUENCE LISTING

```
Sequence total quantity: 80
SEQ ID NO: 1             moltype = AA  length = 513
FEATURE                  Location/Qualifiers
source                   1..513
                         mol_type = protein
                         organism = Homo sapiens
SEQUENCE: 1
MGAAAKLAFA VFLISCSSGA ILGRSETQEC LFFNANWEKD RTNQTGVEPC YGDKDKRRHC   60
FATWKNISGS IEIVKQGCWL DDINCYDRTD CVEKKDSPEV YFCCCEGNMC NEKFSYFPEM  120
EVTQPTSNPV TPKPPYYNIL LYSLVPLMLI AGIVICAFWV YRHHKMAYPP VLVPTQDPGP  180
PPPSPLLGLK PLQLLEVKAR GRFGCVWKAQ LLNEYVAVKI FPIQDKQSWQ NEYEVYSLPG  240
MKHENILQFI GAEKRGTSVD VDLWLITAFH EKGSLSDFLK ANVVSWNELC HIAETMARGL  300
AYLHEDIPGL KDGHKPAISH RDIKSKNVLL KNNLTACIAD FGLALKFEAG KSAGDTHGQV  360
GTRRYMAPEV LEGAINFQRD AFLRIDMYAM GLVLWELASR CTAADGPVDE YMLPFEEEIG  420
```

```
QHPSLEDMQE VVVHKKKRPV LRDYWQKHAG MAMLCETIEE CWDHDAEARL SAGCVGERIT    480
QMQRLTNIIT TEDIVTVVTM VTNVDFPPKE SSL                                513

SEQ ID NO: 2           moltype = AA  length = 512
FEATURE                Location/Qualifiers
source                 1..512
                       mol_type = protein
                       organism = Homo sapiens
SEQUENCE: 2
MTAPWVALAL LWGSLCAGSG RGEAETRECI YYNANWELER TNQSGLERCE GEQDKRLHCY    60
ASWRNSSGTI ELVKKGCWLD DFNCYDRQEC VATEENPQVY FCCCEGNFCN ERFTHLPEAG    120
GPEVTYEPPP TAPTLLTVLA YSLLPIGGLS LIVLLAFWMY RHRKPPYGHV DIHEDPGPPP    180
PSPLVGLKPL QLLEIKARGR FGCVWKAQLM NDFVAVKIFP LQDKQSWQSE REIFSTPGMK    240
HENLLQFIAA EKRGSNLEVE LWLITAFHDK GSLTDYLKGN IITWNELCHV AETMSRGLSY    300
LHEDVPWCRG EGHKPSIAHR DFKSKNVLLK SDLTAVLADF GLAVRFEPGK PPGDTHGQVG    360
TRRYMAPEVL EGAINFQRDA FLRIDMYAMG LVLWELVSRC KAADGPVDEY MLPFEEEIGQ    420
HPSLEELQEV VVHKKMRPTI KDHWLKHPGL AQLCVTIEEC WDHDAEARLS AGCVEERVSL    480
IRRSVNGTTS DCLVSLVTSV TNVDLPPKES SI                                 512

SEQ ID NO: 3           moltype = AA  length = 5
FEATURE                Location/Qualifiers
source                 1..5
                       mol_type = protein
                       organism = synthetic construct
SEQUENCE: 3
SSYIN                                                               5

SEQ ID NO: 4           moltype = AA  length = 17
FEATURE                Location/Qualifiers
source                 1..17
                       mol_type = protein
                       organism = synthetic construct
SEQUENCE: 4
TINPVSGSTS YAQKFQG                                                  17

SEQ ID NO: 5           moltype = AA  length = 6
FEATURE                Location/Qualifiers
source                 1..6
                       mol_type = protein
                       organism = synthetic construct
SEQUENCE: 5
GGWFDY                                                              6

SEQ ID NO: 6           moltype = AA  length = 14
FEATURE                Location/Qualifiers
source                 1..14
                       mol_type = protein
                       organism = synthetic construct
SEQUENCE: 6
TGTSSDVGSY NYVN                                                     14

SEQ ID NO: 7           moltype = AA  length = 7
FEATURE                Location/Qualifiers
source                 1..7
                       mol_type = protein
                       organism = synthetic construct
SEQUENCE: 7
GVSKRPS                                                             7

SEQ ID NO: 8           moltype = AA  length = 11
FEATURE                Location/Qualifiers
source                 1..11
                       mol_type = protein
                       organism = synthetic construct
SEQUENCE: 8
GTFAGGSYYG V                                                        11

SEQ ID NO: 9           moltype = AA  length = 115
FEATURE                Location/Qualifiers
source                 1..115
                       mol_type = protein
                       organism = synthetic construct
SEQUENCE: 9
QVQLVQSGAE VKKPGASVKV SCKASGYTFT SSYINWVRQA PGQGLEWMGT INPVSGSTSY    60
AQKFQGRVTM TRDTSISTAY MELSRLRSDD TAVYYCARGG WFDYWGQGTL VTVSS         115

SEQ ID NO: 10          moltype = AA  length = 111
FEATURE                Location/Qualifiers
source                 1..111
```

```
SEQ ID NO: 10                 moltype = AA   length = 111
FEATURE                       Location/Qualifiers
source                        1..111
                              mol_type = protein
                              organism = synthetic construct
SEQUENCE: 10
QSALTQPASV SGSPGQSITI SCTGTSSDVG SYNYVNWYQQ HPGKAPKLMI YGVSKRPSGV    60
SNRFSGSKSG NTASLTISGL QAEDEADYYC GTFAGGSYYV VFGGGTKLTV L            111

SEQ ID NO: 11                 moltype = AA   length = 17
FEATURE                       Location/Qualifiers
source                        1..17
                              mol_type = protein
                              organism = synthetic construct
SEQUENCE: 11
TINAVSGSTS YAQKFQG                                                   17

SEQ ID NO: 12                 moltype = AA   length = 115
FEATURE                       Location/Qualifiers
source                        1..115
                              mol_type = protein
                              organism = synthetic construct
SEQUENCE: 12
QVQLVQSGAE VKKPGSSVKV SCKASGYTFT SSYINWVRQA PGQGLEWMGT INAVSGSTSY    60
AQKFQGRVTI TADESTSTAY MELSSLRSED TAVYYCARGG WFDYWGQGTL VTVSS         115

SEQ ID NO: 13                 moltype = AA   length = 7
FEATURE                       Location/Qualifiers
source                        1..7
                              mol_type = protein
                              organism = synthetic construct
SEQUENCE: 13
GVSKRES                                                              7

SEQ ID NO: 14                 moltype = AA   length = 11
FEATURE                       Location/Qualifiers
source                        1..11
                              mol_type = protein
                              organism = synthetic construct
SEQUENCE: 14
GTFAGGKYYG V                                                         11

SEQ ID NO: 15                 moltype = AA   length = 111
FEATURE                       Location/Qualifiers
source                        1..111
                              mol_type = protein
                              organism = synthetic construct
SEQUENCE: 15
QSALTQPRSV SGSPGQSVTI SCTGTSSDVG SYNYVNWYQQ HPGKAPKLMI YGVSKRESGV    60
PDRFSGSKSG NTASLTISGL QAEDEADYYC GTFAGGKYYG VFGGGTKLTV L            111

SEQ ID NO: 16                 moltype = AA   length = 115
FEATURE                       Location/Qualifiers
source                        1..115
                              mol_type = protein
                              organism = synthetic construct
SEQUENCE: 16
QVQLVQSGAE VKKPGSSVKV SCKASGYTFT SSYINWVRQA PGQGLEWMGT INAVSGSTSY    60
AQKFQGRVTI TADTSTSTAY MELSSLRSED TAVYYCARGG WFDYWGQGTL VTVSS         115

SEQ ID NO: 17                 moltype = AA   length = 14
FEATURE                       Location/Qualifiers
source                        1..14
                              mol_type = protein
                              organism = synthetic construct
SEQUENCE: 17
TGTSSDVGSF NYVN                                                      14

SEQ ID NO: 18                 moltype = AA   length = 11
FEATURE                       Location/Qualifiers
source                        1..11
                              mol_type = protein
                              organism = synthetic construct
SEQUENCE: 18
GTFAGGAYYG V                                                         11

SEQ ID NO: 19                 moltype = AA   length = 111
FEATURE                       Location/Qualifiers
source                        1..111
                              mol_type = protein
                              organism = synthetic construct
SEQUENCE: 19
```

```
QSALTQPRSV SGSPGQSVTI SCTGTSSDVG SFNYVNWYQQ HPGKAPKLMI RGVSKRESGV    60
PDRFSGSKSG NTASLTISGL QAEDEADYYC GTFAGGAYYG VFGGGTKLTV L             111

SEQ ID NO: 20           moltype = AA   length = 11
FEATURE                 Location/Qualifiers
source                  1..11
                        mol_type = protein
                        organism = synthetic construct
SEQUENCE: 20
GTFAGGKYYG V                                                         11

SEQ ID NO: 21           moltype = AA   length = 111
FEATURE                 Location/Qualifiers
source                  1..111
                        mol_type = protein
                        organism = synthetic construct
SEQUENCE: 21
QSALTQPRSV SGSPGQSVTI SCTGTSSDVG SYNYVNWYQQ HPGKAPKLMI YGVSKRDSGV    60
PDRFSGSKSG NTASLTISGL QAEDEADYYC GTFAGGKYYG VFGGGTKLTV L             111

SEQ ID NO: 22           moltype = AA   length = 14
FEATURE                 Location/Qualifiers
source                  1..14
                        mol_type = protein
                        organism = synthetic construct
SEQUENCE: 22
TGTSSDVGSK NYVN                                                      14

SEQ ID NO: 23           moltype = AA   length = 111
FEATURE                 Location/Qualifiers
source                  1..111
                        mol_type = protein
                        organism = synthetic construct
SEQUENCE: 23
QSALTQPRSV SGSPGQSVTI SCTGTSSDVG SKNYVNWYQQ HPGKAPKLMI YGVSKRESGV    60
PDRFSGSKSG NTASLTISGL QAEDEADYYC GTFAGGKYYG VFGGGTKLTV L             111

SEQ ID NO: 24           moltype = AA   length = 115
FEATURE                 Location/Qualifiers
source                  1..115
                        mol_type = protein
                        organism = synthetic construct
SEQUENCE: 24
QVQLVQSGAE VKKPGSSVKV SCKASGYTFT SSYINWVRQA PGQGLEWMGT INPVSGSTSY    60
AQKFQGRVTI TADTSTSTAY MELSSLRSED TAVYYCARGG WFDYWGQGTL VTVSS         115

SEQ ID NO: 25           moltype = AA   length = 111
FEATURE                 Location/Qualifiers
source                  1..111
                        mol_type = protein
                        organism = synthetic construct
SEQUENCE: 25
QSALTQPRSV SGSPGQSVTI SCTGTSSDVG SYNYVNWYQQ HPGKAPKLMI YGVSKRESGV    60
PDRFSGSKSG NTASLTISGL QAEDEADYYC GTFAGGAYYG VFGGGTKLTV L             111

SEQ ID NO: 26           moltype = AA   length = 14
FEATURE                 Location/Qualifiers
source                  1..14
                        mol_type = protein
                        organism = synthetic construct
SEQUENCE: 26
TGTSSDVGSR NYVN                                                      14

SEQ ID NO: 27           moltype = AA   length = 11
FEATURE                 Location/Qualifiers
source                  1..11
                        mol_type = protein
                        organism = synthetic construct
SEQUENCE: 27
GTFAGGDYYG V                                                         11

SEQ ID NO: 28           moltype = AA   length = 111
FEATURE                 Location/Qualifiers
source                  1..111
                        mol_type = protein
                        organism = synthetic construct
SEQUENCE: 28
QSALTQPRSV SGSPGQSVTI SCTGTSSDVG SRNYVNWYQQ HPGKAPKLMI YGVSKRESGV    60
PDRFSGSKSG NTASLTISGL QAEDEADYYC GTFAGGDYYG VFGGGTKLTV L             111
```

```
SEQ ID NO: 29          moltype = AA    length = 14
FEATURE                Location/Qualifiers
source                 1..14
                       mol_type = protein
                       organism = synthetic construct
SEQUENCE: 29
TGTSSDVGSA NYVN                                                     14

SEQ ID NO: 30          moltype = AA    length = 7
FEATURE                Location/Qualifiers
source                 1..7
                       mol_type = protein
                       organism = synthetic construct
SEQUENCE: 30
GVSRRPS                                                              7

SEQ ID NO: 31          moltype = AA    length = 111
FEATURE                Location/Qualifiers
source                 1..111
                       mol_type = protein
                       organism = synthetic construct
SEQUENCE: 31
QSALTQPRSV SGSPGQSVTI SCTGTSSDVG SANYVNWYQQ HPGKAPKPMI YGVSRRPSGV    60
PDRFSGSKSG NTASLTISGL QAEDEADYYC GTFAGGKYYG VFGGGTKLTV L            111

SEQ ID NO: 32          moltype = AA    length = 115
FEATURE                Location/Qualifiers
source                 1..115
                       mol_type = protein
                       organism = synthetic construct
SEQUENCE: 32
QVQLVQSGAE VRKPGSSVKV SCKASGYTFT SSYINWVRQA PGQGLEWMGT INPVSGSTSY    60
AQKFQGRVTI TADTSTSTAY MELSSLRSED TAVYYCARGG WFDYWGQGTL VTVSS        115

SEQ ID NO: 33          moltype = AA    length = 14
FEATURE                Location/Qualifiers
source                 1..14
                       mol_type = protein
                       organism = synthetic construct
SEQUENCE: 33
TGTSSDVGSY NRVN                                                     14

SEQ ID NO: 34          moltype = AA    length = 11
FEATURE                Location/Qualifiers
source                 1..11
                       mol_type = protein
                       organism = synthetic construct
SEQUENCE: 34
GTFAGGRYYG V                                                        11

SEQ ID NO: 35          moltype = AA    length = 111
FEATURE                Location/Qualifiers
source                 1..111
                       mol_type = protein
                       organism = synthetic construct
SEQUENCE: 35
QSALTQPRSV SGSPGQSVTI SCTGTSSDVG SYNRVNWYQQ HPGKAPKLMI YGVSKRESGV    60
PDRFSGSKSG NTASLTISGL QAEDEADYYC GTFAGGRYYG VFGGGTKLTV L            111

SEQ ID NO: 36          moltype = AA    length = 115
FEATURE                Location/Qualifiers
source                 1..115
                       mol_type = protein
                       organism = synthetic construct
SEQUENCE: 36
QVQLVQSGAE VKKPGSSVKV SCKASGYKFT SSYINWVRQA PGQGLEWMGT INAVSGSTSY    60
AQKFQGRVTI TADESTSTAY MELSSLRSED TAVYYCARGG WFDYWGQGTL VTVSS        115

SEQ ID NO: 37          moltype = AA    length = 115
FEATURE                Location/Qualifiers
source                 1..115
                       mol_type = protein
                       organism = synthetic construct
SEQUENCE: 37
QVQLVQSGAE VKKPGSSVKV SCKASGYKFT SSYINWVRQA PGQGLEWMGT INAVSGSTSY    60
AQKFQGRVTI TADTSTSTAY MELSSLRSED TAVYYCARGG WFDYWGQGTL VTVSS        115

SEQ ID NO: 38          moltype = AA    length = 115
```

```
FEATURE                 Location/Qualifiers
source                  1..115
                        mol_type = protein
                        organism = synthetic construct
SEQUENCE: 38
QVQLVQSGAE VKKPGSSVKV SCKASGHKFT SSYINWVRQA PGQGLEWMGT INAVSGSTSY   60
AQKFQGRVTI TADTSTSTAY MELSSLRSED TAVYYCARGG WFDYWGQGTL VTVSS        115

SEQ ID NO: 39           moltype = AA  length = 111
FEATURE                 Location/Qualifiers
source                  1..111
                        mol_type = protein
                        organism = synthetic construct
SEQUENCE: 39
QSALTQPRSV SGSPGQSVTI SCTGTSSDVG SKNYVNWYQQ HPGKAPKHMI YGVSKRESGV   60
PDRFSGSKSG NTASLTISGL QAEDEADYYC GTFAGGKYYG VFGGGTKLTV L            111

SEQ ID NO: 40           moltype = AA  length = 111
FEATURE                 Location/Qualifiers
source                  1..111
                        mol_type = protein
                        organism = synthetic construct
SEQUENCE: 40
QSALTQPRSV SGSPGQSVTI SCTGTSSDVG SKNYVNWYQQ HPGKAPKLMI HGVSKRESGV   60
PDRFSGSKSG NTASLTISGL QAEDEADYYC GTFAGGKYYG VFGGGTKLTV L            111

SEQ ID NO: 41           moltype = AA  length = 7
FEATURE                 Location/Qualifiers
source                  1..7
                        mol_type = protein
                        organism = synthetic construct
SEQUENCE: 41
GVSKRHS                                                             7

SEQ ID NO: 42           moltype = AA  length = 111
FEATURE                 Location/Qualifiers
source                  1..111
                        mol_type = protein
                        organism = synthetic construct
SEQUENCE: 42
QSALTQPRSV SGSPGQSVTI SCTGTSSDVG SKNYVNWYQQ HPGKAPKLMI YGVSKRHSGV   60
PDRFSGSKSG NTASLTISGL QAEDEADYYC GTFAGGKYYG VFGGGTKLTV L            111

SEQ ID NO: 43           moltype = AA  length = 115
FEATURE                 Location/Qualifiers
source                  1..115
                        mol_type = protein
                        organism = synthetic construct
SEQUENCE: 43
QVQLVQSGAE VKKPGASVKV SCKASGYKFT SSYINWVRQA PGQGLEWMGT INPVSGSTSY   60
AQKFQGRVTM TRDTSISTAY MELSRLRSDD TAVYYCARGG WFDYWGQGTL VTVSS        115

SEQ ID NO: 44           moltype = AA  length = 7
FEATURE                 Location/Qualifiers
source                  1..7
                        mol_type = protein
                        organism = synthetic construct
SEQUENCE: 44
GVSKRPR                                                             7

SEQ ID NO: 45           moltype = AA  length = 111
FEATURE                 Location/Qualifiers
source                  1..111
                        mol_type = protein
                        organism = synthetic construct
SEQUENCE: 45
QSALTQPASV SGSPGQSITI SCTGTSSDVG SYNYVNWYQQ HPGKAPKLMI YGVSKRPRGV   60
SNRFSGSKSG NTASLTISGL QAEDEADYYC GTFAGGSYYG VFGGGTKLTV L            111

SEQ ID NO: 46           moltype = AA  length = 111
FEATURE                 Location/Qualifiers
source                  1..111
                        mol_type = protein
                        organism = synthetic construct
SEQUENCE: 46
QSALTQPRSV SGSPGQSVTI SCTGTSSDVG SYNYVNWYQQ HPGKAPKLMI YGVSKRPSGV   60
PDRFSGSKSG NTASLTISGL QAEDEADYYC GTFAGGSYYG VFGGGTKLTV L            111

SEQ ID NO: 47           moltype = AA  length = 115
```

```
FEATURE                 Location/Qualifiers
source                  1..115
                        mol_type = protein
                        organism = synthetic construct
SEQUENCE: 47
QVQLVQSGAE VKKPGSSVKV SCKASGYKFT SSYINWVRQA PGQGLEWMGT INPVSGSTSY    60
AQKFQGRVTI TADTSTSTAY MELSSLRSED TAVYYCARGG WFDYWGQGTL VTVSS        115

SEQ ID NO: 48           moltype = AA   length = 111
FEATURE                 Location/Qualifiers
source                  1..111
                        mol_type = protein
                        organism = synthetic construct
SEQUENCE: 48
QSALTQPRSV SGSPGQSVTI SCTGTSSDVG SYNYVNWYQQ HPGKAPKLMI YGVSKRPRGV    60
PDRFSGSKSG NTASLTISGL QAEDEADYYC GTFAGGSYYG VFGGGTKLTV L            111

SEQ ID NO: 49           moltype = AA   length = 6
FEATURE                 Location/Qualifiers
source                  1..6
                        mol_type = protein
                        organism = synthetic construct
SEQUENCE: 49
GGWFDV                                                               6

SEQ ID NO: 50           moltype = AA   length = 6
FEATURE                 Location/Qualifiers
source                  1..6
                        mol_type = protein
                        organism = synthetic construct
SEQUENCE: 50
SGWFDY                                                               6

SEQ ID NO: 51           moltype = AA   length = 14
FEATURE                 Location/Qualifiers
source                  1..14
                        mol_type = protein
                        organism = synthetic construct
SEQUENCE: 51
TGTSSDVGSY NVVN                                                     14

SEQ ID NO: 52           moltype = AA   length = 14
FEATURE                 Location/Qualifiers
source                  1..14
                        mol_type = protein
                        organism = synthetic construct
SEQUENCE: 52
TGTSSDVGSG NYVN                                                     14

SEQ ID NO: 53           moltype = AA   length = 14
FEATURE                 Location/Qualifiers
source                  1..14
                        mol_type = protein
                        organism = synthetic construct
SEQUENCE: 53
TGTSSDIGSY NYVN                                                     14

SEQ ID NO: 54           moltype = AA   length = 14
FEATURE                 Location/Qualifiers
source                  1..14
                        mol_type = protein
                        organism = synthetic construct
SEQUENCE: 54
TGTSSDVGSY DYVN                                                     14

SEQ ID NO: 55           moltype = AA   length = 7
FEATURE                 Location/Qualifiers
source                  1..7
                        mol_type = protein
                        organism = synthetic construct
SEQUENCE: 55
GVSKQQS                                                              7

SEQ ID NO: 56           moltype = AA   length = 7
FEATURE                 Location/Qualifiers
source                  1..7
                        mol_type = protein
                        organism = synthetic construct
SEQUENCE: 56
```

```
GVSKRQS                                                                  7

SEQ ID NO: 57           moltype = AA  length = 11
FEATURE                 Location/Qualifiers
source                  1..11
                        mol_type = protein
                        organism = synthetic construct
SEQUENCE: 57
GTFAGGKYYG V                                                            11

SEQ ID NO: 58           moltype = AA  length = 111
FEATURE                 Location/Qualifiers
source                  1..111
                        mol_type = protein
                        organism = synthetic construct
SEQUENCE: 58
QSALTQPASV SGSPGQSITI SCTGTSSDVG SYNYVNWYQQ HPGKAPKLMI YGVSKRESGV         60
SNRFSGSKSG NTASLTISGL QAEDEADYYC GTFAGGAYYG VFGGGTKLTV L                 111

SEQ ID NO: 59           moltype = AA  length = 115
FEATURE                 Location/Qualifiers
source                  1..115
                        mol_type = protein
                        organism = synthetic construct
SEQUENCE: 59
QVQLVQSGAE VRKPGASVKV SCKASGYTFT SSYINWVRQA PGQGLEWMGT INPVSGSTSY         60
AQKFQGRVTM TRDTSISTAY MELSRLRSDD TAVYYCARGG WFDYWGQGTL VTVSS             115

SEQ ID NO: 60           moltype = AA  length = 111
FEATURE                 Location/Qualifiers
source                  1..111
                        mol_type = protein
                        organism = synthetic construct
SEQUENCE: 60
QSALTQPASV SGSPGQSITI SCTGTSSDVG SYNRVNWYQQ HPGKAPKLMI YGVSKRESGV         60
SNRFSGSKSG NTASLTISGL QAEDEADYYC GTFAGGRYYG VFGGGTKLTV L                 111

SEQ ID NO: 61           moltype = AA  length = 111
FEATURE                 Location/Qualifiers
source                  1..111
                        mol_type = protein
                        organism = synthetic construct
SEQUENCE: 61
QSALTQPASV SGSPGQSITI SCTGTSSDVG SGNYVNWYQQ HPGKAPKLMI YGVSKRESGV         60
SNRFSGSKSG NTASLTISGL QAEDEADYYC GTFAGGKYYG VFGGGTKLTV L                 111

SEQ ID NO: 62           moltype = AA  length = 115
FEATURE                 Location/Qualifiers
source                  1..115
                        mol_type = protein
                        organism = synthetic construct
SEQUENCE: 62
QVQLVQSGAE VKKPGASVKV SCKASGYTFT SSYINWVRQA PGQGLEWMGT INAVSGSTSY         60
AQKFQGRVTM TRDTSISTAY MELSRLRSDD TAVYYCARGG WFDVWGQGTL VTVSS             115

SEQ ID NO: 63           moltype = AA  length = 111
FEATURE                 Location/Qualifiers
source                  1..111
                        mol_type = protein
                        organism = synthetic construct
SEQUENCE: 63
QSALTQPASV SGSPGQSITI SCTGTSSDIG SYNYVNWYQQ HPGKAPKLMI YGVSKRESGV         60
SNRFSGSKSG NTASLTISGL QAEDEADYYC GTFAGGSYYG VFGGGTKLTV L                 111

SEQ ID NO: 64           moltype = AA  length = 115
FEATURE                 Location/Qualifiers
source                  1..115
                        mol_type = protein
                        organism = synthetic construct
SEQUENCE: 64
QVQLVQSGAE VKKPGASVKV SCKASGYTFT SSYINWVRQA PGQGLEWMGT INAVSGSTSY         60
AQKFQGRVTM TRDTSISTAY MELSRLRSDD TAVYYCARGG WFDYWGQGTL VTVSS             115

SEQ ID NO: 65           moltype = AA  length = 111
FEATURE                 Location/Qualifiers
source                  1..111
                        mol_type = protein
                        organism = synthetic construct
SEQUENCE: 65
```

```
QSALTQPASV SGSPGQSITI SCTGTSSDVG SFNYVNWYQQ HPGKAPKLMI KGVSKRESGV    60
SNRFSGSKSG NTASLTISGL QAEDEADYYC GTFAGGAYYG VFGGGTKLTV L            111

SEQ ID NO: 66              moltype = AA   length = 115
FEATURE                    Location/Qualifiers
source                     1..115
                           mol_type = protein
                           organism = synthetic construct
SEQUENCE: 66
QVQLVQSGAE VKKPGASVKV SCKASGYTFT SSYINWVRQA PGQGLEWMGT INAVSGSTSY    60
AQKFQGRVTM TRDTSISTAY MELSRLRSDD TAVYYCARSG WFDYWGQGTL VTVSS        115

SEQ ID NO: 67              moltype = AA   length = 111
FEATURE                    Location/Qualifiers
source                     1..111
                           mol_type = protein
                           organism = synthetic construct
SEQUENCE: 67
QSALTQPASV SGSPGQSITI SCTGTSSDVG SYNYVNWYQQ HPGKAPKLMI YGVSKQQSGV    60
SNRFSGSKSG NTASLTISGL QAEDEADYYC GTFAGGSYYG VFGGGTKLTV L            111

SEQ ID NO: 68              moltype = AA   length = 111
FEATURE                    Location/Qualifiers
source                     1..111
                           mol_type = protein
                           organism = synthetic construct
SEQUENCE: 68
QSALTQPASV SGSPGQSITI SCTGTSSDVG SKNYVNWYQQ HPGKAPKLMI YGVSKRESGV    60
SNRFSGSKSG NTASLTISGL QAEDEADYYC GTFAGGKYYG VFGGGTKLTV L            111

SEQ ID NO: 69              moltype = AA   length = 111
FEATURE                    Location/Qualifiers
source                     1..111
                           mol_type = protein
                           organism = synthetic construct
SEQUENCE: 69
QSALTQPASV SGSPGQSITI SCTGTSSDVG SFNYVNWYQQ HPGKAPKLMI RGVSKRESGV    60
SNRFSGSKSG NTASLTISGL QAEDEADYYC GTFAGGAYYG VFGGGTKLTV L            111

SEQ ID NO: 70              moltype = AA   length = 115
FEATURE                    Location/Qualifiers
source                     1..115
                           mol_type = protein
                           organism = synthetic construct
SEQUENCE: 70
QVQLVQSGAE VKKPGASVKV SCKASGYTFT SSYINWVRQA PGQGLEWMGT INAVSGSTSY    60
AQKFQGRVTM TRDESISTAY MELSRLRSDD TAVYYCARGG WFDYWGQGTL VTVSS        115

SEQ ID NO: 71              moltype = AA   length = 115
FEATURE                    Location/Qualifiers
source                     1..115
                           mol_type = protein
                           organism = synthetic construct
SEQUENCE: 71
QVQLVQSGAE VKKPGASVKV SCKASGYTFT SSYINWVRQA PGQGLEWMGT INAVSGSTSY    60
AQKFQGRVTM TRDVSISTAY MELSRLRSDD TAVYYCARGG WFDYWGQGTL VTVSS        115

SEQ ID NO: 72              moltype = AA   length = 111
FEATURE                    Location/Qualifiers
source                     1..111
                           mol_type = protein
                           organism = synthetic construct
SEQUENCE: 72
QSALTQPASV SGSPGQSITI SCTGTSSDVG SYNYVNWYQQ HPGKAPKLMI YGVSKRESGV    60
SNRFSGSKSG NTASLTISGL QAEDEADYYC GTFAGGKYYG VFGGGTKLTV L            111

SEQ ID NO: 73              moltype = AA   length = 111
FEATURE                    Location/Qualifiers
source                     1..111
                           mol_type = protein
                           organism = synthetic construct
SEQUENCE: 73
QSALTQPASV SGSPGQSITI SCTGTSSDVG SYNYVNWYQQ HPGKAPKLMI YGVSKRDSGV    60
SNRFSGSKSG NTASLTISGL QAEDEADYYC GTFAGGKYYG VFGGGTKLTV L            111

SEQ ID NO: 74              moltype = AA   length = 111
FEATURE                    Location/Qualifiers
source                     1..111
                           mol_type = protein
```

```
                        organism = synthetic construct
SEQUENCE: 74
QSALTQPASV SGSPGQSITI SCTGTSSDVG SRNYVNWYQQ HPGKAPKLMI YGVSKRESGV    60
SNRFSGSKSG NTASLTISGL QAEDEADYYC GTFAGGDYYG VFGGGTKLTV L            111

SEQ ID NO: 75           moltype = AA  length = 111
FEATURE                 Location/Qualifiers
source                  1..111
                        mol_type = protein
                        organism = synthetic construct
SEQUENCE: 75
QSALTQPASV SGSPGQSITI SCTGTSSDVG SANYVNWYQQ HPGKAPKPMI YGVSRRPSGV    60
SNRFSGSKSG NTASLTISGL QAEDEADYYC GTFAGGKYYG VFGGGTKLTV L            111

SEQ ID NO: 76           moltype = AA  length = 111
FEATURE                 Location/Qualifiers
source                  1..111
                        mol_type = protein
                        organism = synthetic construct
SEQUENCE: 76
QSALTQPASV SGSPGQSITI SCTGTSSDVG SYDYVNWYQQ HPGKAPKLMI HGVSKRESGV    60
SNRFSGSKSG NTASLTISGL QAEDEADYYC GTFAGGSYYG VFGGGTKLTV L            111

SEQ ID NO: 77           moltype = AA  length = 111
FEATURE                 Location/Qualifiers
source                  1..111
                        mol_type = protein
                        organism = synthetic construct
SEQUENCE: 77
QSALTQPASV SGSPGQSITI SCTGTSSDVG SKNYVNWYQQ HPGKAPKLMI YGVSKRQSGV    60
SNRFSGSKSG NTASLTISGL QAEDEADYYC GTFAGGDYYG VFGGGTKLTV L            111

SEQ ID NO: 78           moltype = AA  length = 111
FEATURE                 Location/Qualifiers
source                  1..111
                        mol_type = protein
                        organism = synthetic construct
SEQUENCE: 78
QSALTQPASV SGSPGQSITI SCTGTSSDVG SYNVVNWYQQ HPGKAPKLMI SGVSKRESGV    60
SNRFSGSKSG NTASLTISGL QAEDEADYYC GTFAGGKYYG VFGGGTKLTV L            111

SEQ ID NO: 79           moltype = AA  length = 11
FEATURE                 Location/Qualifiers
source                  1..11
                        mol_type = protein
                        organism = synthetic construct
SEQUENCE: 79
GTFAGGSYRG V                                                         11

SEQ ID NO: 80           moltype = AA  length = 111
FEATURE                 Location/Qualifiers
source                  1..111
                        mol_type = protein
                        organism = synthetic construct
SEQUENCE: 80
QSALTQPASV SGSPGQSITI SCTGTSSDVG SYNYVNWYQQ HPGKAPKLMI YGVSKRESGV    60
SNRFSGSKSG NTASLTISGL QAEDEADYYC GTFAGGSYRG VFGGGTKLTV L            111
```

ANTIBODIES TARGETING ACTRIIA AND ACTRIIB

This patent application is a continuation of U.S. application Ser. No. 18/898,854 filed Sep. 27, 2024 which claims the benefit of priority from EP 23200478.8 filed Sep. 28, 2023, teachings of each of which are incorporated herein by reference in their entirety.

FIELD OF THE INVENTION

The present disclosure relates to antibodies and antibody fragments that are specific for ActRIIA and ActRIIB. The antibodies are improved versions of bimagrumab. Antibodies of the present invention have an improved affinity against ActRIIA, translating into improved in vitro potency and efficacy, an improved PK and PD profile and a higher stability making the antibodies suitable for s.c. administration. Optionally they carry Fc modifications making the antibodies safe for prolonged treatments.

STATEMENT REGARDING ELECTRONIC FILING OF A SEQUENCE LISTING

A Sequence Listing in XML text format, submitted under 37 C.F.R. § 1.821-1.834, entitled "BHIP-C19-02WO_sequence listing.xml," 76,229 bytes in size, created Sep. 25, 2024, and filed via Patent Center, is provided in lieu of a paper copy. This Sequence Listing is hereby incorporated by reference into the specification.

BACKGROUND

Activins are dimeric growth and differentiation factors which belong to the transforming growth factor-beta (TGF-beta) superfamily of structurally related signaling proteins. Activins signal through a heterodimeric complex of receptor serine kinases which include at least two type I (I and IB) and two type II (II and IIB, aka ACVR2A and ACVR2B) receptors. These receptors are all transmembrane proteins, composed of a ligand-binding extracellular domain with cysteine-rich region, a transmembrane domain, and a cytoplasmic domain with predicted serine/threonine specificity. Type I receptors are essential for signaling while type II receptors are required for binding ligands and for expression of type I receptors. Type I and II receptors form a stable complex after ligand binding resulting in the phosphorylation of type I receptors by type II receptors.

The activin receptor II A and B (ActRIIA, ActRIIB) are receptor for myostatin. The interaction between myostatin and the receptors regulates the inhibition of skeletal muscle differentiation via the Smad-dependent pathway. Thus, by inhibiting or preventing myostatin from binding to ActRIIA and B, one can induce the formation of skeletal muscle. Blockade of ActRII A or ActRII B alone is not sufficient to induce formation of skeletal muscle (Proc Natl Acad Sci USA (2017) 114:12448-53).

Bogdanovich et al (Nature, 2002, 420:418-421) describes that anti-myostatin antibodies were able to block myostatin, resulting in an increase in muscle mass in a mouse model of Duchenne muscular dystrophy. Bradley et al (Cell MoI. Life Sci. 2008, 65:2119-2124) have reviewed the different available approaches for modulating the myostatin/ActRIIB interaction, including the aforementioned anti-myostatin antibodies, inhibiting the release of mature myostatin by administering the myostatin propeptide, administering follistatin to block the myostatin receptor, administering HDAC inhibitors to induce follistatin production, administering an altered myostatin peptide which prevents myostatin from binding the receptor and administering a soluble decoy receptor for myostatin.

Bimagrumab (BYM338) is a human monoclonal antibody targeting ActRIIB, with strongly reduced binding to ActRIIA. It was isolated from a phage display library and developed for the treatment pathological muscle loss and weakness. Bimagrumab was also reported to be safe and effective for treating excess adiposity and metabolic disturbances of adult patients with obesity and type 2 diabetes. In January 2023, it entered a phase IIb trials for obesity. Bimagrumab is disclosed in WO2010/125003.

However, bimagrumab has several properties that make the antibody not ideal for human administration. The present invention addressees these shortcomings and provides novel and improved derivatives of bimagrumab. For example, the present invention provides antibodies that are not only reactive with ActRIIB, but also have a high affinity for ActRIIA. At the same time the biophysical properties of bimagrumab were improved. The antibodies of the present invention not only have less unspecific binding, but also exhibit an improved HIC score, reduced charged based interactions and a reduced viscosity. This translates into a higher efficacy as demonstrated in in vivo mouse models, improved pharmacokinetic parameters as demonstrated in cynomolgus monkeys and minipigs and improved formulatability.

SUMMARY OF THE INVENTION

The present invention relates to an antibody or antibody fragment specific for human ActRIIB, wherein said antibody or antibody fragment has a higher affinity to human ActRIIA than an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments said antibody or antibody fragment has one or more of the following additional properties compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8:
 a) less unspecific binding,
 b) an improved HIC score,
 c) an improved Heparin score,
 d) a lower IC95 in a myostatin inhibition assay,
 e) a lower IC95 in an activin inhibition assay, or
 f) a reduced viscosity.

The present invention relates to an antibody or antibody fragment specific for human ActRIIB, wherein said antibody or antibody fragment comprises
 a) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14,
 b) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18, c) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14, d) a HCDR1 region of SEQ ID NO: 3, a. HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14, e) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18, f) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27, g) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14, h) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34, i) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, or j) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14.

The present invention also relates to an antibody or antibody fragment specific for human ActRIIB, wherein said antibody or antibody fragment comprises a) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, b) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18, c) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14, d) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14, e) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18, f) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27, g) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14, h) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34, i) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, j) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14, k) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14, or l) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14.

The present invention relates to an antibody or antibody fragment specific for human ActRIIB, wherein said antibody or antibody fragment comprises a) a variable heavy chain of SEQ ID NO: 12 and a variable light chain of SEQ ID NO: 15, b) a variable heavy chain of SEQ ID NO: 16 and a variable light chain of SEQ ID NO: 19, c) a variable heavy chain of SEQ ID NO: 16 and a variable light chain of SEQ ID NO: 21, d) a variable heavy chain of SEQ ID NO: 16 and a variable light chain of SEQ ID NO: 23, e) a variable heavy chain of SEQ ID NO: 24 and a variable light chain of SEQ ID NO: 25, f) a variable heavy chain of SEQ ID NO: 16 and a variable light chain of SEQ ID NO: 28, g) a variable heavy chain of SEQ ID NO: 16 and a variable light chain of SEQ ID NO: 31, h) a variable heavy chain of SEQ ID NO: 32 and a variable light chain of SEQ ID NO: 35, i) a variable heavy chain of SEQ ID NO: 36 and a variable light chain of SEQ ID NO: 15, j) a variable heavy chain of SEQ ID NO: 37 and a variable light chain of SEQ ID NO: 21, k) a variable heavy chain of SEQ ID NO: 37 and a variable light chain of SEQ ID NO: 23, l) a variable heavy chain of SEQ ID NO: 38 and a variable light chain of SEQ ID NO: 23, m) a variable heavy chain of SEQ ID NO: 37 and a variable light chain of SEQ ID NO: 39, n) a variable heavy chain of SEQ ID NO: 37 and a variable light chain of SEQ ID NO: 40, or o) a variable heavy chain of SEQ ID NO: 37 and a variable light chain of SEQ ID NO: 42.

In certain embodiments, said an antibody specific for human ActRIIB, comprises a modification in the Fc region which increase the half-life of said antibody, preferably wherein said modification is a YTE mutation (M252Y/S254T/T256E).

In certain embodiments, said an antibody specific for human ActRIIB, comprises a silencing modification in the Fc region. Preferably, said silencing mutation is selected from a PA-LALA, a PG-LALA or an AEASS mutation.

In certain embodiments, said an antibody specific for human ActRIIB, is conjugated or fused to an additional pharmaceutical active moiety.

In certain embodiments, said an antibody specific for human ActRIIB, is conjugated or fused to an additional pharmaceutical active moiety.

In certain embodiments, the present invention relates to aforementioned antibodies or antibody fragments specific for human ActRIIB for use in medicine. Preferably said use in medicine is the treatment of a metabolic disease, obesity, type-2 diabetes or a cardiovascular disease.

In certain embodiments, the present invention relates to a nucleic acid composition comprising a nucleic acid sequence or a plurality of nucleic acid sequences encoding aforementioned antibody or antibody fragment.

In certain embodiments, the present invention relates to a vector comprising aforementioned nucleic acid composition.

In certain embodiments, the present invention relates to a host cell comprising aforementioned vector or aforementioned nucleic acid composition.

In certain embodiments, the present invention relates to a pharmaceutical composition comprising aforementioned antibody or antibody fragment and a pharmaceutically acceptable carrier or excipient.

Definitions

Figure 1:
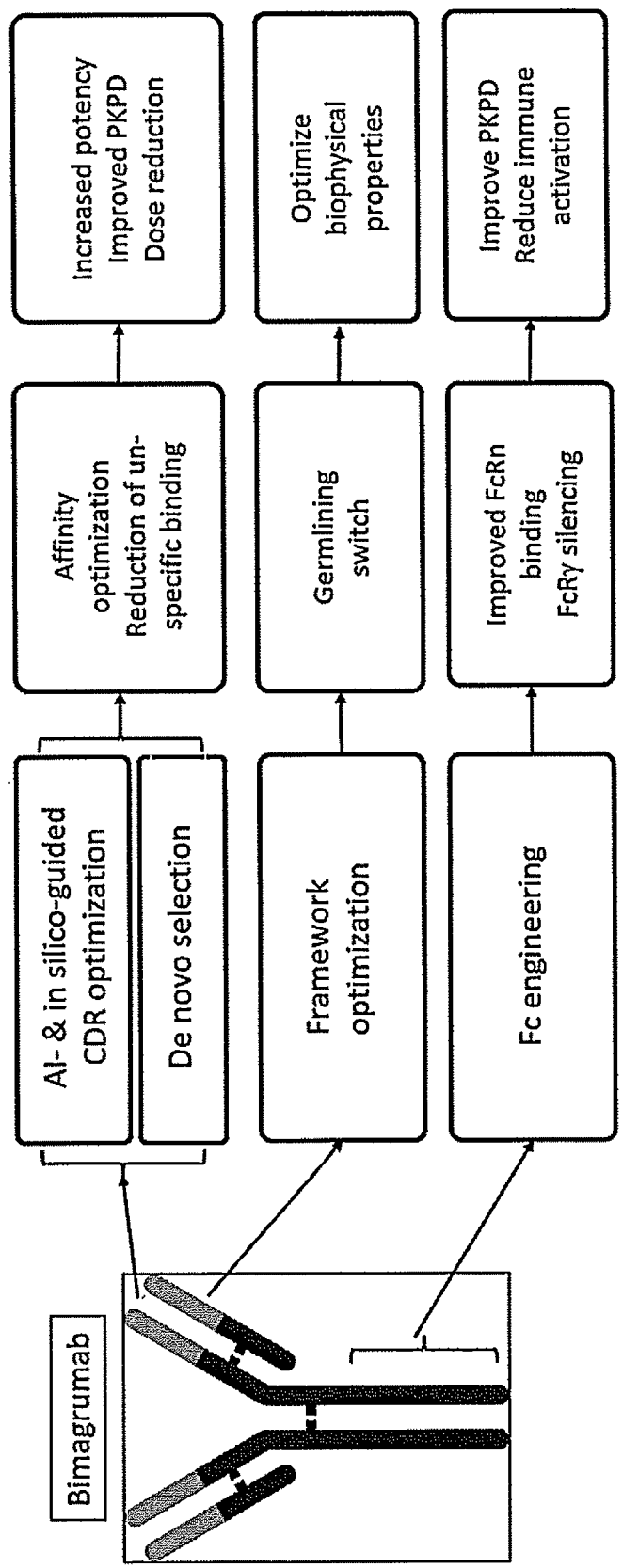
FIG. 1 shows a schematic overview about the experimental approaches taken with the ultimate goal to improve antibody bimagrumab.

The disclosure pertains to antibodies, which specifically bind to ActRIIA and/or ActRIIB, and uses of such antibodies, in particular therapeutic uses.

The terms "ActRIIA" and "ACVR2A" as used herein refers to the human protein with UniProt ID P27037. ActRIIA has the following amino acid sequence:

(SEQ ID No. 1)
MGAAAKLAFAVELISCSSGAILGRSETQECLFFNANWEKDRTNQTGVEP

CYGDKDKRRHCFATWKNISGSIEIVKQGCWLDDINCYDRTDCVEKKDSP

EVYFCCCEGNMCNEKFSYFPEMEVTQPTSNPVTPKPPYYNILLYSLVPL

MLIAGIVICAFWVYRHHKMAYPPVLVPTQDPGPPPPSPLLGLKPLQLLE

VKARGREGCVWKAQLLNEYVAVKIFPIQDKOSWQNEYEVYSLPGMKHEN

ILQFIGAEKRGTSVDVDLWLITAFHEKGSLSDFLKANVVSWNELCHIAE

TMARGLAYLHEDIPGLKDGHKPAISHRDIKSKNVLLKNNLTACIADFGL

ALKFEAGKSAGDTHGQVGTRRYMAPEVLEGAINFQRDAFLRIDMYAMGL

VLWELASRCTAADGPVDEYMLPFEEEIGQHPSLEDMQEVVVHKKKRPVL

RDYWQKHAGMAMLCETIEECWDHDAEARLSAGCVGERITQMQRLTNIIT

TEDIVTVVTMVINVDFPPKESSL.

The terms "ActRIIB and "ACVR2B" as used herein refers to the human protein with UniProt ID Q13705. ActRIIB has the following amino acid sequence:

(SEQ ID No. 2)
MTAPWVALALLWGSLCAGSGRGEAETRECIYYNANWELERTNQSGLERC

EGEQDKRLHCYASWRNSSGTIELVKKGCWLDDENCYDRQECVATEENPQ

VYFCCCEGNFCNERFTHLPEAGGPEVTYEPPPTAPTLLTVLAYSLLPIG

GLSLIVLLAFWMYRHRKPPYGHVDIHEDPGPPPPSPLVGLKPLOLLEIK

ARGRFGCVWKAQLMNDFVAVKIFPLQDKQSWQSEREIFSTPGMKHENLL

QFIAAEKRGSNLEVELWLITAFHDKGSLTDYLKGNIITWNELCHVAETM

SRGLSYLHEDVPWCRGEGHKPSIAHRDFKSKNVLLKSDLTAVLADFGLA

-continued

```
VRFEPGKPPGDTHGQVGTRRYMAPEVLEGAINFORDAFLRIDMYAMGLV

LWELVSRCKAADGPVDEYMLPFEEEIGQHPSLEELQEVVVHKKMRPTIK

DHWLKHPGLAQLCVTIEECWDHDAEARLSAGCVEERVSLIRRSVNGTTS

DCLVSLVTSVTNVDLPPKESSI.
```

Activin receptor II A (ActRIIA) and Activin receptor II B (ActRIIB) are receptors for myostatin, activin, and bone morphogenetic proteins (BMPs). The interaction between myostatin and these receptors regulates the inhibition of skeletal muscle differentiation via the Smad-dependent pathway. It is thought that by inhibiting or preventing myostatin from binding to ActRIIA and ActRIIB, e.g, via an ActRII receptor antibody, the formation of skeletal muscle can be induced (Proc Natl Acad Sci USA (2017) 114:12448-53).

The term "antibody" as used herein refers to a protein comprising at least two heavy (H) chains and two light (L) chains inter-connected by disulfide bonds, which interacts with an antigen. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass. Both the light and heavy chains are divided into regions of structural and functional homology.

The term "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1 126-1 136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into single chain molecules comprising a pair of tandem Fv segments (VH-CH1-VH-CH1) which, together with complementary light chain polypeptides, form a pair of antigen-binding sites (Zapata et al., (1995) Protein Eng. 8: 1057-1062; and U.S. Pat. No. 5,641,870).

The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g. Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mol. Biol. 273:927-948; Annals of the New York Academy of Sciences, 764, 47-49 (1995); Nucleic Acids Research, 25, 206-211 (1997).

A "human antibody" or "human antibody fragment", as used herein, is an antibody and antibody fragment having variable regions in which both the framework and CDR regions are from sequences of human origin. Human antibodies can also be isolated from synthetic libraries or from transgenic mice (e.g. Xenomouse, OmniMouse, Harbour Mouse, ATX-Gx Mouse, Trianni Mouse) provided the respective system yield in antibodies having variable regions in which both the framework and CDR regions are derived from sequences of human origin. Furthermore, if the antibody contains a constant region, the constant region also is derived from such sequences. Human origin includes, e.g., human germline sequences, or mutated versions of human germline sequences or antibody containing consensus framework sequences derived from human framework sequences analysis, for example, as described in Knappik et al., (2000) J Mol Biol 296:57-86).

A "humanized antibody" or "humanized antibody fragment" is defined herein as an antibody molecule, which has constant antibody regions derived from sequences of human origin and the variable antibody regions or parts thereof or only the CDRs are derived from another species. For example, a humanized antibody can be CDR-grafted, wherein the CDRs of the variable domain are from a non-human origin, while one or more frameworks of the variable domain are of human origin and the constant domain (if any) is of human origin.

The term "chimeric antibody" or "chimeric antibody fragment" is defined herein as an antibody molecule, which has constant antibody regions derived from, or corresponding to, sequences found in one species and variable antibody regions derived from another species. Preferably, the constant antibody regions are derived from, or corresponding to, sequences found in humans, and the variable antibody regions (e.g. VH, VL, CDR or FR regions) are derived from sequences found in a non-human animal, e.g. a mouse, rat, rabbit or hamster.

The term "isolated antibody" or "isolated antibody fragment" refers to an antibody or antibody fragment that is substantially free of other antibodies or antibody fragments having different antigenic specificities. Moreover, an isolated antibody or antibody fragment may be substantially free of other cellular material and/or chemicals. Thus, in some aspects, antibodies provided are isolated antibodies, which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

The term "recombinant antibody" or "recombinant antibody fragment", as used herein, includes all antibodies or antibody fragment that are prepared, expressed, created or segregated by means not existing in nature. For example, antibodies isolated from a host cell transformed to express the antibody, antibodies selected and isolated from a recombinant, combinatorial human antibody library, and antibodies prepared, expressed, created or isolated by any other means that involve splicing of all or a portion of a human immunoglobulin gene, sequences to other DNA sequences or antibodies isolated from an animal (e.g., a mouse) that is transgenic or transchromosomal for human immunoglobulin genes or a hybridoma prepared therefrom. Preferably, such recombinant antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. A recombinant antibody may be a monoclonal antibody.

The term "monoclonal" as used herein has the meaning typically ascribed to it in the art, namely an antibody or an antibody fragment (or its corresponding functional fragment) arising from a single clone of an antibody-producing cell, recognizing a single epitope on the antigen bound.

As used herein, an antibody "binds specifically to", "specifically binds to", is "specific to/for" or "specifically recognizes" an antigen, such as human ActRIIA or ActRIIB, if such antibody is able to discriminate between such antigen and one or more reference antigen(s), since binding specificity is not an absolute, but a relative property. For example, a standard ELISA assay or standard flow cytometry assay can be carried out. The scoring may be carried out by standard color development (e.g. secondary antibody with horseradish peroxide and tetramethyl benzidine with hydrogen peroxide) or by binding of a secondary antibody labeled with PE or another dye or marker. The reaction in certain wells is scored by the optical density (OD), for example, at 450 nm or by mean or median fluorescence intensity (MFI) in flow cytometry. Typical background (=negative reaction) may be 0.1 OD; typical positive reaction may be 1 OD. Background and positive reaction MFI are highly dependent on instrument settings. The difference positive/negative can be more than 10-fold. Typically, determination of binding specificity is performed by using not a single reference antigen, but a set of about three to five unrelated antigens, such as milk powder, BSA, transferrin or the like. For flow cytometry various antigen-negative cells can be used. An antibody that specifically binds to an antigen may however have cross-reactivity to the respective orthologous antigen from other species (e.g., species homologs). In certain embodiments such cross-reactivity to an orthologous antigen is even preferred.

As used herein, an antibody has "cross-reactivity" or is "cross-reactive" if it binds to the a closely related antigen or the same antigen from other species. In the present disclosure the term is used for an antibody that is specific for ActRIIB, but that also binds to ActRIIA.

The term "ActRII receptor antibody" as used herein refers to an antibody specific for ActRIIA, an antibodies specific for ActRIIB, and an antibodies specific for ActRIIA and ctRIIB, i.e. antibodies with a cross-reactivity between ActRIIA and ActRIIB.

The term "bimagrumab" refers to an antibody also known as BYM338 and disclosed in WO2010/125003. Bimagrumab has the following amino acid sequence.

TABLE 1

| SEQ ID No. | Description | Sequence |
|---|---|---|
| 3 | CDRH1 (Kabat) | SSYIN |
| 4 | CDRH2 (Kabat) | TINPVSGSTSYAQKFQG |
| 5 | CDRH3 (Kabat) | GGWFDY |
| 6 | CDRL1 (Kabat) | TGTSSDVGSYNYVN |
| 7 | CDRL2 (Kabat) | GVSKRPS |
| 8 | CDRL3 (Kabat) | GTFAGGSYYGV |
| 9 | VH | QVQLVQSGAEVKKPGASVKVSCKASGYTFTSSYINWVRQAPGQGLEWMGTINPVSGSTSYAQKFQGRVTMTRDTSISTAYMELSRLRSDDTAVYYCARGGWFDYWGQGTLVTVSS |
| 10 | VL | QSALTQPASVSGSPGQSITISCTGTSSDVGSYNYVNWYQQHPGKAPKLMIYGVSKRPSGVSNRFSGSKSGNTASLTISGLQAEDEADYYCGTFAGGSYYGVFGGGTKLTVL |

As used herein, the term "affinity" refers to the strength of interaction between the polypeptide and its target at a single site. Within each site, the binding region of the polypeptide interacts through weak non-covalent forces with its target at numerous sites; the more interactions, the stronger the affinity.

The term "epitope" includes any proteinaceous region which is specifically recognized by an antibody or antibody fragment thereof or otherwise interacts with a molecule. Generally, epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

The term "domain" or "protein domain" refers to a region of a protein's polypeptide chain that forms a functional unit and/or independently forms a three-dimensional structure.

"Compositions" of the present disclosure may be used for therapeutic or prophylactic applications. The present disclosure, therefore, includes a pharmaceutical composition containing an antibody or antibody fragment as disclosed herein and a pharmaceutically acceptable carrier or excipient therefore. In a related aspect, the present disclosure provides a method for treating inflammatory diseases, autoimmune diseases, hematologic malignancies and potentially other diseases. Such method contains the steps of administering to a subject in need thereof an effective amount of the pharmaceutical composition that contains an antibody or antibody fragment as described herein.

The present disclosure provides therapeutic methods comprising the administration of a therapeutically effective amount of an antibody or antibody fragment as disclosed herein to a subject in need of such treatment. A "therapeutically effective amount" or "effective amount", as used herein, refers to the amount of an ActRII receptor antibody necessary to elicit the desired biological response. In accordance with the subject disclosure, the therapeutic effective amount is the amount of an ActRII receptor antibody necessary to treat and/or prevent a disease.

"Administered" or "administration" includes but is not limited to delivery of a drug by an injectable form, such as, for example, an intravenous, intramuscular, intradermal or subcutaneous route or mucosal route, for example, as a nasal spray or aerosol for inhalation or as an ingestible solution, capsule or tablet. Preferably, the administration is by an injectable form.

As used herein, "treatment", "treat" or "treating" and the like refers to clinical intervention in an attempt to alter the natural course of a disease in the subject being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or antibody fragments according to the preset disclosure are used to delay development of a disease or to slow the progression of a disease. "Treatment", "treat", or "treating" may not necessarily include prophylaxis.

"Preventing" or "prevention" refers to a reduction in risk of acquiring or developing a disease (i.e., causing at least one of the clinical symptoms of the disease not to develop in a subject that may be exposed to a disease-causing agent, or predisposed to the disease in advance of disease onset). "Prevention" also refers to methods which aim to prevent the onset of a disease or its symptoms or which delay the onset of a disease or its symptoms.

"Subject" or "species" or as used in this context refers to any mammal, including rodents, such as mouse or rat, and primates, such as cynomolgus monkey (*Macaca fascicularis*), Marmoset monkey (Callithrix jacchus), rhesus monkey (*Macaca mulatta*) or humans (*Homo sapiens*). Preferably, the subject is a primate, most preferably a human.

The term "effector function" refers to those biological activities attributable to the Fc region of an antibody, which vary with the antibody isotype. Non-limiting examples of antibody effector functions include C1 q binding and complement dependent cytotoxicity (CDC); Fc receptor binding and antibody-dependent cell-mediated cytotoxicity (ADCC) and/or antibody-dependent cellular phagocytosis (ADCP); down regulation of cell surface receptors (e.g. B cell receptor); and direct cell activation or direct cell inhibition.

"Antibody-dependent cell-mediated cytotoxicity" or "ADCC" refers to a form of cytotoxicity in which antibodies bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes/macrophages express FcγRI, FcγRII, and FcγRIII.

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass) of the present disclosure, which are bound to their cognate antigen.

"Antibody-dependent cellular phagocytosis" or "ADCP" refers to a mechanism of elimination of antibody-coated target cells by internalization by phagocytic cells, such as macrophages or dendritic cells.

As used herein, the term "antibody-drug conjugate" or "ADC" refers to an antibody or an antibody fragment that is chemically linked to a second chemical moiety, such as a therapeutic or cytotoxic agent.

The term "cytotoxic drug" as use herein is art recognized and includes, but is not limited to, daunorubicin, mitoxantrone, doxorubicin, cucurbitacin, chaetocin, chaetoglobosin, chlamydocin, calicheamicin, mertansine, nemorubicin, cryptophyscin, mensacarcin, ansamitocin, mitomycin C, geldanamycin, mechercharmycin, rebeccamycin, safracin, okilactomycin, oligomycin, actinomycin, sandramycin, hypothemycin, polyketomycin, hydroxyellipticine, thiocolchicine, methotrexate, triptolide, taltobulin, lactacystin, dolastatin, auristatin, monomethyl auristatin E (MMAE), monomethyl auristatin F (MMAF), telomestatin, tubastatin A, combretastatin, maytansinoid, MMAD, MMAF, DM1, DM4, DTT, 16-GMB-APA-GA, 17-DMAP-GA, JW 55, a pyrrolobenzodiazepine, SN-38, Ro 5-3335, puwainaphycin, duocarmycin, bafilomycin, taxoid, tubulysin, ferulenol, lusiol A, fumagillin, hygrolidin, glucopiericidin, amanitin, ansatrienin, cinerubin, phallacidin, phalloidin, phytosphongosine, piericidin, poronetin, phodophyllotoxin, gramicidin A, sanguinarine, sinefungin, herboxidiene, microcolin B, microcystin, muscotoxin A, tolytoxin, tripolin A, myoseverin, mytoxin B, nocuolin A, psuedolaric acid B, pseurotin A, cy dopamine, curvulin, colchicine, aphidicolin, englerin, cordycepin, apoptolidin, epothilone A, limaquinone, isatropolone, isofistularin, quinaldopeptin, ixabepilone, aeroplysinin, arruginosin, agrochelin, or epothilone. An exemplary pyrrolobenzodiazepine is tesirine.

Throughout this specification, unless the context requires otherwise, the words "comprise", "have" and "include" and their respective variations such as "comprises", "comprising", "has", "having", "includes" and "including" will be understood to imply the inclusion of a stated element or integer or group of elements or integers but not the exclusion of any other element or integer or group of elements or integers.

The terms "engineered" or "modified" as used herein includes manipulation of nucleic acids or polypeptides by synthetic means (e.g., by recombinant techniques, in vitro peptide synthesis, by enzymatic or chemical coupling of peptides or some combination of these techniques). Preferably, the antibodies or antibody fragments according to the present disclosure are engineered or modified to improve one or more properties, such as antigen binding, stability, half-life, effector function, immunogenicity, safety and the like.

"Variant" as used herein refers to a polypeptide that differs from a reference polypeptide by one or more modifications for example amino acid substitutions, insertions or deletions. Variant polypeptides typically retain most of the properties of the reference polypeptide, e.g. binding to the target antigen, but introduce a novel, additional feature or property, e.g. the variant polypeptide has a higher affinity to the target antigen compared to the reference polypeptide.

The term "amino acid mutation" as used herein is meant to encompass amino acid substitutions, deletions, insertions, and modifications. Any combination of substitution, deletion, insertion, and modification can be made as long as the final construct possesses the desired characteristics, e.g., reduced binding to an Fc receptor. Amino acid sequence deletions and insertions include N- and/or C-terminal deletions and insertions of amino acid residues. Particular amino acid mutations are amino acid substitutions. Amino acid substitutions include replacement by non-naturally occurring amino acids or by naturally occurring amino acid derivatives of the twenty standard amino acids. Amino acid mutations can be generated using genetic or chemical methods well known in the art. Genetic methods may include site-directed mutagenesis, PCR, gene synthesis and the like. It is contemplated that methods of altering the side chain group of an amino acid residue by methods other than genetic engineering, such as chemical modification, may also be useful. Various designations may be used herein to indicate the same amino acid mutation. For example, a substitution of glycine at position 237 of the antibody Fc region to alanine can be indicated as 237A, G237, G237A, or Gly237Ala.

The term "IC50" as used herein, refers to the concentration of an antibody or antibody fragment, which inhibits a response in an assay half-way between the baseline and maximum. It therefore represents the antibody or ligand concentration at which 50% of the maximal inhibitory effect is observed. In analogy, the terms "IC90" and "IC95" as used herein, refer to the concentrations of an antibody or antibody fragment, which inhibit 90% or 95%, respectively, of the maximal effect in an assay The term "Ka", as used herein refers to the association rate of a particular antibody-antigen interaction The term "Kd" as used herein, refers to the dissociation rate of a particular antibody-antigen interaction. Kd values for antibodies can be determined using methods well established in the art.

The term "KD" as used herein, refer to the dissociation constant of a particular antibody-antigen interaction, which is obtained from the ratio of Kd to Ka (i.e., Kd/Ka) and is expressed as a molar concentration. A preferred method for determining the Kd of an antibody is by using surface plasmon resonance, preferably using a biosensor system, such as a Biacore system, or by using biolayer interferometry with the Octet BLI instrument.

The terms "inhibition" or "inhibit" or "reduction" or "reduce" or "neutralization" or "neutralize" refer to a decrease or cessation of any phenotypic characteristic (such as binding or a biological activity or function) or to the decrease or cessation in the incidence, degree, or likelihood of that characteristic. "Inhibition", "reduction" or "neutralization" needs not to be complete as long as it is detectable using an appropriate assay. In some embodiments, by "reduce" or "inhibit" or "neutralize" is meant the ability to cause a decrease of 20% or greater. In another embodiment, by "reduce" or "inhibit" or "neutralize" is meant the ability to cause a decrease of 50% or greater. In yet another embodiment, by "reduce" or "inhibit" or "neutralize" is meant the ability to cause an overall decrease of 75%, 85%, 90%, 95%, or greater.

The term "antagonistic" antibody as used herein refers to an antibody or antibody fragment that interacts with an antigen and partially or fully inhibits or neutralizes a biological activity or function or any other phenotypic characteristic of a target antigen.

A "wild-type" protein is a version or variant of the protein as it is found in nature. An amino acid sequence of a wildtype protein, e.g., a Fc region of a human IgG1 antibody, is the amino acid sequence of the protein as it occurs in nature. Due to allotypic differences, there can be more than one amino acid sequence for a wildtype protein. For example, there are several allotypes of naturally occurring human IGg1 heavy chain constant regions (see, e.g., Jeffries et al. (2009) mAbs 1:1).

The "Fc region" is used to define the C-terminal region of an immunoglobulin heavy chain. The Fc region of an immunoglobulin generally comprises two constant domains, a CH2 domain and a CH3 domain. Although the boundaries of the Fc region of an IgG heavy chain might vary slightly, the human IgG heavy chain Fc region is usually defined to extend from Cys226, or from Pro230, to the C-terminus of the heavy chain. However, the C-terminal lysine (Lys447) of the Fc region may or may not be present. Unless otherwise specified herein, numbering of amino acid residues in the Fc region is according to the EU numbering system, also called the EU index, as described in Kabat et al., Sequences of Proteins of Immunological Interest, 5th Ed. Public Health Service, National Institutes of Health, Bethesda, MD, 1991. Various Fc modifications are commonly used. For a review see for example Antibodies (2020) 9: 64. Silencing functions include (numbering according EU index) the LALA (L234A/L235A), the PA-LALA (L234A/L235A/P329A) and the PG-LALA (L234A/L235A/P329G) mutations, as well as the AEASS mutations (L234A/L235E/G237A/A330S/P331S). A preferred FC modification is PA-LALA. The mutation may also be a mutation which leads to a reduced binding to FcRn, thereby decreasing the in vivo half-life of the antibody. Such mutations include I253A, H310A, H435A and H435Q. Alternatively, the mutation may also be a mutation which leads to an increased binding to FcRn, thereby increasing the in vivo half-life of the antibody. Such mutations include T250Q/M428L, M252Y/S254T/T256E (YTE), H433K/N434F and M252Y/S254T/T256E/H433K/N434F.

EMBODIMENTS OF THE INVENTION

Polypeptides

The present disclosure relates to antibodies or antibody fragments that are specific for ActRIIB. In certain embodiments, the present disclosure relates to antibodies or antibody fragments that are specific for human ActRIIB.

In certain embodiments, the present disclosure relates to antibodies or antibody fragments that are specific for a polypeptide consisting of the amino acid sequence of SEQ ID No. 2. In certain embodiments, the present disclosure relates to antibodies or antibody fragments that are specific for a polypeptide comprising the amino acid sequence of SEQ ID No. 2.

In certain embodiments, the present disclosure relates to antibodies or antibody fragments that are specific for human ActRIIB and that are cross-reactive with ActRIIA. In certain embodiments, the present disclosure relates to antibodies or antibody fragments that are specific for a polypeptide consisting of the amino acid sequence of SEQ ID No. 2 and that are cross-reactive with a polypeptide consisting of the amino acid sequence of SEQ ID No. 2. In certain embodiments, the present disclosure relates to antibodies or antibody fragments that are specific for a polypeptide comprising the amino acid sequence of SEQ ID No. 2 and that are cross-reactive with a polypeptide comprising the amino acid sequence of SEQ ID No. 2.

In certain embodiments, the present disclosure relates to antibodies or antibody fragments that are specific for human ActRIIB and human ActRIIA. In certain embodiments, the present disclosure relates to antibodies or antibody fragments that are cross-reactive between human ActRIIB and human ActRIIA. In certain embodiments, the present disclosure relates to antibodies or antibody fragments that are specific for a polypeptide consisting of the amino acid sequence of SEQ ID No. 2 and a polypeptide consisting of the amino acid sequence of SEQ ID No. 1. In certain embodiments, the present disclosure relates to antibodies or antibody fragments that are specific for a polypeptide comprising the amino acid sequence of SEQ ID No. 2 and a polypeptide comprising the amino acid sequence of SEQ ID No. 1.

More specifically, the antibodies or antibody fragments disclosed herein are improved derivatives of bimagrumab. In certain embodiments, the present disclosure relates to antibodies or antibody fragments that are improved derivatives of an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8.

Bimagrumab, despite its clinical success, has several properties that can be improved. For example an improved affinity towards ActRIIA could increase potency and efficacy. A reduced unspecific binding could increase bioavailability after s.c. application as well as PK properties. An improvement of the biophysical properties could be important for a s.c. formulation. All these aspects aim to reduce the amount of antibody needed to obtain full efficacy over a prolonged period of time in order to enable the application of the antibody for high patient compliance and low cost of gods.

Therefore, in certain embodiments the present disclosure relates to an antibody or antibody fragment that is an improved derivatives of an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments the present disclosure relates to an antibody or antibody fragment that is an improved derivatives of an antibody or antibody fragment comprising a variable heavy chain of SEQ ID NO: 9 and a variable light chain of SEQ ID NO: 10.

In certain embodiments, said improvement is selected from one or more of the following properties:
 a) a higher affinity to human ActRIIA,
 b) less unspecific binding,
 c) an improved HIC score,
 d) an improved Heparin score,
 e) a lower IC95 in a myostatin inhibition assay, or
 f) a lower IC95 in a activin inhibition assay.

In certain embodiments, the present disclosure relates to an antibody or antibody fragment specific for human ActRIIB, wherein said antibody or antibody fragment has a higher affinity to human ActRIIA than an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8.

In certain embodiments, the present disclosure relates to antibody or antibody fragment specific for human ActRIIB, wherein said antibody or antibody fragment has one or more of the following additional properties compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8:
 a) less unspecific binding,
 b) an improved HIC score,
 c) an improved Heparin score,
 d) a lower IC95 in a myostatin inhibition assay,
 e) a lower IC95 in a activin inhibition assay, or
 f) a reduced viscosity.

In certain embodiments, the present disclosure relates to an antibody or antibody fragment specific for human ActRIIB, wherein said antibody or antibody fragment has a higher affinity to human ActRIIA compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has a higher affinity to human ActRIIA compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has less unspecific binding compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has less unspecific binding compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has an improved HIC score compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has an improved HIC score compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has an improved Heparin score compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has an improved Heparin score compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has a lower IC50 in a myostatin inhibition assay compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has a lower IC50 in a myostatin inhibition assay compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has a lower IC90 in a myostatin inhibition assay compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has a lower IC50 in a myostatinn inhibition assay compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has a lower IC95 in a myostatin inhibition assay compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has a lower IC50 in a myostatin inhibition assay compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has a lower IC50 in a activin inhibition assay compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has a lower IC50 in an activin inhibition assay compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has a lower IC90 in a activin inhibition assay compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has a lower IC50 in an activin inhibition assay compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment has a lower IC95 in a activin inhibition assay compared to an antibody or antibody fragment comprising a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 7 and the LCDR3 region of SEQ ID NO: 8. In certain embodiments, the present disclosure relates to an antibody or antibody fragment specific for human ActRIIB, wherein said antibody or antibody fragment has a lower IC50 in an activin inhibition assay compared to an antibody or antibody fragment comprising a variable heavy chain of SEQ ID NO: 9 and a variable light chain of SEQ ID NO: 10. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises
  a) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14,
  b) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18,
  c) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14,
  d) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14,
  e) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18,
  f) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27,
  g) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14,
  h) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34,
  i) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, or
  j) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14.

In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises
  a) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14,
  b) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18,
  c) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14,
  d) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14,
  e) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18,
  f) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27,
  g) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14,
  h) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34,
  i) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14,
  j) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14,
  k) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14, or
  l) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14.

In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises
  a) a variable heavy chain of SEQ ID NO: 12 and a variable light chain of SEQ ID NO: 15,
  b) a variable heavy chain of SEQ ID NO: 16 and a variable light chain of SEQ ID NO: 19,
  c) a variable heavy chain of SEQ ID NO: 16 and a variable light chain of SEQ ID NO: 21,
  d) a variable heavy chain of SEQ ID NO: 16 and a variable light chain of SEQ ID NO: 23,
  e) a variable heavy chain of SEQ ID NO: 24 and a variable light chain of SEQ ID NO: 25,
  f) a variable heavy chain of SEQ ID NO: 16 and a variable light chain of SEQ ID NO: 28,
  g) a variable heavy chain of SEQ ID NO: 16 and a variable light chain of SEQ ID NO: 31,
  h) a variable heavy chain of SEQ ID NO: 32 and a variable light chain of SEQ ID NO: 35, i) a variable heavy chain of SEQ ID NO: 36 and a variable light chain of SEQ ID NO: 15,
j) a variable heavy chain of SEQ ID NO: 37 and a variable light chain of SEQ ID NO: 21,
k) a variable heavy chain of SEQ ID NO: 37 and a variable light chain of SEQ ID NO: 23,
l) a variable heavy chain of SEQ ID NO: 38 and a variable light chain of SEQ ID NO: 23,
m) a variable heavy chain of SEQ ID NO: 37 and a variable light chain of SEQ ID NO: 39,
n) a variable heavy chain of SEQ ID NO: 37 and a variable light chain of SEQ ID NO: 40, or
o) a variable heavy chain of SEQ ID NO: 37 and a variable light chain of SEQ ID NO: 42. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 12 and a variable light chain of SEQ ID NO: 15. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 16 and a variable light chain of SEQ ID NO: 19. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 16 and a variable light chain of SEQ ID NO: 21. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 16 and a variable light chain of SEQ ID NO: 23. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 24 and a variable light chain of SEQ ID NO: 25. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 16 and a variable light chain of SEQ ID NO: 28. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 16 and a variable light chain of SEQ ID NO: 31. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 32 and a variable light chain of SEQ ID NO: 35. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 36 and a variable light chain of SEQ ID NO: 15. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 37 and a variable light chain of SEQ ID NO: 21. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 37 and a variable light chain of SEQ ID NO: 23. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 38 and a variable light chain of SEQ ID NO: 23. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 37 and a variable light chain of SEQ ID NO: 39. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain of SEQ ID NO: 37 and a variable light chain of SEQ ID NO: 40.

In certain embodiments, the present disclosure relates to an antibody or antibody fragment specific for human ActRIIB, wherein said antibody or antibody fragment comprises a variable heavy chain of SEQ ID NO: 37 and a variable light chain of SEQ ID NO: 42. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises the six CDRs of any one of the antibodies disclosed in Tables 2, 7, 8, 9 or 12. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises the six CDRs of any one of the antibodies disclosed in Tables 2 or 12. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises the six CDRs of any one of the antibodies disclosed in Table 12. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises the six CDRs as defined by Kabat of any one of the antibodies disclosed in Table 12. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain and a variable light chain of any one of the antibodies disclosed in Tables 2, 7, 8, 9 or 12. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain and a variable light chain of any one of the antibodies disclosed in Tables 2 or 12. In certain embodiments, said antibody or antibody fragment binds to human ActRIIA and human ActRIIB.

In certain embodiments, the present disclosure relates to an antibody or antibody fragment specific for human ActRIIB, wherein said antibody or antibody fragment comprises a variable heavy chain and a variable light chain of any one of the antibodies disclosed in Table 12. In certain embodiments, said antibody or antibody fragment binds to human ActRIIA and human ActRIIB.

In certain embodiments, the present disclosure relates to an antibody or antigen binding fragment thereof which binds to ActRIIB comprising:
  a) a heavy chain variable region CDR1 comprising the amino acid sequence of SEQ ID NO: 3;
  b) a heavy chain variable region CDR2 comprising the amino acid sequence of SEQ ID NO: 11;
  c) a heavy chain variable region CDR3 comprising the amino acid sequence of SEQ ID NO: 5;
  d) a light chain variable region CDR1 comprising the amino acid sequence of SEQ ID NO: 22;
  e) a light chain variable region CDR2 comprising the amino acid sequence of SEQ ID NO: 13 and
  f) a light chain variable region CDR3 comprising the amino acid sequence of SEQ ID NO: 14.

In certain embodiments, the present disclosure relates to an antibody or antigen binding fragment thereof which binds to ActRIIA or ActRIIB comprising:
  a) a heavy chain variable region CDR1 comprising the amino acid sequence of SEQ ID NO: 3;
  b) a heavy chain variable region CDR2 comprising the amino acid sequence of SEQ ID NO: 11;
  c) a heavy chain variable region CDR3 comprising the amino acid sequence of SEQ ID NO: 5;
  d) a light chain variable region CDR1 comprising the amino acid sequence of SEQ ID NO: 22;
  e) a light chain variable region CDR2 comprising the amino acid sequence of SEQ ID NO: 13 and
  f) a light chain variable region CDR3 comprising the amino acid sequence of SEQ ID NO: 14.

In certain embodiments, the present disclosure relates to an antibody or antigen binding fragment thereof which binds to ActRIIA and ActRIIB comprising:
  a) a heavy chain variable region CDR1 comprising the amino acid sequence of SEQ ID NO: 3;
  b) a heavy chain variable region CDR2 comprising the amino acid sequence of SEQ ID NO: 11;
  c) a heavy chain variable region CDR3 comprising the amino acid sequence of SEQ ID NO: 5;
  d) a light chain variable region CDR1 comprising the amino acid sequence of SEQ ID NO: 22;
  e) a light chain variable region CDR2 comprising the amino acid sequence of SEQ ID NO: 13 and
  f) a light chain variable region CDR3 comprising the amino acid sequence of SEQ ID NO: 14.

In certain embodiments, the present disclosure relates to an antibody or antigen binding fragment thereof which binds to ActRIIB:
  a) the heavy chain variable region CDR1 having the amino acid sequence of SEQ ID NO: 3;
  b) the heavy chain variable region CDR2 having the amino acid sequence of SEQ ID NO: 11;
  c) the heavy chain variable region CDR3 having the amino acid sequence of SEQ ID NO: 5;
  d) the light chain variable region CDR1 having the amino acid sequence of SEQ ID NO: 22;
  e) the light chain variable region CDR2 having the amino acid sequence of SEQ ID NO: 13; and
  f) the light chain variable region CDR3 having the amino acid sequence of SEQ ID NO: 14.

In certain embodiments, the present disclosure relates to antibody or antigen binding fragment thereof which binds to ActRIIA or ActRIIB:
  a) the heavy chain variable region CDR1 having the amino acid sequence of SEQ ID NO: 3;
  b) the heavy chain variable region CDR2 having the amino acid sequence of SEQ ID NO: 11;
  c) the heavy chain variable region CDR3 having the amino acid sequence of SEQ ID NO: 5;
  d) the light chain variable region CDR1 having the amino acid sequence of SEQ ID NO: 22;
  e) the light chain variable region CDR2 having the amino acid sequence of SEQ ID NO: 13; and
  f) the light chain variable region CDR3 having the amino acid sequence of SEQ ID NO: 14.

In certain embodiments, the present disclosure relates to an antibody or antigen binding fragment thereof which binds to ActRIIA and ActRIIB:
  a) the heavy chain variable region CDR1 having the amino acid sequence of SEQ ID NO: 3;
  b) the heavy chain variable region CDR2 having the amino acid sequence of SEQ ID NO: 11;
  c) the heavy chain variable region CDR3 having the amino acid sequence of SEQ ID NO: 5;
  d) the light chain variable region CDR1 having the amino acid sequence of SEQ ID NO: 22;
  e) the light chain variable region CDR2 having the amino acid sequence of SEQ ID NO: 13; and
  f) the light chain variable region CDR3 having the amino acid sequence of SEQ ID NO: 14.

In certain embodiments, the present disclosure relates to an antibody or antigen binding fragment thereof which binds to ActRIIB comprising a heavy chain variable region having the amino acid sequence of SEQ ID NO: 16, and a light chain variable region having the amino acids sequence of SEQ ID NO: 23.

In certain embodiments, the present disclosure relates to an antibody or antigen binding fragment thereof which binds to ActRIIA or ActRIIB comprising a heavy chain variable region having the amino acid sequence of SEQ ID NO: 16, and a light chain variable region having the amino acids sequence of SEQ ID NO: 23.

In certain embodiments, the present disclosure relates to an antibody or antigen binding fragment thereof which binds to ActRIIA and ActRIIB comprising a heavy chain variable region having the amino acid sequence of SEQ ID NO: 16, and a light chain variable region having the amino acids sequence of SEQ ID NO: 23.

In certain embodiments, the present disclosure relates to an antibody or antigen binding fragment thereof which binds to ActRIIB comprising:
  a) a heavy chain variable region CDR1 comprising the amino acid sequence of SEQ ID NO: 3;
  b) a heavy chain variable region CDR2 comprising the amino acid sequence of SEQ ID NO: 11;
  c) a heavy chain variable region CDR3 comprising the amino acid sequence of SEQ ID NO: 5;
  d) a light chain variable region CDR1 comprising the amino acid sequence of SEQ ID NO: 29;
  e) a light chain variable region CDR2 comprising the amino acid sequence of SEQ ID NO: 30 and
  f) a light chain variable region CDR3 comprising the amino acid sequence of SEQ ID NO: 14.

In certain embodiments, the present disclosure relates to an antibody or antigen binding fragment thereof which binds to ActRIIA or ActRIIB comprising:
  a) a heavy chain variable region CDR1 comprising the amino acid sequence of SEQ ID NO: 3;
  b) a heavy chain variable region CDR2 comprising the amino acid sequence of SEQ ID NO: 11;
  c) a heavy chain variable region CDR3 comprising the amino acid sequence of SEQ ID NO: 5;
  d) a light chain variable region CDR1 comprising the amino acid sequence of SEQ ID NO: 29;
  e) a light chain variable region CDR2 comprising the amino acid sequence of SEQ ID NO: 30 and
  f) a light chain variable region CDR3 comprising the amino acid sequence of SEQ ID NO: 14.

In certain embodiments, the present disclosure relates to an antibody or antigen binding fragment thereof which binds to ActRIIA and ActRIIB comprising:
  a) a heavy chain variable region CDR1 comprising the amino acid sequence of SEQ ID NO: 3;
  b) a heavy chain variable region CDR2 comprising the amino acid sequence of SEQ ID NO: 11;
  c) a heavy chain variable region CDR3 comprising the amino acid sequence of SEQ ID NO: 5;
  d) a light chain variable region CDR1 comprising the amino acid sequence of SEQ ID NO: 29;
  e) a light chain variable region CDR2 comprising the amino acid sequence of SEQ ID NO: 30 and
  f) a light chain variable region CDR3 comprising the amino acid sequence of SEQ ID NO: 14.

In certain embodiments, the present disclosure relates to an antibody or antigen binding fragment thereof which binds to ActRIIB:
  a) the heavy chain variable region CDR1 having the amino acid sequence of SEQ ID NO: 3;
  b) the heavy chain variable region CDR2 having the amino acid sequence of SEQ ID NO: 11;
  c) the heavy chain variable region CDR3 having the amino acid sequence of SEQ ID NO: 5;
  d) the light chain variable region CDR1 having the amino acid sequence of SEQ ID NO: 29;
  e) the light chain variable region CDR2 having the amino acid sequence of SEQ ID NO: 30; and
  f) the light chain variable region CDR3 having the amino acid sequence of SEQ ID NO: 14.

In certain embodiments, the present disclosure relates to an antibody or antigen binding fragment thereof which binds to ActRIIA or ActRIIB:
  a) the heavy chain variable region CDR1 having the amino acid sequence of SEQ ID NO: 3;
  b) the heavy chain variable region CDR2 having the amino acid sequence of SEQ ID NO: 11;
  c) the heavy chain variable region CDR3 having the amino acid sequence of SEQ ID NO: 5;
  d) the light chain variable region CDR1 having the amino acid sequence of SEQ ID NO: 29;
  e) the light chain variable region CDR2 having the amino acid sequence of SEQ ID NO: 30; and
  f) the light chain variable region CDR3 having the amino acid sequence of SEQ ID NO: 14.

In certain embodiments, the present disclosure relates to an antibody or antigen binding fragment thereof which binds to ActRIIA and ActRIIB:
  a) the heavy chain variable region CDR1 having the amino acid sequence of SEQ ID NO: 3;
  b) the heavy chain variable region CDR2 having the amino acid sequence of SEQ ID NO: 11;
  c) the heavy chain variable region CDR3 having the amino acid sequence of SEQ ID NO: 5;
  d) the light chain variable region CDR1 having the amino acid sequence of SEQ ID NO: 29;
  e) the light chain variable region CDR2 having the amino acid sequence of SEQ ID NO: 30; and
  f) the light chain variable region CDR3 having the amino acid sequence of SEQ ID NO: 14.

In certain embodiments, the present disclosure relates to an antibody or antigen binding fragment thereof which binds to ActRIIB comprising a heavy chain variable region having the amino acid sequence of SEQ ID NO: 16, and a light chain variable region having the amino acids sequence of SEQ ID NO: 31.

In certain embodiments, the present disclosure relates to an antibody or antigen binding fragment thereof which binds to ActRIIA or ActRIIB comprising a heavy chain variable region having the amino acid sequence of SEQ ID NO: 16, and a light chain variable region having the amino acids sequence of SEQ ID NO: 31.

In certain embodiments, the present disclosure relates to an antibody or antigen binding fragment thereof which binds to ActRIIA and ActRIIB comprising a heavy chain variable region having the amino acid sequence of SEQ ID NO: 16, and a light chain variable region having the amino acids sequence of SEQ ID NO: 31.

In certain embodiments, the present disclosure relates to an antibody or antigen binding fragment thereof which binds to ActRIIB comprising:
  a) a heavy chain variable region CDR1 comprising the amino acid sequence of SEQ ID NO: 3;
  b) a heavy chain variable region CDR2 comprising the amino acid sequence of SEQ ID NO: 4;
  c) a heavy chain variable region CDR3 comprising the amino acid sequence of SEQ ID NO: 5;
  d) a light chain variable region CDR1 comprising the amino acid sequence of SEQ ID NO: 33;
  e) a light chain variable region CDR2 comprising the amino acid sequence of SEQ ID NO: 13 and f) a light chain variable region CDR3 comprising the amino acid sequence of SEQ ID NO: 34.

In certain embodiments, the present disclosure relates to an antibody or antigen binding fragment thereof which binds to ActRIIA or ActRIIB comprising:
a) a heavy chain variable region CDR1 comprising the amino acid sequence of SEQ ID NO: 3;
b) a heavy chain variable region CDR2 comprising the amino acid sequence of SEQ ID NO: 4;
c) a heavy chain variable region CDR3 comprising the amino acid sequence of SEQ ID NO: 5;
d) a light chain variable region CDR1 comprising the amino acid sequence of SEQ ID NO: 33;
e) a light chain variable region CDR2 comprising the amino acid sequence of SEQ ID NO: 13 and
f) a light chain variable region CDR3 comprising the amino acid sequence of SEQ ID NO: 34.

In certain embodiments, the present disclosure relates to an antibody or antigen binding fragment thereof which binds to ActRII and ActRIIB comprising:
a) a heavy chain variable region CDR1 comprising the amino acid sequence of SEQ ID NO: 3;
b) a heavy chain variable region CDR2 comprising the amino acid sequence of SEQ ID NO: 4;
c) a heavy chain variable region CDR3 comprising the amino acid sequence of SEQ ID NO: 5;
d) a light chain variable region CDR1 comprising the amino acid sequence of SEQ ID NO: 33;
e) a light chain variable region CDR2 comprising the amino acid sequence of SEQ ID NO: 13 and
f) a light chain variable region CDR3 comprising the amino acid sequence of SEQ ID NO: 34.

In certain embodiments, the present disclosure relates to an antibody or antigen binding fragment thereof which binds to ActRIIB:
a) the heavy chain variable region CDR1 having the amino acid sequence of SEQ ID NO: 3;
b) the heavy chain variable region CDR2 having the amino acid sequence of SEQ ID NO: 4;
c) the heavy chain variable region CDR3 having the amino acid sequence of SEQ ID NO: 5;
d) the light chain variable region CDR1 having the amino acid sequence of SEQ ID NO: 33;
e) the light chain variable region CDR2 having the amino acid sequence of SEQ ID NO: 13; and
f) the light chain variable region CDR3 having the amino acid sequence of SEQ ID NO: 34.

In certain embodiments, the present disclosure relates to an antibody or antigen binding fragment thereof which binds to ActRIIA or ActRIIB:
a) the heavy chain variable region CDR1 having the amino acid sequence of SEQ ID NO: 3;
b) the heavy chain variable region CDR2 having the amino acid sequence of SEQ ID NO: 4;
c) the heavy chain variable region CDR3 having the amino acid sequence of SEQ ID NO: 5;
d) the light chain variable region CDR1 having the amino acid sequence of SEQ ID NO: 33;
e) the light chain variable region CDR2 having the amino acid sequence of SEQ ID NO: 13; and
f) the light chain variable region CDR3 having the amino acid sequence of SEQ ID NO: 34.

In certain embodiments, the present disclosure relates to an antibody or antigen binding fragment thereof which binds to ActRIIA and ActRIIB:
a) the heavy chain variable region CDR1 having the amino acid sequence of SEQ ID NO: 3;
b) the heavy chain variable region CDR2 having the amino acid sequence of SEQ ID NO: 4;
c) the heavy chain variable region CDR3 having the amino acid sequence of SEQ ID NO: 5;
d) the light chain variable region CDR1 having the amino acid sequence of SEQ ID NO: 33;
e) the light chain variable region CDR2 having the amino acid sequence of SEQ ID NO: 13; and
f) the light chain variable region CDR3 having the amino acid sequence of SEQ ID NO: 34.

In certain embodiments, the present disclosure relates to an antibody or antigen binding fragment thereof which binds to ActRIIB comprising a heavy chain variable region having the amino acid sequence of SEQ ID NO: 32, and a light chain variable region having the amino acids sequence of SEQ ID NO: 35.

In certain embodiments, the present disclosure relates to an antibody or antigen binding fragment thereof which binds to ActRIIA or ActRIIB comprising a heavy chain variable region having the amino acid sequence of SEQ ID NO: 32, and a light chain variable region having the amino acids sequence of SEQ ID NO: 35.

In certain embodiments, the present disclosure relates to an antibody or antigen binding fragment thereof which binds to ActRIIA and ActRIIB comprising a heavy chain variable region having the amino acid sequence of SEQ ID NO: 32, and a light chain variable region having the amino acids sequence of SEQ ID NO: 35.

In certain embodiments, the present disclosure relates to an antibody or antibody fragment specific for human ActRIIB, wherein said antibody or antibody fragment is a monoclonal antibody or antibody fragment.

In certain embodiments, the present disclosure relates to an antibody or antibody fragment specific for human ActRIIB, wherein said antibody or antibody fragment is a recombinant antibody or antibody fragment.

In certain embodiments, the present disclosure relates to an antibody specific for human ActRIIB, wherein said antibody is of the IgG isotype.

In certain embodiments, the present disclosure relates to an antibody specific for human ActRIIB, wherein said antibody is of the lgG1 class.

In certain embodiments, the present disclosure relates to an antibody specific for human ActRIIB, wherein said antibody is of the human lgG1 class.

In certain embodiments, the present disclosure relates to an antibody or antibody fragment specific for human ActRIIB, wherein said antibody or antibody fragment is an isolated antibody or antibody fragment.

The antibody or antibody fragment according to the present disclosure may or may not be fused to one or more other amino acid residues, polypeptides or moieties. Such a fusion protein may be prepared in any suitable manner, including genetically or chemically approaches. Said linked moieties may contain secretory or leader sequences, sequences that aid detection, expression, separation or purification, or sequences that confer to increased protein stability, for example, during recombinant production. Non-limiting examples of potential moieties include beta-galactosidase, glutathione-S-transferase, luciferase, a T7 polymerase fragment, a secretion signal peptide, an antibody or antibody fragment, a toxin, a cytokine, a chemokine, a reporter enzyme, a moiety being capable of binding a metal ion like a poly-histidine tag, a tag suitable for detection and/or purification, a homo- or hetero-association domain, a moiety which increases solubility of a protein, or a moiety which comprises an enzymatic cleavage site.

The antibodies or antibody fragments specific for ActRIIB may also be conjugated or fused to an additional pharmaceutical active moiety. Respective technologies and pharmaceutical active moieties are known to the person skilled in the art.

Effector Function

The Fc region of an immunoglobulin generally confers to the favorable pharmacokinetic properties of antibodies, such as prolonged half-life in serum and to the ability to induce effector function via binding to Fc receptors expressed on cells. On the other hand, binding to Fc receptors might also results in an undesirable activation of certain cell surface receptors leading to unwanted cytokine release and severe side effects upon systemic administration.

Accordingly, for certain therapeutic situations, it is desirable to reduce or abolish the normal binding of the wild-type Fc region of an antibody, such as of an wild-type IgG Fc region to one or more or all of Fc receptors and/or binding to a complement component, such as C1q in order to reduce or abolish the ability of the antibody to induce effector function. For instance, it may be desirable to reduce or abolish the binding of the Fc region of an antibody to one or more or all of the Fcγ receptors, such as: FcγRI, FcγRIIa, FcγRIIb, FcγRIIIa. Effector function can include, but is not limited to, one or more of the following: complement dependent cytotoxicity (CDC), antibody-dependent cell-mediated cytotoxicity (ADCC), antibody-dependent cellular phagocytosis (ADCP), cytokine secretion, immune complex-mediated antigen uptake by antigen-presenting cells, binding to NK cells, binding to macrophages, binding to monocytes, binding to polymorphonuclear cells, direct signaling inducing apoptosis, crosslinking of target-bound antibodies, dendritic cell maturation, or T cell priming.

A reduced or abolished binding of an Fc region to an Fc receptor and/or to C1q is typically achieved by mutating a wild-type Fc region, such as of an lgG1 Fc region, more particular a human lgG1 Fc region, resulting in a variant or engineered Fc region of said wild-type Fc region, e.g., a variant human lgG1 Fc region. Substitutions that result in reduced binding can be useful. For reducing or abolishing the binding properties of an Fc region to an Fc receptor, non-conservative amino acid substitutions, i.e., replacing one amino acid with another amino acid having different structural and/or chemical properties, are preferred.

Accordingly, in an embodiment, the antibody or antibody fragment specific for human ActRIIB according to the present disclosure comprises a variant Fc region having a reduced or abolished binding to an Fc receptor and/or to C1q when compared to the wild-type Fc region. In one such embodiment, the antibody or antibody fragment according to the present disclosure comprises a variant Fc region that reduces or abolishes the ability of the antibody to induce effector function. In a further embodiment, the antibody or antibody fragment according to the present disclosure does not substantially induce effector function.

In certain embodiments, the effector function is one or more selected from the group consisting of CDC, ADCC and ADCP. In an embodiment, the effector function is ADCC. In an embodiment, the effector function is CDC. In an embodiment, the effector function is ADCP. In an embodiment, the antibody or antibody fragment according to the present disclosure does not substantially induce ADCC and/or CDC and/or ADCP. In an embodiment, the antibody or antibody fragment according to the present disclosure does not induce ADCC or ADCP in vitro.

In an embodiment, the variant Fc region of the antibody or antibody fragment according to the present disclosure comprises one or more amino acid substitutions that reduce or abolish the binding of the variant Fc region to one or more Fc receptors and/or to C1q when compared to the wild-type Fc region. In an embodiment, the variant Fc region of the antibody or antibody fragment according to the present disclosure comprises one or more amino acid substitutions that reduce or abolish the ability of the antibody to induce effector function when compared to the wild-type Fc region. In an embodiment, the one or more amino acid substitutions may reduce the binding affinity of the variant Fc region for one or more Fc receptors and/or to C1q by at least 2-fold, at least 5-fold, at least 10-fold, at least 20-fold or even at least 50-fold when compared to the wild-type Fc region. In alternative embodiments, the one or more amino acid substitutions may reduce the ability of the antibody or antibody fragment according to the present disclosure to induce effector function by at least 2-fold, at least 5-fold, at least 10-fold, at least 20-fold or even at least 50-fold when compared to the wild-type Fc region.

In an embodiment, the variant Fc region of the antibody or antibody fragment according to the present disclosure does not substantially bind to one or more Fc receptors and/or C1q. In an embodiment, the variant Fc region of the antibody according to the present disclosure does substantially abolish the ability of said antibody to induce effector function. In an embodiment, the antibody or antibody fragment according to the present disclosure does not substantially induce effector function. In an embodiment, said effect function is ADCC and/or ADCP and/or CDC. In an embodiment, the antibody or antibody fragment according to the present disclosure does not substantially induce effector function meaning that the level of induced effector function is not significantly above the background as measured in the absence of said antibody.

In an embodiment, the Fc receptor is a human Fc receptor. In an embodiment, the Fc receptor is an Fcγ receptor. In an embodiment, the Fc receptor is a human FcγRIIIa, FcγRI, FcγRIIa and/or FcγRIIb.

In an embodiment, the antibody or antibody fragment according to the present disclosure comprises a variant human lgG1 Fc region, which comprises one or more amino acid substitutions compared to the wild-type human lgG1 Fc region. In an embodiment, that one or more amino acid substitutions reduce or abolish the binding of the variant Fc region to an Fc receptor and/or to C1q and/or reduces the ability of said antibody to induce effector function when compared to the wild-type Fc region.

Various Fc modifications are commonly used. For a review see for example Antibodies (2020) 9: 64. Silencing functions include (numbering according EU index) the LALA (L234A/L235A), the PA-LALA (L234A/L235A/P329A) and the PG-LALA (L234A/L235A/P329G) mutations, as well as the AEASS mutations (L234A/L235E/G237A/A330S/P331S).

In certain embodiments, the present disclosure relates to an antibody specific for human ActRIIB, wherein said antibody comprises a silencing modification in the Fc region.

In certain embodiments, the present disclosure relates to an antibody specific for human ActRIIB, wherein said antibody comprises a silencing modification in the Fc region, wherein said silencing modification is a LALA, PA-LALA, a PG-LALA or an AEASS mutation.

In certain embodiments, the present disclosure relates to an antibody specific for human ActRIIB, wherein said antibody comprises a silencing modification in the Fc region, wherein said silencing modification is a PA-LALA (L234A/L235A/P329A) modification.

In certain embodiments, the present disclosure relates to an antibody specific for human ActRIIB, wherein said antibody comprises a silencing modification in the Fc region, wherein said silencing modification is a PG-LALA (L234A/L235A/P329G) modification.

In certain embodiments, the present disclosure relates to an antibody specific for human ActRIIB, wherein said antibody comprises a silencing modification in the Fc region, wherein said silencing modification is a AEASS (L234A/L235E/G237A/A330S/P331S) modification.

In certain embodiments, the present disclosure relates to antibodies that are specific for human ActRIIB, wherein said antibodies have mutations that lead to a reduced binding to FcRn, thereby decreasing the in vivo half-life of the antibody. In certain embodiments, the present disclosure relates to antibodies that are specific for human ActRIIB, wherein said antibodies comprise a Fc region with a I253A mutation (numbering according EU index). In certain embodiments, the present disclosure relates to antibodies that are specific for human ActRIIB, wherein said antibodies comprise a Fc region with a H310A mutation (numbering according EU index). In certain embodiments, the present disclosure relates to antibodies that are specific for human ActRIIB, wherein said antibodies comprise a Fc region with a H435A mutation (numbering according EU index). In certain embodiments, the present disclosure relates to antibodies that are specific for human ActRIIB, wherein said antibodies comprise a Fc region with a H435Q mutation (numbering according EU index).

In certain embodiments, the present disclosure relates to antibodies that are specific for human ActRIIB, wherein said have mutations that lead to a increased binding to FcRn, thereby increasing the in vivo half-life of the antibody. In certain embodiments, the present disclosure relates to antibodies that are specific for human ActRIIB, wherein said antibodies comprise a T250Q/M428L mutation in the Fc region (numbering according EU index). In certain embodiments, the present disclosure relates to antibodies that are specific for human ActRIIB, wherein said antibodies comprise a M252Y/S254T/T256E (YTE) mutation in the Fc region (numbering according EU index). In certain embodiments, the present disclosure relates to antibodies that are specific for human ActRIIB, wherein said antibodies comprise a H433K/N434F mutation in the Fc region (numbering according EU index). In certain embodiments, the present disclosure relates to antibodies that are specific for human ActRIIB, wherein said antibodies comprise a M252Y/S254T/T256E/H433K/N434F mutation in the Fc region (numbering according EU index).

In certain embodiments, the present disclosure relates to an antibody specific for human ActRIIB, wherein said antibody or antibody fragment comprises
  a) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14,
  b) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18,
  c) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14,
  d) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14,
  e) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18,
  f) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27,
  g) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14,
  h) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34,
  i) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, or
  j) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14,
wherein said antibody comprises a M252Y/S254T/T256E (YTE) mutation in the Fc region (numbering according EU index). In certain embodiments, said antibody or antibody fragment binds to human ActRIIA and human ActRIIB.

In certain embodiments, the present disclosure relates to an antibody specific for human ActRIIB, wherein said antibody or antibody fragment comprises
  a) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14,
  b) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18,
  c) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14,
  d) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14,
  e) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18, f) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27, g) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14, h) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34, i) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, j) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14, k) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14, or l) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14, wherein said antibody comprises a M252Y/S254T/T256E (YTE) mutation in the Fc region (numbering according EU index). In certain embodiments, said antibody or antibody fragment binds to human ActRIIA and human ActRIIB.

In certain embodiments, the present disclosure relates to an antibody specific for human ActRIIB, wherein said antibody or antibody fragment comprises a) a variable heavy chain of SEQ ID NO: 12 and a variable light chain of SEQ ID NO: 15, b) a variable heavy chain of SEQ ID NO: 16 and a variable light chain of SEQ ID NO: 19, c) a variable heavy chain of SEQ ID NO: 16 and a variable light chain of SEQ ID NO: 21, d) a variable heavy chain of SEQ ID NO: 16 and a variable light chain of SEQ ID NO: 23, e) a variable heavy chain of SEQ ID NO: 24 and a variable light chain of SEQ ID NO: 25, f) a variable heavy chain of SEQ ID NO: 16 and a variable light chain of SEQ ID NO: 28, g) a variable heavy chain of SEQ ID NO: 16 and a variable light chain of SEQ ID NO: 31, h) a variable heavy chain of SEQ ID NO: 32 and a variable light chain of SEQ ID NO: 35, i) a variable heavy chain of SEQ ID NO: 36 and a variable light chain of SEQ ID NO: 15, j) a variable heavy chain of SEQ ID NO: 37 and a variable light chain of SEQ ID NO: 21, k) a variable heavy chain of SEQ ID NO: 37 and a variable light chain of SEQ ID NO: 23, l) a variable heavy chain of SEQ ID NO: 38 and a variable light chain of SEQ ID NO: 23, m) a variable heavy chain of SEQ ID NO: 37 and a variable light chain of SEQ ID NO: 39, n) a variable heavy chain of SEQ ID NO: 37 and a variable light chain of SEQ ID NO: 40, or o) a variable heavy chain of SEQ ID NO: 37 and a variable light chain of SEQ ID NO: 42, wherein said antibody comprises a M252Y/S254T/T256E (YTE) mutation in the Fc region (numbering according EU index). In certain embodiments, said antibody or antibody fragment binds to human ActRIIA and human ActRIIB.

Nucleic Acids

In an embodiment, the present disclosure relates to a nucleic acid composition comprising a nucleic acid sequence or a plurality of nucleic acid sequences encoding an antibody or antibody fragment specific for human ActRIIB of the present disclosure.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises a) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, b) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18, c) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14, d) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14, e) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18, f) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27, g) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14, h) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34, i) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, or j) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14. In certain embodiments, said antibody or antibody fragment binds to human ActRIIA and human ActRIIB.

In another embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises a) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, b) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 17, the LCDR2 region of SEQ ID NO: 13 and the LCDR3 region of SEQ ID NO: 18, c) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14, d) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14, e) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 18, f) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 26, the LCDR2 region of SEQ ID NO: 13 and the LCDR3 region of SEQ ID NO: 27, g) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 29, the LCDR2 region of SEQ ID NO: 30 and the LCDR3 region of SEQ ID NO: 14, h) a HCDR1 region of SEQ ID NO: 3, a HCDR2 region of SEQ ID NO: 4, a HCDR3 region of SEQ ID NO: 5 and a variable light chain comprising, the LCDR1 region of SEQ ID NO: 33, the LCDR2 region of SEQ ID NO: 13 and the LCDR3 region of SEQ ID NO: 34, i) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 13 and the LCDR3 region of SEQ ID NO: 14, j) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 6, the LCDR2 region of SEQ ID NO: 20 and the LCDR3 region of SEQ ID NO: 14, k) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 13 and the LCDR3 region of SEQ ID NO: 14, or l) a HCDR1 region of SEQ ID NO: 3, a HCDR2 region of SEQ ID NO: 11, a HCDR3 region of SEQ ID NO: 5 and a variable light chain comprising, the LCDR1 region of SEQ ID NO: 22, the LCDR2 region of SEQ ID NO: 41 and the LCDR3 region of SEQ ID NO: 14. In certain embodiments, said antibody or antibody fragment binds to human ActRIIA and human ActRIIB.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises a) a variable heavy chain of SEQ ID NO: 12 and a variable light chain of SEQ ID NO: 15, b) a variable heavy chain of SEQ ID NO: 16 and a variable light chain of SEQ ID NO: 19, c) a variable heavy chain of SEQ ID NO: 16 and a variable light chain of SEQ ID NO: 21, d) a variable heavy chain of SEQ ID NO: 16 and a variable light chain of SEQ ID NO: 23, e) a variable heavy chain of SEQ ID NO: 24 and a variable light chain of SEQ ID NO: 25, f) a variable heavy chain of SEQ ID NO: 16 and a variable light chain of SEQ ID NO: 28, g) a variable heavy chain of SEQ ID NO: 16 and a variable light chain of SEQ ID NO: 31, h) a variable heavy chain of SEQ ID NO: 32 and a variable light chain of SEQ ID NO: 35, i) a variable heavy chain of SEQ ID NO: 36 and a variable light chain of SEQ ID NO: 15, j) a variable heavy chain of SEQ ID NO: 37 and a variable light chain of SEQ ID NO: 21, k) a variable heavy chain of SEQ ID NO: 37 and a variable light chain of SEQ ID NO: 23, l) a variable heavy chain of SEQ ID NO: 38 and a variable light chain of SEQ ID NO: 23, m) a variable heavy chain of SEQ ID NO: 37 and a variable light chain of SEQ ID NO: 39, n) a variable heavy chain of SEQ ID NO: 37 and a variable light chain of SEQ ID NO: 40, or o) a variable heavy chain of SEQ ID NO: 37 and a variable light chain of SEQ ID NO: 42. In certain embodiments, said antibody or antibody fragment binds to human ActRIIA and human ActRIIB.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises 6 six CDRs of any one of the antibodies disclosed in Tables 2, 7, 8, 9 or 12. In certain embodiments, said antibody or antibody fragment binds to human ActRIIA and human ActRIIB.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises 6 six CDRs of any one of the antibodies disclosed in Tables 2 or 12. In certain embodiments, said antibody or antibody fragment binds to human ActRIIA and human ActRIIB.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises 6 six CDRs of any one of the antibodies disclosed in Table 12. In certain embodiments, said antibody or antibody fragment binds to human ActRIIA and human ActRIIB.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises 6 six CDRs as defined by Kabat of any one of the antibodies disclosed in Table 12. In certain embodiments, said antibody or antibody fragment binds to human ActRIIA and human ActRIIB.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises a variable heavy chain and a variable light chain of one of the antibodies disclosed in Tables 2, 7, 8, 9 or 12. In certain embodiments, said antibody or antibody fragment binds to human ActRIIA and human ActRIIB.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises a variable heavy chain and a variable light chain of one of the antibodies disclosed in Tables 2 or 12.

In an embodiment, the present disclosure relates to a nucleic acid composition comprising a nucleic acid sequence or a plurality of nucleic acid sequences encoding an antibody or antibody fragment specific for human ActRIIB, wherein said antibody or antibody fragment comprises a variable heavy chain and a variable light chain of one of the antibodies disclosed in Table 12.

In an embodiment, said nucleic acid composition and/or said nucleic acid sequence and/or said plurality of nucleic acid sequences are isolated.

In certain embodiments, the present disclosure relates to an antibody or antigen binding fragment thereof which binds to ActRIIB comprising:
 a) a heavy chain variable region CDR1 comprising the amino acid sequence of SEQ ID NO: 3;
 b) a heavy chain variable region CDR2 comprising the amino acid sequence of SEQ ID NO: 11;
 c) a heavy chain variable region CDR3 comprising the amino acid sequence of SEQ ID NO: 5;
 d) a light chain variable region CDR1 comprising the amino acid sequence of SEQ ID NO: 22;
 e) a light chain variable region CDR2 comprising the amino acid sequence of SEQ ID NO: 13 and
 f) a light chain variable region CDR3 comprising the amino acid sequence of SEQ ID NO: 14, wherein the Fc region of said antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB comprising:
 a) a heavy chain variable region CDR1 comprising the amino acid sequence of SEQ ID NO: 3;
 b) a heavy chain variable region CDR2 comprising the amino acid sequence of SEQ ID NO: 11;
 c) a heavy chain variable region CDR3 comprising the amino acid sequence of SEQ ID NO: 5;
 d) a light chain variable region CDR1 comprising the amino acid sequence of SEQ ID NO: 22;
 e) a light chain variable region CDR2 comprising the amino acid sequence of SEQ ID NO: 13 and
 f) a light chain variable region CDR3 comprising the amino acid sequence of SEQ ID NO: 14, wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

In certain embodiments, the present disclosure relates to an antibody or antigen binding fragment thereof which binds to ActRIIB:
 a) the heavy chain variable region CDR1 having the amino acid sequence of SEQ ID NO: 3;
 b) the heavy chain variable region CDR2 having the amino acid sequence of SEQ ID NO: 11;
 c) the heavy chain variable region CDR3 having the amino acid sequence of SEQ ID NO: 5;
 d) the light chain variable region CDR1 having the amino acid sequence of SEQ ID NO: 22;
 e) the light chain variable region CDR2 having the amino acid sequence of SEQ ID NO: 13; and
 f) the light chain variable region CDR3 having the amino acid sequence of SEQ ID NO: 14,
 wherein the Fc region of said isolated antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB:
 a) the heavy chain variable region CDR1 having the amino acid sequence of SEQ ID NO: 3;
 b) the heavy chain variable region CDR2 having the amino acid sequence of SEQ ID NO: 11;
 c) the heavy chain variable region CDR3 having the amino acid sequence of SEQ ID NO: 5;
 d) the light chain variable region CDR1 having the amino acid sequence of SEQ ID NO: 22;
 e) the light chain variable region CDR2 having the amino acid sequence of SEQ ID NO: 13; and
 f) the light chain variable region CDR3 having the amino acid sequence of SEQ ID NO: 14,
 wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

In certain embodiments, the present disclosure relates to an antibody or antigen binding fragment thereof which binds to ActRIIB comprising a heavy chain variable region having the amino acid sequence of SEQ ID NO: 16, and a light chain variable region having the amino acids sequence of SEQ ID NO: 23, wherein the Fc region of said antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB comprising a heavy chain variable region having the amino acid sequence of SEQ ID NO: 16, and a light chain variable region having the amino acids sequence of SEQ ID NO: 23, wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

In certain embodiments, the present disclosure relates to an antibody or antigen binding fragment thereof which binds to ActRIIB comprising:
a) a heavy chain variable region CDR1 comprising the amino acid sequence of SEQ ID NO: 3;
b) a heavy chain variable region CDR2 comprising the amino acid sequence of SEQ ID NO: 11;
c) a heavy chain variable region CDR3 comprising the amino acid sequence of SEQ ID NO: 5;
d) a light chain variable region CDR1 comprising the amino acid sequence of SEQ ID NO: 29;
e) a light chain variable region CDR2 comprising the amino acid sequence of SEQ ID NO: 30 and
f) a light chain variable region CDR3 comprising the amino acid sequence of SEQ ID NO: 14,
wherein the Fc region of said antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB comprising:
a) a heavy chain variable region CDR1 comprising the amino acid sequence of SEQ ID NO: 3;
b) a heavy chain variable region CDR2 comprising the amino acid sequence of SEQ ID NO: 11;
c) a heavy chain variable region CDR3 comprising the amino acid sequence of SEQ ID NO: 5;
d) a light chain variable region CDR1 comprising the amino acid sequence of SEQ ID NO: 29;
e) a light chain variable region CDR2 comprising the amino acid sequence of SEQ ID NO: 30 and
f) a light chain variable region CDR3 comprising the amino acid sequence of SEQ ID NO: 14,
wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

In certain embodiments, the present disclosure relates to an antibody or antigen binding fragment thereof which binds to ActRIIB:
a) the heavy chain variable region CDR1 having the amino acid sequence of SEQ ID NO: 3;
b) the heavy chain variable region CDR2 having the amino acid sequence of SEQ ID NO: 11;
c) the heavy chain variable region CDR3 having the amino acid sequence of SEQ ID NO: 5;
d) the light chain variable region CDR1 having the amino acid sequence of SEQ ID NO: 29;
e) the light chain variable region CDR2 having the amino acid sequence of SEQ ID NO: 30; and
f) the light chain variable region CDR3 having the amino acid sequence of SEQ ID NO: 14,
wherein the Fc region of said antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB:
a) the heavy chain variable region CDR1 having the amino acid sequence of SEQ ID NO: 3;
b) the heavy chain variable region CDR2 having the amino acid sequence of SEQ ID NO: 11;
c) the heavy chain variable region CDR3 having the amino acid sequence of SEQ ID NO: 5;
d) the light chain variable region CDR1 having the amino acid sequence of SEQ ID NO: 29;
e) the light chain variable region CDR2 having the amino acid sequence of SEQ ID NO: 30; and
f) the light chain variable region CDR3 having the amino acid sequence of SEQ ID NO: 14,
wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

In certain embodiments, the present disclosure relates to an antibody or antigen binding fragment thereof which binds to ActRIIB comprising a heavy chain variable region having the amino acid sequence of SEQ ID NO: 16, and a light chain variable region having the amino acids sequence of SEQ ID NO: 31, wherein the Fc region of said antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB comprising a heavy chain variable region having the amino acid sequence of SEQ ID NO: 16, and a light chain variable region having the amino acids sequence of SEQ ID NO: 31, wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

In certain embodiments, the present disclosure relates to an antibody or antigen binding fragment thereof which binds to ActRIIB comprising:
 a) a heavy chain variable region CDR1 comprising the amino acid sequence of SEQ ID NO: 3;
 b) a heavy chain variable region CDR2 comprising the amino acid sequence of SEQ ID NO: 4;
 c) a heavy chain variable region CDR3 comprising the amino acid sequence of SEQ ID NO: 5;
 d) a light chain variable region CDR1 comprising the amino acid sequence of SEQ ID NO: 33;
 e) a light chain variable region CDR2 comprising the amino acid sequence of SEQ ID NO: 13 and
 f) a light chain variable region CDR3 comprising the amino acid sequence of SEQ ID NO: 34, wherein the Fc region of said antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB comprising:
 a) a heavy chain variable region CDR1 comprising the amino acid sequence of SEQ ID NO: 3;
 b) a heavy chain variable region CDR2 comprising the amino acid sequence of SEQ ID NO: 4;
 c) a heavy chain variable region CDR3 comprising the amino acid sequence of SEQ ID NO: 5;
 d) a light chain variable region CDR1 comprising the amino acid sequence of SEQ ID NO: 33;
 e) a light chain variable region CDR2 comprising the amino acid sequence of SEQ ID NO: 13 and
 f) a light chain variable region CDR3 comprising the amino acid sequence of SEQ ID NO: 34,
 wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

In certain embodiments, the present disclosure relates to an antibody or antigen binding fragment thereof which binds to ActRIIB:
 a) the heavy chain variable region CDR1 having the amino acid sequence of SEQ ID NO: 3;
 b) the heavy chain variable region CDR2 having the amino acid sequence of SEQ ID NO: 4;
 c) the heavy chain variable region CDR3 having the amino acid sequence of SEQ ID NO: 5;
 d) the light chain variable region CDR1 having the amino acid sequence of SEQ ID NO: 33;
 e) the light chain variable region CDR2 having the amino acid sequence of SEQ ID NO: 13; and
 f) the light chain variable region CDR3 having the amino acid sequence of SEQ ID NO: 34,
 wherein the Fc region of said antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB:
 a) the heavy chain variable region CDR1 having the amino acid sequence of SEQ ID NO: 3;
 b) the heavy chain variable region CDR2 having the amino acid sequence of SEQ ID NO: 4;
 c) the heavy chain variable region CDR3 having the amino acid sequence of SEQ ID NO: 5;
 d) the light chain variable region CDR1 having the amino acid sequence of SEQ ID NO: 33;
 e) the light chain variable region CDR2 having the amino acid sequence of SEQ ID NO: 13; and
 f) the light chain variable region CDR3 having the amino acid sequence of SEQ ID NO: 34,
 wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

In certain embodiments, the present disclosure relates to an antibody or antigen binding fragment thereof which binds to ActRIIB comprising a heavy chain variable region having the amino acid sequence of SEQ ID NO: 32, and a light chain variable region having the amino acids sequence of SEQ ID NO: 35, wherein the Fc region of said antibody or antigen binding fragment comprises a mutation that increases half-life. In certain embodiments, said mutation that increases half-life is a YTE (M252Y/S254T/T256E) mutation. In certain embodiments, said antibody or antibody fragment binds to human ActRIIA and human ActRIIB.

In certain embodiments, the present disclosure relates to an antibody or antigen binding fragment thereof which binds to ActRIIB comprising a heavy chain variable region having the amino acid sequence of SEQ ID NO: 32, and a light chain variable region having the amino acids sequence of SEQ ID NO: 35, wherein said antibody or antigen binding fragment comprises a silencing modification in the Fc region, wherein the silencing modification is a PA-LALA, PG-LALA, or AEASS mutation. In certain embodiments, said antibody or antibody fragment binds to human ActRIIA and human ActRIIB.

Vectors

In an embodiment, the present disclosure provides a vector composition comprising a vector or a plurality of vectors comprising a nucleic acid composition comprising a nucleic acid sequence or a plurality of nucleic acid sequences encoding an antibody or antibody fragment specific for human ActRIIB according to the present disclosure.

In an embodiment, the present disclosure provides a vector composition comprising a vector or a plurality of vectors comprising a nucleic acid composition comprising a nucleic acid sequence or a plurality of nucleic acid sequences encoding any one of the antibodies or antibody fragments specific for human ActRIIB disclosed in Tables 2, 7, 8, 9 or 12.

In an embodiment, the present disclosure provides a vector composition comprising a vector or a plurality of vectors comprising a nucleic acid composition comprising a nucleic acid sequence or a plurality of nucleic acid sequences encoding any one of the antibodies or antibody fragments specific for human ActRIIB disclosed in Tables 2 or 12.

In an embodiment, the present disclosure provides a vector composition comprising a vector or a plurality of vectors comprising a nucleic acid composition comprising a nucleic acid sequence or a plurality of nucleic acid sequences encoding any one of the antibodies or antibody fragments specific for human ActRIIB disclosed in Table 12.

Host Cells

In an embodiment, the present disclosure provides a host cell comprising a vector composition comprising a vector or a plurality of vectors comprising a nucleic acid composition comprising a nucleic acid sequence or a plurality of nucleic acid sequences encoding an antibody or antibody fragment specific for human ActRIIB according to the present disclosure.

In an embodiment, the present disclosure refers to a host cell comprising a vector composition comprising a vector or a plurality of vectors comprising a nucleic acid composition comprising a nucleic acid sequence or a plurality of nucleic acid sequences encoding any one of the antibodies or antibody fragments specific for human ActRIIB disclosed in Tables 2, 7, 8, 9 or 12.

In an embodiment, the present disclosure refers to a host cell comprising a vector composition comprising a vector or a plurality of vectors comprising a nucleic acid composition comprising a nucleic acid sequence or a plurality of nucleic acid sequences encoding any one of the antibodies or antibody fragments specific for human ActRIIB disclosed in Tables 2 or 12.

In an embodiment, the present disclosure refers to a host cell comprising a vector composition comprising a vector or a plurality of vectors comprising a nucleic acid composition comprising a nucleic acid sequence or a plurality of nucleic acid sequences encoding any one of the antibodies or antibody fragments specific for human ActRIIB disclosed in Table 12.

In an embodiment, the host cell according to the present disclosure is able to express the antibody or antibody fragment specific for human ActRIIB encoded by the vector composition or the nucleic acid composition.

In a further embodiment, the host cell is an isolated host cell. In a further embodiment, said host cell is a mammalian cell. In an embodiment, said mammalian cell is a human cell. In another embodiment, said mammalian cell is a CHO cell. In an embodiment, said cell is a HEK cell. In another embodiment, said cell is a PERC.6 cell. In an embodiment, said cell is a HKB11 cell.

The skilled artisan will realize that the nucleic acid sequence or the plurality of nucleic acid sequences encoding the heavy and/or light chain of an antibody or antibody fragment of the present disclosure can be cloned into different vectors or into the same vector.

The vectors can be introduced into the appropriate host cells such as prokaryotic (e.g., bacterial) or eukaryotic (e.g., yeast or mammalian) cells by methods well known in the art (see e.g., "Current Protocol in Molecular Biology", Ausubel et al. (eds.), Greene Publishing Assoc and John Wiley Interscience, New York, 1989 and 1992). Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the nucleic acid sequence encoding the desired protein is transcribed into RNA in the host cell transformed by a vector containing this expression construction. The coding sequence may or may not contain a signal peptide or leader sequence. Upon expression in host cells, the antibodies or antibody fragments of the present disclosure are obtained. These steps can be achieved in different ways, as will be known by the person skilled in the art. In general, such steps typically include transforming or transfecting a suitable host cell with a nucleic acid composition or vector composition or an infectious particle, which encodes the antibody, or antibody fragments. Further, such steps typically include culturing said host cells under conditions suitable for the proliferation (multiplication, growth) of said host cells and a culturing step under conditions suitable for the production (expression, synthesis) of the encoded antibody or antibody fragment. The culturing of host cells under conditions suitable for proliferation or expression is typically accomplished in the presence of media comprising components suitable for cell growth or induction of expression. In particular, embodiments, the methods for the production of the antibodies or antibody fragments of the present disclosure further comprise the step of isolating and purifying the produced antibody or antibody fragment from the host cells or medium. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art. The antibody or antibody fragment of the present disclosure can then be purified by a number of techniques as known to the person skilled in the art.

In an embodiment, the present disclosure refers to a method of producing an antibody or antibody fragment specific for human ActRIIB of any of the antibodies disclosed in Tables 2, 7, 8, 9 or 12. In an embodiment, a method of producing an antibody or antibody fragment according to the present disclosure is provided, wherein the method comprises culturing a host cell comprising a vector composition comprising a vector or a plurality of vectors comprising a nucleic acid composition comprising a nucleic acid sequence or a plurality of nucleic acid sequences encoding an antibody or antibody fragment according to the present disclosure, under conditions suitable for expression of the antibody or antibody fragment, and isolating the antibody or antibody fragment from the host cell or host cell culture medium. An antibody or antibody fragment isolated as described herein may be purified techniques know in the art, such as high performance liquid chromatography (HPLC), ion exchange chromatography, gel electrophoresis, affinity chromatography, size exclusion chromatography, and the like. The conditions used to purify a particular antibody or antibody fragment will depend, in part, on factors such as net charge, hydrophobicity, hydrophilicity etc., and will be apparent to those having skill in the art. For affinity chromatography purification an antibody, ligand, receptor or antigen can be used to which the antibody or antibody fragment binds. For example, for affinity chromatography purification of antibody or antibody fragment according to the present disclosure, a matrix with protein A or protein G may be used. The purity of an antibody or antibody fragment can be determined by any of a variety of well-known analytical methods including gel electrophoresis, high-pressure liquid chromatography, and the like.

Therapeutic Methods

The antibodies and antibody fragments of the present disclosure, or pharmaceutical compositions incorporating the same, can be used for the treatment of various conditions. Therefore, in certain embodiments the present disclosure relates to an antibody or antibody fragment specific for human ActRIIB for use in medicine. In other embodiments the present disclosure relates to an antibody or antibody fragment specific for human ActRIIB for use in the treatment of a disease or disorder.

The antibodies and antibody fragments of present disclosure, or pharmaceutical compositions incorporating the same, can be used in metabolic diseases. They increase energy expenditure, leading to a reduction in fat body mass, while preserving lean body mass. The antibodies and antibody fragments are also an ideal combination partner with body weight lowering therapeutics, as e.g. incretins, for the treatment of obesity and type-2 diabetes (Obesity (Silver Spring) (2021) 29:500-511).

The positive effects of the antibodies and antibody fragments is not restricted to the skeletal muscle. They may therefore also be therapeutically used for heart muscle, cardiovascular and other co-morbidities associated with obesity.

Therefore, in certain embodiments the present disclosure relates to an antibody or antibody fragment specific for human ActRIIB for use in the treatment of a disease or disorder, wherein said disease or disorder is a metabolic disease, obesity, type-2 diabetes or a cardiovascular disease.

In certain embodiments, the present disclosure relates to the use of the antibodies or antibody fragments of the present disclosure for use in the treatment of a disease associated with the undesired presence of ActRIIB. In certain embodiments, the present disclosure relates to the use of the antibodies or antibody fragments of the present disclosure for use in the treatment of a disease associated with the undesired presence of ActRIIB-positive cells.

In an embodiment, the present disclosure provides a method for the treatment of a disease.

In an embodiment, the present disclosure provides a method for the treatment of a disease comprising administering to a patient an antibody or antibody fragment of the present disclosure.

In an embodiment, the present disclosure provides a method for the treatment of a disease comprising administering to a subject in need there of an antibody or antibody fragment of the present disclosure.

In an embodiment, the present disclosure provides a method for the prevention of a disease.

In an embodiment, the present disclosure provides a method for the prevention of a disease comprising administering to a subject an antibody or antibody fragment of the present disclosure.

In an embodiment, the present disclosure provides an antibody or antibody fragment according to the present disclosure for the treatment of a disease. In an embodiment, the present disclosure provides an antibody or antibody fragment according to the present disclosure for use in the treatment of a disease. In an embodiment, the present disclosure provides an antibody or antibody fragment according to the present disclosure for use in the treatment of a disease in a subject in need thereof.

In an embodiment, the present disclosure provides the use of an antibody or antibody fragment according to the present disclosure for the manufacture of a medicament. In an embodiment, the present disclosure provides an antibody or antibody fragment according to the present disclosure for use as a medicament. In an embodiment, the present disclosure provides an antibody or antibody fragment according to the present disclosure for use in medicine. In an embodiment, the present disclosure provides an antibody or antibody fragment according to the present disclosure for use as a medicament for the treatment of a subject in need thereof.

In an embodiment, the present disclosure provides an antibody or antibody fragment specific for human ActRIIB according to the present disclosure for use in a method of treating a subject having a disease comprising administering to the subject a therapeutically effective amount of an antibody or antibody fragment according to the present disclosure.

In an embodiment, the present disclosure provides a method of treating a ActRIIA or ActRIIB-mediated disease or condition in a subject in need thereof, comprising administering to the subject an antibody or an antibody fragment according to the present disclosure. In certain embodiments said ActRIIA or ActRIIB-mediated disease or condition is a metabolic disease. In certain embodiments said ActRIIA or ActRIIB-mediated disease or condition is obesity or type-2 diabetes. In certain embodiments said ActRIIA or ActRIIB-mediated disease or condition is a cardiovascular disease.

In an embodiment, the method further comprises administering to the subject a therapeutically effective amount of at least one additional therapeutic agent. The subject in need of treatment is typically a mammal, more specifically a human. For use in therapeutic methods, an antibody or antibody fragment according to the present disclosure would be formulated, dosed, and administered in a way consistent with good medical practice.

Pharmaceutical Compositions

In an embodiment, the present disclosure provides a pharmaceutical composition comprising an antibody or antibody fragment according to the present disclosure and a pharmaceutically acceptable carrier or excipient.

Antibodies are administered in an effective regime meaning a dosage, route of administration and frequency of administration that achieves the intended purpose, such as reduction of endogenous HSPCs, tissue resident or circulating immune cells or of cancer cells expressing ActRIIB. In some instances, efficacy can be observed in an individual patient relative to historical controls or past experience in the same patient. In other instances, efficacy can be demonstrated in a preclinical or clinical trial in a population of treated patients relative to a control population of untreated patients.

The pharmaceutical compositions may further comprise at least one other pharmaceutically active compound. The pharmaceutical composition according to the present disclosure can be used in the diagnosis, prevention and/or treatment of diseases associated with the undesired presence of ActRIIB. The pharmaceutical composition according to the present disclosure can be used in the diagnosis, prevention and/or treatment of diseases associated with the undesired presence of ActRIIB-positive cells. In particular, the present disclosure provides a pharmaceutical composition comprising an antibody or antibody fragment according to the present disclosure that is suitable for prophylactic, therapeutic and/or diagnostic use in a mammal, more particular in a human.

In general, an antibody or antibody fragment according to the present disclosure may be formulated as a pharmaceutical composition comprising at least one antibody or antibody fragment according to the present disclosure and at least one pharmaceutically acceptable carrier or excipient, and optionally one or more further pharmaceutically active compounds. Such a formulation may be suitable for oral, parenteral, topical administration or for administration by inhalation. Accordingly, a pharmaceutical composition comprising at least one antibody or antibody fragment according to the present disclosure may be administered parenterally, such as intravenously, or intramuscularly, or subcutaneously. Alternatively, an antibody of the invention may be administered via a non-parenteral route, such as per-orally or topically. In a preferred embodiment, a pharmaceutical composition comprising an antibody or antibody fragment according to the present disclosure is administered intravenously or subcutaneously.

Improving the efficacy and PK profile allows to maintain efficacious antibody concentrations over a prolonged period of time. This reduces the therapeutic dose needed per application and in addition to that, allows reduced frequency of drug administration. Both aspects strongly improve the patient compliance and reduce the costs of goods ensuring sustained therapeutic effects, while keeping expenses for patient and health care systems in a reasonable range.

In particular, an antibody or antibody fragment according to the present disclosure may be used in combination with one or more pharmaceutically, active compounds that are or can be used for the prevention and/or treatment of the diseases in which a target antigen of interest is involved, as a result of which a synergistic effect may or may not be obtained. Examples of such compounds, as well as routes, methods and pharmaceutical formulations or compositions for administering them will be clear to the clinician.

In an embodiment, the present disclosure provides a pharmaceutical composition comprising an antibody or antibody fragment according to the present disclosure for use in the prevention and/or treatment of a disease associated with the undesired presence of ActRIIB. In an embodiment, the present disclosure provides a pharmaceutical composition comprising an antibody or antibody fragment according to the present disclosure for use in the prevention and/or treatment of a disease associated with the undesired presence of ActRIIB-positive cells. In an embodiment, the present disclosure provides a pharmaceutical composition comprising an antibody or antibody fragment according to the present disclosure for the use as a medicament. In an embodiment, the present disclosure provides a pharmaceutical composition comprising an antibody or antibody fragment according to the present disclosure for use in the prevention and/or treatment of a metabolic disease, obesity, type-2 diabetes or a cardiovascular disease.

In an embodiment, the present disclosure provides a method for the treatment a metabolic disease, obesity, type-2 diabetes or a cardiovascular disease in a subject in need thereof using a pharmaceutical composition comprising an antibody or antibody fragment according to the present disclosure.

Further provided is a method of producing an antibody or antibody fragment according to the present disclosure in a form suitable for administration in vivo, the method comprising (a) obtaining an antibody or antibody fragment by a method according to the present disclosure, and (b) formulating said antibody or antibody fragment with at least one pharmaceutically acceptable carrier or excipient, whereby a preparation of antibody or antibody fragment is formulated for administration in vivo. Pharmaceutical compositions according to the present disclosure comprise a therapeutically effective amount of one or more antibodies or antibody fragments according to the present disclosure dissolved in a pharmaceutically acceptable carrier or excipient.

Diagnostic Use

In an embodiment, the present disclosure provides the use of an antibody or antibody fragment specific for human ActRIIB according to the present disclosure for the diagnosis of a disease. In an embodiment, the present disclosure provides the use of an antibody or antibody fragment according to the present disclosure for the detection of human ActRIIB. In an embodiment, the present disclosure provides a method for detecting human ActRIIB in a subject or a sample, comprising the step of contacting said subject or sample with an antibody or antibody fragment specific for human ActRIIB of the present disclosure. In an embodiment, the present disclosure provides a method for diagnosing a disease in a subject, comprising the step of contacting said subject or sample with an antibody or antibody fragment according to the present disclosure. The antibodies may also be used to determine ActRIIB expression levels in cells from patients. The ActRIIB expressions levels may serve as therapeutic biomarkers, for example for patient stratification.

EXAMPLES

Example 1: Goal of the Present Invention

Overall goal of the present invention is to provide an improved version of the antibody bimagrumab. The antibodies to be generated have one or more of the following properties: an improved efficacy against ActRIIA and ActRIIB, an improved PK and PD profile, and/or higher stability, making the antibodies suitable for s.c. administration. Optionally they carry Fc modifications making the antibodies safe for prolonged treatments.

Figure 11:
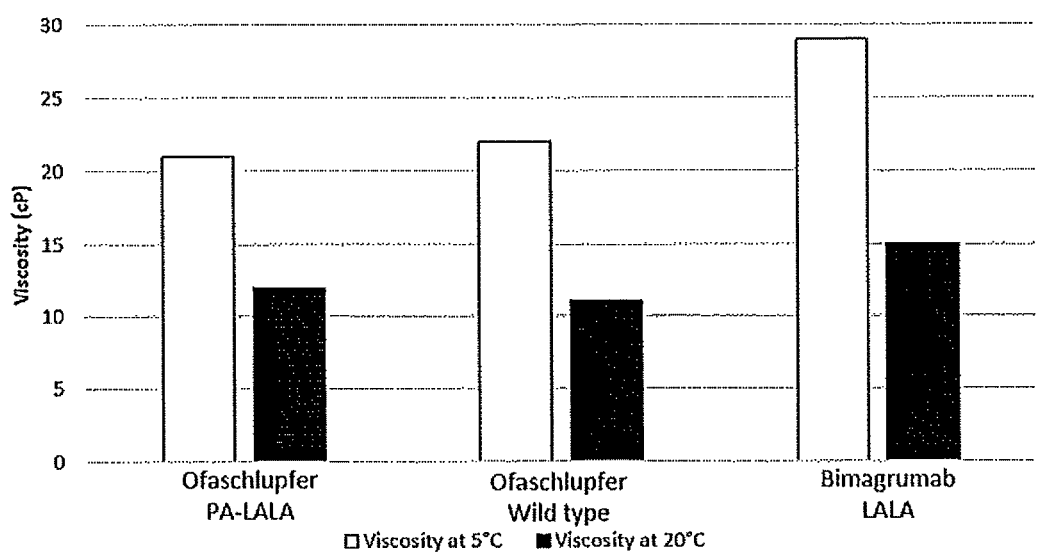
FIG. 11 shows that the viscosity of Ofaschlupfer is lower at both 5° C. and 20° C., compared to bimagrumab, irrespective of the Fc part of the binders.

These goals were tried to achieve via various approaches. An optimization of the CDRs, either in silico or AI-guided was utilized in order to optimize the affinity and reduce unspecific binding, eventually leading to an increased potence and an improved PD and PK. Due to the higher efficacy also lower doses for treatment are possible. Optimization of the framework regions via germline switching was used to improve the biophysical properties. Finally, Fc engineering was tested with the goal to improve FcRn binding and to silence FcRγ binding, which should likewise improve PK and PD and reduce immune activation. FIG. 11 shows a schematic overview about the parallel approaches taken.

Example 2: General Experimental Procedures

Example 2.1: Determination of the Melting Temperature of Immunoglobulins

Melting temperature of immunoglobulins was measured by standard procedures using differential scanning fluorimetry (DSF).

Example 2.2: Determination of the Hydrophobicity Profile of Immunoglobulins by Hydrophobic Interaction Chromatography The molecules were characterized by hydrophobic interaction chromatography using an Agilent 1260 infinity II system. The elution was done through an Agilent bio HIC column (4.6*100 mm, 3.5 um) with a linear gradient starting at 60% mobile phase A (50 mM sodium phosphate buffer, pH 7+2 M ammonium sulfate) to 100% mobile phase B (50 mM sodium phosphate buffer; pH 7) at a flow rate of 1 mL/min. Eluted protein was detected at an absorbance of 280 nm.

Example 2.3: Determination of Charged Based Interaction of Immunoglobulin by Heparin Chromatography The charged based interaction profile of the candidates was determined by heparin chromatography. Analysis was performed using a Agilent 1260 infinity II system with a TSK-GEL Heparin-5 PW column (5.0 cm×5.0 cm, 10 um). The molecule was eluted by a linear gradient starting from 100% mobile phase A 50 mM Tris, pH 7.4 to 100% mobile

Example 2.4: Determination of the Affinity of Immunoglobulins to ActRIIA and ActRIIB The affinity interaction profile of the immunoglobulins was determined using an immuno-based-assay called Meso Scale Discovery (MSD) Solution Equilibrium Titration (MSD-SET). In this assay, the antigen (either ActR2A or ActR2B) was coated onto an MSD 96-well detection plate. The SET plate was prepared by mixing the immunoglobulins at a constant concentration with titrated antigen and incubated overnight at 4° C. to reach equilibrium. After blocking of the MSD plate, 50 µl of the sample solutions containing the Immunoglobulin-Antigen mix (SET plate) were transferred onto the antigen-coated detection MSD plate. These samples were then incubated for 20 minutes to allow for binding of any free antibodies without significantly shifting the equilibrium. To detect the bound antibodies on the plate, a detection antibody Anti Human Antibody (Goat) Sulfo-TAG Labelled (PN: R32AJ-5) was added. The electrochemiluminescence (ECL) readout was then detected by adding a Read Buffer and measuring ECL using an MSD instrument (Sector S 600MM). Data analysis was performed on GraphPad Prism using equation for IgG or Fab from Journal of Biomolecular Screening 2015, Vol. 20(10) 1256-1267.

Example 2.5: Myostatin Inhibition (SMAD RGA Assay)

The candidates were characterized in SMAD RGA (reporter gene assay) assays stimulated with Myostatin in order to evaluate their potency and efficacy towards the inhibition of ActRIIA and ActRIIB. TGFB/SMAD Signaling Pathway SBE Reporter HEK293 cells (BPS BioScience) were washed with PBS, detached using 0.05% Trypsin and seeded at 35000 cells/well in a 96-well white flat-bottom plate in 100 uL Medium (MEM media, 10% FBS, 1% NEAA, 1 mM Na pyruvate, 1% Pen/Strep). The next day, medium was exchanged with 90 uL Assay medium (MEM media, 0.5% FBS, 1% NEAA, 1 mM Na pyruvate, 1% Pen/Strep) containing diluted Antibodies of interest (10-0.00015 ug/mL) or Control. Cells were incubated at 37° C., 5% $CO_2$ for 4 h. Subsequently, 10 uL of 500 ng/mL Myostatin (Cat #120-00, Peprotech) were added to the cells and cells incubated overnight. The next day, 100 µL of ONE-Step Luciferase Detection reagent (BPS Bioscience) were added to the cell solution (both equilibrated to room temperature) and incubated for 15 min on a plate shaker, before measuring luminescence using the Envision Plate Reader.

Example 2.6: Activin Inhibition (SMAD RGA Assay)

The candidates were characterized in SMAD RGA assays stimulated with Activin in order to evaluate their potency and efficacy towards the inhibition of ActRIIA and ActRIIB. TGFB/SMAD Signaling Pathway SBE Reporter HEK293 cells (BPS BioScience) were washed with PBS, detached using 0.05% Trypsin and seeded at 35000 cells/well in a 96-well white flat-bottom plate in 100 uL Medium (MEM media, 10% FBS, 1% NEAA, 1 mM Na pyruvate, 1% Pen/Strep). The next day, medium was exchanged with 90 uL Assay medium (MEM media, 0.5% FBS, 1% NEAA, 1 mM Na pyruvate, 1% Pen/Strep) containing diluted Antibodies of interest (10-0.00015 ug/mL) or Control. Cells were incubated at 37° C., 5% $CO_2$ for 4 h. Subsequently, 10 uL of 10 ng/mL Activin A (Cat #120-14E, Peprotech) were added to the cells and cells incubated overnight. The next day, 100 uL of ONE-Step Luciferase Detection reagent (BPS Bioscience) were added to the cell solution (both equilibrated to room temperature) and incubated for 15 min on a plate shaker, before measuring luminescence using the Envision Plate Reader.

Example 2.7: Determination of Unspecific Binding

In order to compare the unspecific binding behaviour of different candidates, FACS EC50 values were determined in HEK293 cells expressing ActRIIA and ActRIIB. The cells were treated with saturating concentrations of Activin in order to block specific binding. The same experimental setup was performed without Activin treatment in order to determine the specific binding. HEK293 cells (BPS BioScience) were washed with PBS, detached using TrypLE and seeded at 0.1 Mio cells per well in a round bottom 96-well plate in 100 uL FACS buffer (PBS+2% FBS+1 mM EDTA). Cells were washed once with FACS buffer and resuspended in 20 µL of 1.25 ug/mL Activin solution (Cat #120-14E, Peprotech). Cells were incubated for 30 min on ice on a plate shaker, before adding 20 µL of Antibodies of interest (10-0.00064 ug/mL) or Control. Cells were incubated for additional 30 min on ice on a plate shaker. Subsequently, cells were washed twice with ice cold FACS buffer, 1:200 diluted detection Antibody (IgG (H+L) Cross-Adsorbed Goat anti-Human, Alexa Fluor®488; #A11013, Thermo Fisher Scientific) was added and cells were incubated for 30 min on ice in the dark. Cells were washed twice with FACS buffer, resuspended in 60 µL of FACS buffer and signal analyzed on the Novocyte Quanteon Flow Cytometer.

Example 2.8: Antibody Production

DNA encoding the antibodies of the present disclosure were codon optimized and cloned into expression vectors. After verification of the constructs by sequencing, plasmids were prepared. CHO K1 cells were transiently transfected with the plasmids and antibodies were produced at the selected scale.

Cell culture supernatant were collected and two-step purified. Antibodies had a purity of over 95% purity and endotoxin levels below 0.5 EU/mg. Antibodies were resuspended at 1-5 mg/ml. Platform analytical testing included A280, SDS-PAGE/Caliper-SDS (R&NR), SEC-HPLC, LC-MS and endotoxin measurements.

Example 3: CDR Optimization Approach

Each CDR position in Bimagrumab was independently diversified and analyzed in a yeast based-platform for mutations with improved affinity and reduced unspecific binding (PSR). After the enrichment of candidates with beneficial properties, more than 70 derivatives of bimagrumab, with various mutations in the CDRs were tested The following properties were in the main focus:
increase the affinity to ActRIIA, while maintaining the affinity to ActRIIB,
lower unspecific binding, and
germline revision to a lower immunogenicity risk.

phase B 50 mM Tris, 1 M NaCl, pH 7.4 at a flow rate of 0.35 mL/min. Absorbance wavelength for detection was set at 280 nm.

Finally, the following 15 binders were selected as the most promising antibodies:

TABLE 2

| SEQ ID No. | Description | Sequence |
|---|---|---|
| colspan=3 | Antibody *Springerle* | |
| 3 | HCDR1 | SSYIN |
| 4 | HCDR2 | TINPVSGSTSYAQKFQG |
| 5 | HCDR3 | GGWFDY |
| 6 | LCDR1 | TGTSSDVGSYNYVN |
| 13 | LCDR2 | GVSKRES |
| 79 | LCDR3 | GTFAGGSYRGV |
| 9 | VH | QVQLVQSGAEVKKPGASVKVSCKASGYTFTSSYINWVRQAPGQGLEWMGTINPVSGSTSYAQKFQGRVTMTRDTSISTAYMELSRLRSDDTAVYYCARGGWFDYWGQGTLVTVSS |
| 80 | VL | QSALTQPASVSGSPGQSITISCTGTSSDVGSYNYVNWYQQHPGKAPKLMIYGVSKRESGVSNRFSGSKSGNTASLTISGLQAEDEADYYCGTFAGGSYRGVFGGGTKLTVL |
| colspan=3 | Antibody *Biiramooscht* | |
| 3 | HCDR1 | SSYIN |
| 4 | HCDR2 | TINPVSGSTSYAQKFQG |
| 5 | HCDR3 | GGWFDY |
| 6 | LCDR1 | TGTSSDVGSYNYVN |
| 13 | LCDR2 | GVSKRES |
| 18 | LCDR3 | GTFAGGAYYGV |
| 9 | VH | QVQLVQSGAEVKKPGASVKVSCKASGYTFTSSYINWVRQAPGQGLEWMGTINPVSGSTSYAQKFQGRVTMTRDTSISTAYMELSRLRSDDTAVYYCARGGWFDYWGQGTLVTVSS |
| 58 | VL | QSALTQPASVSGSPGQSITISCTGTSSDVGSYNYVNWYQQHPGKAPKLMIYGVSKRESGVSNRFSGSKSGNTASLTISGLQAEDEADYYCGTFAGGAYYGVEGGGTKLTVL |
| colspan=3 | Antibody *Rippla* | |
| 3 | HCDR1 | SSYIN |
| 4 | HCDR2 | TINPVSGSTSYAQKFQG |
| 5 | HCDR3 | GGWFDY |
| 33 | LCDR1 | TGTSSDVGSYNRVN |
| 13 | LCDR2 | GVSKRES |
| 34 | LCDR3 | GTFAGGRYYGV |
| 59 | VH | QVQLVQSGAEVRKPGASVKVSCKASGYTFTSSYINWVRQAPGQGLEWMGTINPVSGSTSYAQKFQGRVTMTRDTSISTAYMELSRLRSDDTAVYYCARGGWFDYWGQGTLVTVSS |
| 60 | VL | QSALTQPASVSGSPGQSITISCTGTSSDVGSYNRVNWYQQHPGKAPKLMIYGVSKRESGVSNRFSGSKSGNTASLTISGLQAEDEADYYCGTFAGGRYYGVFGGGTKLTVL |
| colspan=3 | Antibody *Pfitzauf* | |
| 3 | HCDR1 | SSYIN |
| 4 | HCDR2 | TINPVSGSTSYAQKFQG |
| 5 | HCDR3 | GGWFDY |
| 52 | LCDR1 | TGTSSDVGSGNYVN |
| 13 | LCDR2 | GVSKRES |

TABLE 2-continued

| SEQ ID No. | Description | Sequence |
|---|---|---|
| 57 | LCDR3 | GTFAGGKYYGV |
| 9 | VH | QVQLVQSGAEVKKPGASVKVSCKASGYTFTSSYINWVRQAPGQGLEWMGTINPVSGSTSYAQKFQGRVTMTRDTSISTAYMELSRLRSDDTAVYYCARGGWFDYWGQGTLVTVSS |
| 61 | VL | QSALTQPASVSGSPGQSITISCTGTSSDVGSGNYVNWYQQHPGKAPKLMIYGVSKRESGVSNRFSGSKSGNTASLTISGLQAEDEADYYCGTFAGGKYYGVFGGGTKLTVL |

Antibody *Ochsauga*

| 3 | HCDR1 | SSYIN |
| 11 | HCDR2 | TINAVSGSTSYAQKFQG |
| 49 | HCDR3 | GGWFDV |
| 53 | LCDR1 | TGTSSDIGSYNYVN |
| 13 | LCDR2 | GVSKRES |
| 8 | LCDR3 | GTFAGGSYYGV |
| 62 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARGGWFDVWGQGTLVTVSS |
| 63 | VL | QSALTQPASVSGSPGQSITISCTGTSSDIGSYNYVNWYQQHPGKAPKLMIYGVSKRESGVSNRFSGSKSGNTASLTISGLQAEDEADYYCGTFAGGSYYGVFGGGTKLTVL |

Antibody *Floischbrühsupp*

| 3 | HCDR1 | SSYIN |
| 11 | HCDR2 | TINAVSGSTSYAQKFQG |
| 5 | HCDR3 | GGWFDY |
| 17 | LCDR1 | TGTSSDVGSFNYVN |
| 13 | LCDR2 | GVSKRES |
| 18 | LCDR3 | GTFAGGAYYGV |
| 64 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARGGWFDYWGQGTLVTVSS |
| 65 | VL | QSALTQPASVSGSPGQSITISCTGTSSDVGSENYVNWYQQHPGKAPKLMIKGVSKRESGVSNRFSGSKSGNTASLTISGLQAEDEADYYCGTFAGGAYYGVFGGGTKLTVL |

Antibody *Bäratatza*

| 3 | HCDR1 | SSYIN |
| 11 | HCDR2 | TINAVSGSTSYAQKEQG |
| 50 | HCDR3 | SGWFDY |
| 6 | LCDR1 | TGTSSDVGSYNYVN |
| 55 | LCDR2 | GVSKQQS |
| 8 | LCDR3 | GTFAGGSYYGV |
| 66 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARSGWFDYWGQGTLVTVSS |
| 67 | VL | QSALTQPASVSGSPGQSITISCTGTSSDVGSYNYVNWYQQHPGKAPKLMIYGVSKQQSGVSNRFSGSKSGNTASLTISGLQAEDEADYYCGTFAGGSYYGVFGGGTKLTVL |

TABLE 2-continued

| SEQ ID No. | Description | Sequence |
|---|---|---|
| | Antibody Hefaknöpfla | |
| 3 | HCDR1 | SSYIN |
| 11 | HCDR2 | TINAVSGSTSYAQKFQG |
| 5 | HCDR3 | GGWFDY |
| 22 | LCDR1 | TGTSSDVGSKNYVN |
| 13 | LCDR2 | GVSKRES |
| 57 | LCDR3 | GTFAGGKYYGV |
| 64 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARGGWFDYWGQGTLVTVSS |
| 68 | VL | QSALTQPASVSGSPGQSITISCTGTSSDVGSKNYVNWYQQHPGKAPKLMIYGVSKRESGVSNRFSGSKSGNTASLTISGLQAEDEADYYCGTFAGGKYYGVFGGGTKLTVL |
| | Antibody Duuranad | |
| 3 | HCDR1 | SSYIN |
| 11 | HCDR2 | TINAVSGSTSYAQKFQG |
| 5 | HCDR3 | GGWFDY |
| 17 | LCDR1 | TGTSSDVGSFNYVN |
| 13 | LCDR2 | GVSKRES |
| 18 | LCDR3 | GTFAGGAYYGV |
| 64 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARGGWEDYWGQGTLVTVSS |
| 69 | VL | QSALTQPASVSGSPGQSITISCTGTSSDVGSFNYVNWYQQHPGKAPKLMIRGVSKRESGVSNRFSGSKSGNTASLTISGLQAEDEADYYCGTFAGGAYYGVFGGGTKLTVL |
| | Antibody Wurschdsalat | |
| 3 | HCDR1 | SSYIN |
| 11 | HCDR2 | TINAVSGSTSYAQKFQG |
| 5 | HCDR3 | GGWFDY |
| 6 | LCDR1 | TGTSSDVGSYNYVN |
| 13 | LCDR2 | GVSKRES |
| 57 | LCDR3 | GTFAGGKYYGV |
| 70 | VH | QVQLVQSGAEVKKPGASVKVSCKASGYTFTSSYINWVRQAPGQGLEWMGTINAVSGSTSYAQKFQGRVTMTRDESISTAYMELSRLRSDDTAVYYCARGGWFDYWGQGTLVTVSS |
| 72 | VL | QSALTQPASVSGSPGQSITISCTGTSSDVGSYNYVNWYQQHPGKAPKLMIYGVSKRESGVSNRFSGSKSGNTASLTISGLQAEDEADYYCGTFAGGKYYGVFGGGTKLTVL |
| | Antibody Riaba | |
| 3 | HCDR1 | SSYIN |
| 11 | HCDR2 | TINAVSGSTSYAQKFQG |
| 5 | HCDR3 | GGWFDY |
| 6 | LCDR1 | TGTSSDVGSYNYVN |
| 20 | LCDR2 | GVSKRDS |

TABLE 2-continued

| SEQ ID No. | Description | Sequence |
|---|---|---|
| 57 | LCDR3 | GTFAGGKYYGV |
| 64 | VH | QVQLVQSGAEVKKPGASVKVSCKASGYTFTSSYINWVRQAPGQGLEWMGTINAVSGSTSYAQKFQGRVTMTRDTSISTAYMELSRERSDDTAVYYCARGGWFDYWGQGTLVTVSS |
| 73 | VL | QSALTQPASVSGSPGQSITISCTGTSSDVGSYNYVNWYQQHPGKAPKLMIYGVSKRDSGVSNRFSGSKSGNTASLTISGLQAEDEADYYCGTFAGGKYYGVFGGGTKLTVL |

Antibody *Ochsamaulsalat*

| SEQ ID No. | Description | Sequence |
|---|---|---|
| 3 | HCDR1 | SSYIN |
| 11 | HCDR2 | TINAVSGSTSYAQKFQG |
| 5 | HCDR3 | GGWFDY |
| 26 | LCDR1 | TGTSSDVGSRNYVN |
| 13 | LCDR2 | GVSKRES |
| 27 | LCDR3 | GTFAGGDYYGV |
| 64 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARGGWFDYWGQGTLVTVSS |
| 74 | VL | QSALTQPASVSGSPGQSITISCTGTSSDVGSRNYVNWYQQHPGKAPKLMIYGVSKRESGVSNRFSGSKSGNTASLTISGLQAEDEADYYCGTFAGGDYYGVFGGGTKLTVL |

Antibody *Fasnetsküchla*

| SEQ ID No. | Description | Sequence |
|---|---|---|
| 3 | HCDR1 | SSYIN |
| 11 | HCDR2 | TINAVSGSTSYAQKFQG |
| 5 | HCDR3 | GGWFDY |
| 29 | LCDR1 | TGTSSDVGSANYVN |
| 30 | LCDR2 | GVSRRPS |
| 57 | LCDR3 | GTFAGGKYYGV |
| 64 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARGGWFDYWGQGTLVTVSS |
| 75 | VL | QSALTQPASVSGSPGQSITISCTGTSSDVGSANYVNWYQQHPGKAPKPMIYGVSRRPSGVSNRFSGSKSGNTASLTISGLQAEDEADYYCGTFAGGKYYGVFGGGTKLTVL |

Antibody *Hasaschlegel*

| SEQ ID No. | Description | Sequence |
|---|---|---|
| 3 | HCDR1 | SSYIN |
| 11 | HCDR2 | TINAVSGSTSYAQKFQG |
| 5 | HCDR3 | GGWFDY |
| 54 | LCDR1 | TGTSSDVGSYDYVN |
| 13 | LCDR2 | GVSKRES |
| 8 | LCDR3 | GTFAGGSYYGV |
| 64 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARGGWFDYWGQGTLVTVSS |
| 76 | VL | QSALTQPASVSGSPGQSITISCTGTSSDVGSYDYVNWYQQHPGKAPKLMIHGVSKRESGVSNRFSGSKSGNTASLTISGLQAEDEADYYCGTFAGGSYYGVFGGGTKLTVL |

TABLE 2-continued

| SEQ ID No. | Description | Sequence |
|---|---|---|
| Antibody *Hutzelbrot* | | |
| 3 | HCDR1 | SSYIN |
| 11 | HCDR2 | TINAVSGSTSYAQKFQG |
| 5 | HCDR3 | GGWFDY |
| 22 | LCDR1 | TGTSSDVGSKNYVN |
| 56 | LCDR2 | GVSKRQS |
| 27 | LCDR3 | GTFAGGDYYGV |
| 64 | VH | QVQLVQSGAEVKKPGASVKVSCKASGYTFTSSYINWVRQAPGQGLEWMGTINAVSGSTSYAQKFQGRVTMTRDTSISTAYMELSRLRSDDTAVYYCARGGWFDYWGQGTLVTVSS |
| 77 | VL | QSALTQPASVSGSPGQSITISCTGTSSDVGSKNYVNWYQQHPGKAPKLMIYGVSKRQSGVSNRFSGSKSGNTASLTISGLQAEDEADYYCGTFAGGDYYGVFGGGTKLTVL |
| Antibody *Durrfloischeggla* | | |
| 3 | HCDR1 | SSYIN |
| 11 | HCDR2 | TINAVSGSTSYAQKFQG |
| 5 | HCDR3 | GGWFDY |
| 51 | LCDR1 | TGTSSDVGSYNVVN |
| 13 | LCDR2 | GVSKRES |
| 57 | LCDR3 | GTFAGGKYYGV |
| 71 | VH | QVQLVQSGAEVKKPGASVKVSCKASGYTFTSSYINWVRQAPGQGLEWMGTINAVSGSTSYAQKFQGRVTMTRDVSISTAYMELSRLRSDDTAVYYCARGGWFDYWGQGTLVTVSS |
| 78 | VL | QSALTQPASVSGSPGQSITISCTGTSSDVGSYNVVNWYQQHPGKAPKLMISGVSKRESGVSNRFSGSKSGNTASLTISGLQAEDEADYYCGTFAGGKYYGVFGGGTKLTVL |

The antibody nomenclature used herein in the present disclosure refers to a combination of a specific VH/VL pair. Such antibodies may be used with different constant regions (such as a human IgG1 constant region or a murine IgG2a constant region), with different Fc modifications (such as the PA-LALA format or YTE mutations), or any other mutations. The use such formats or mutations is indicated in the respective examples.

Example 4: Characterization of Selected Binders Generated in Example 3

Example 4.1: Initial Bulk Characterization

Figure 2:
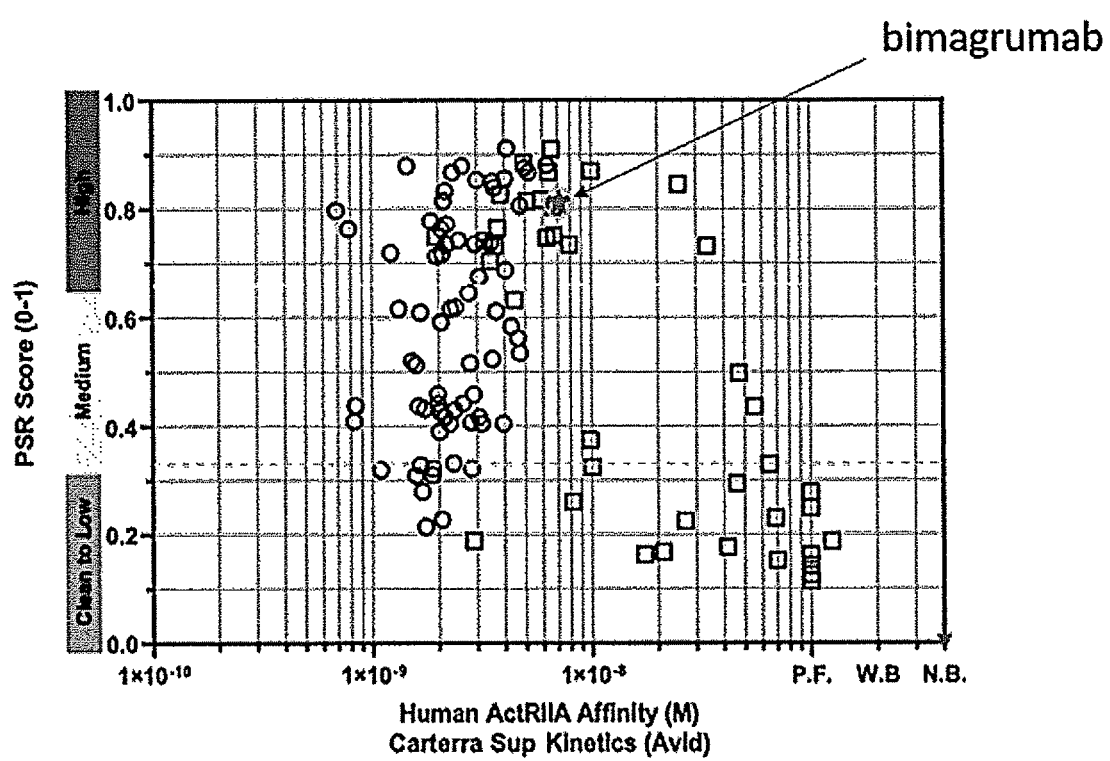
FIG. 2 shows the PSR score as a measure for unspecific binding for selected antibodies of the present disclosure.

A panel of antibodies generated in Example 3 was compared to bimagrumab with respect to the affinity to ActRIIA and their PSR score. The PSR score is a measure for unspecific binding. Results are shown in FIG. 2. Each data point represent one antibody. As can be a diversity of antibodies could be generated, including antibodies with an increased affinity to ActRIIA, as well as antibodies with a lower PSR score (both as compared to bimagrumab). This demonstrates that it is possible to generate improved variants of bimagrumab.

Example 4.2: Reduced Unspecific Binding

Figure 3:
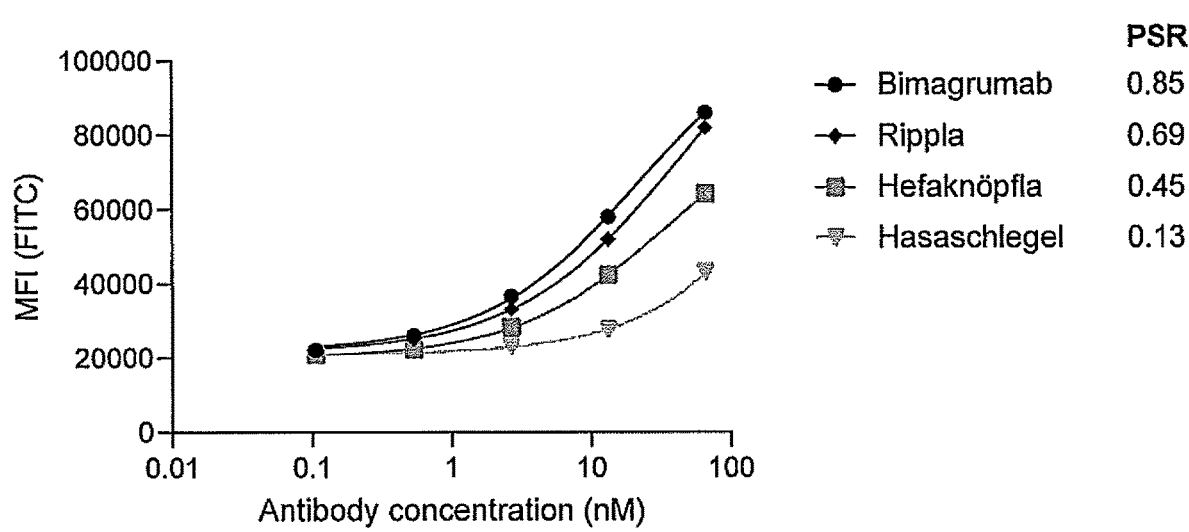
FIG. 3 shows that certain derivatives of bimagrumab show a reduced unspecific binding.

Selected antibodies were tested for unspecific binding on HEK cells. As described in more detail in Example 2.7, FACS binding EC50 values were determined on HEK293 cells expressing ActRIIA and ActRIIB. The cells were treated with saturating concentrations of Activin in order to block specific binding. The same experimental setup was performed without Activin treatment in order to determine the specific binding. Results are shown in FIG. 3. As can be seen unspecific binding is improved for antibody Hefaknöpfla, and more so for antibody Hasaschlegel.

Example 4.3: Heparin and HIC Score

Figure 4:
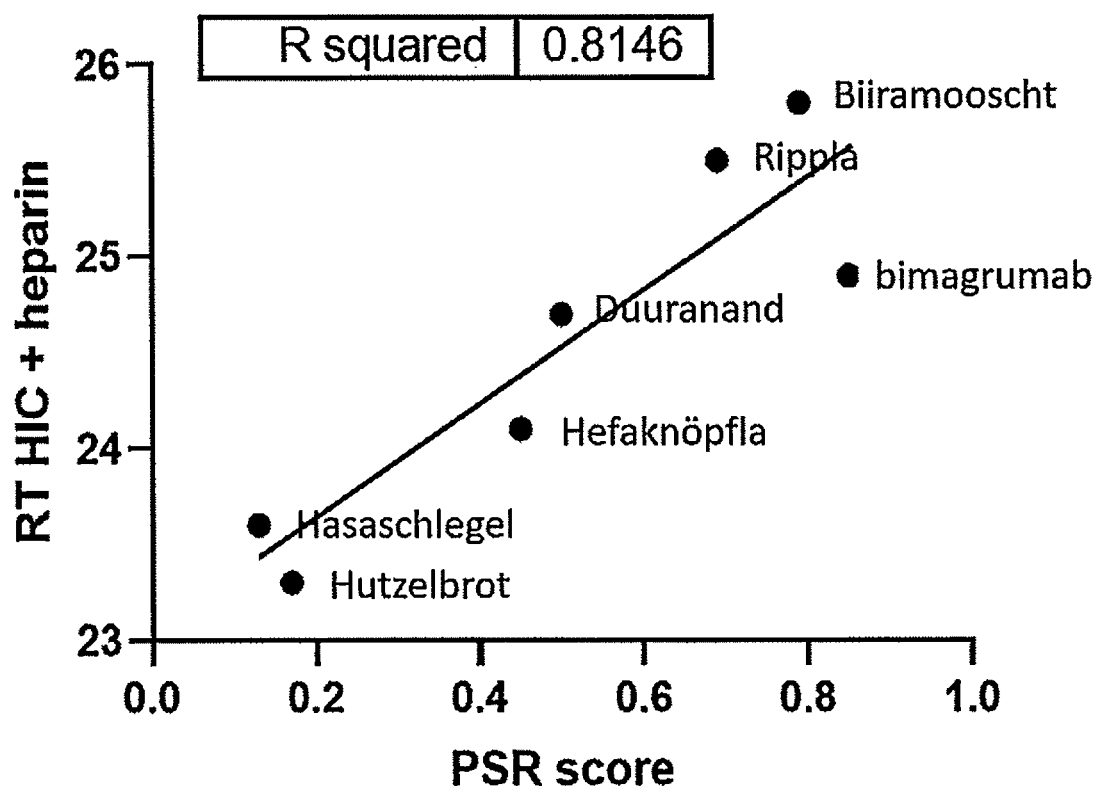
FIG. 4 shows that certain derivatives of bimagrumab show are improved with respect to their Heparin score and their PSR score, and that this improvement correlates with the PSR score.

Selected antibodies were also tested for hydrophobicity and charged based interaction score (the score is calculated from the sum of the HIC retention and the heparin retention) as described in Example 1. Results are shown in FIG. 4. It can be seen that certain derivatives of bimagrumab are improved with respect to their Heparin score and their PSR score, and that this improvement correlates with the PSR score.

Example 4.4: Affinity to ActRIIA and ActRIIB

For selected antibodies, the affinity for ActRIIA was measured. Results are shown in the following Table (mean data from at least two independent experiments).

TABLE 3

| Antibody | Affinity on ActRIIA [pM] | Fold Difference to bimagrumab | IC50 [nM] | IC90 [nM] | IC50 fold difference to bimagrumab | IC90 fold difference to bimagrumab |
| --- | --- | --- | --- | --- | --- | --- |
| Bimagrumab | 198 | 1 | 0.5172 | 8.072 | 1 | 1 |
| Springerle | 27 | 7.3 | 0.09465 | 1.495 | 5.46 | 5.4 |
| Biiramooscht | 28 | 6.4 | 0.08598 | 1.157 | 6.02 | 6.98 |
| Rippla | 41 | 4 | 0.02086 | 1.275 | 25.63 | 6.33 |

As can be seen, the tested antibodies had an at least 5-fold higher affinity to ActRIIA compared to bimagrumab.

The experiment was repeated with additional, improved derivatives of bimagrumab. Results are shown in the following Table (mean data from at least two independent experiments).

TABLE 4A

| Antibody | Affinity on ActRIIA [pM] | Fold Difference to bimagrumab | IC50 [nM] | IC90 [nM] | IC50 fold difference to bimagrumab | IC90 fold difference to bimagrumab |
| --- | --- | --- | --- | --- | --- | --- |
| Bimagrumab | 198 | 1 | 0.2944 | 6.573 | 1 | 1 |
| Bäratatza | 23 | 49.5 | 0.105 | 2.773 | 2.80 | 2.4 |
| Hefaknöpfla | 15 | 13.2 | 0.01104 | 1.598 | 26.98 | 4.11 |
| Riaba | 14 | 10 | 0.03713 | 1.6 | 7.96 | 4.11 |

Again a strong increase of the affinity to ActRIIA was observed compared to bimagrumab.

Shown in Table 4B are the affinity of the selected binders for ActRIIA and ActRIIB (mean data from at least two independent experiments).

TABLE 4B

| Antibody | KD for ActRIIA [pM] | KD for ActRIIB [pM] |
| --- | --- | --- |
| Springerle | 27 | ND |
| Biiramooscht | 28 | 5 |
| Rippla | 41 | 5 |
| Pfitzauf | 52 | 8 |
| Ochsauga | 16 | 6 |
| Floischbrühsupp | 23 | 10 |
| Bäratatza | 23 | 5 |
| Hefaknöpfla | 15 | 5 |
| Duuranad | 9 | 5 |
| Wurschdsalat | 5 | 6 |
| Riaba | 14 | 4 |
| Ochsamaulsalat | 20 | 10 |
| Fasnetsküchla | 29 | 8 |
| Hasaschlegel | 18 | 13 |
| Hutzelbrot | 21 | 10 |
| Dürrfloischeggla | 33 | 9 |

Example 4.5: Further Characterization

Figure 9:
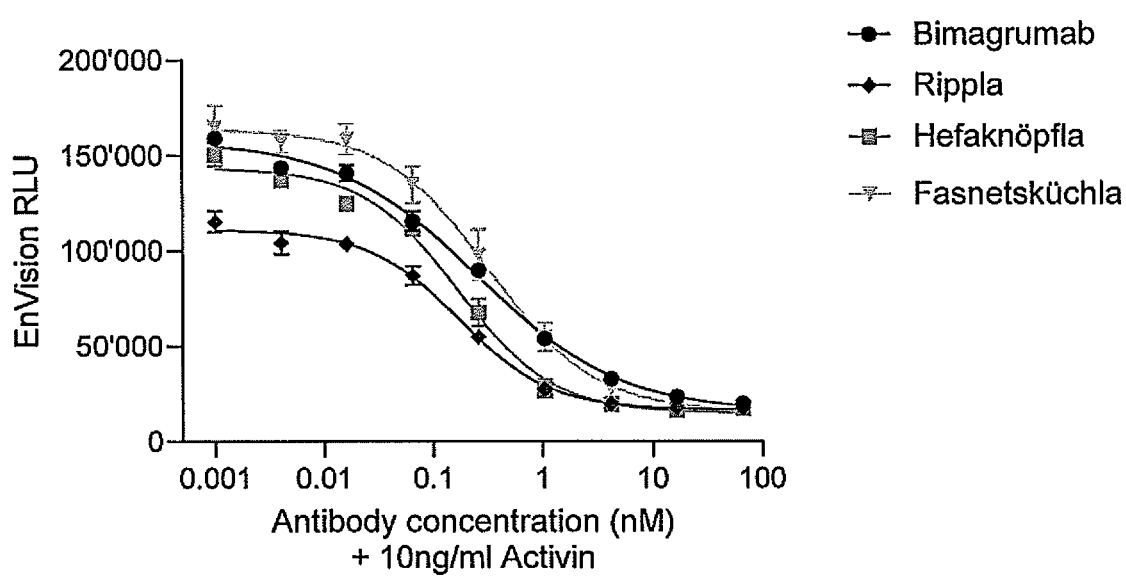
FIG. 9 shows the results of certain derivatives of bimagrumab in an Activin assay binding.
Figure 10:
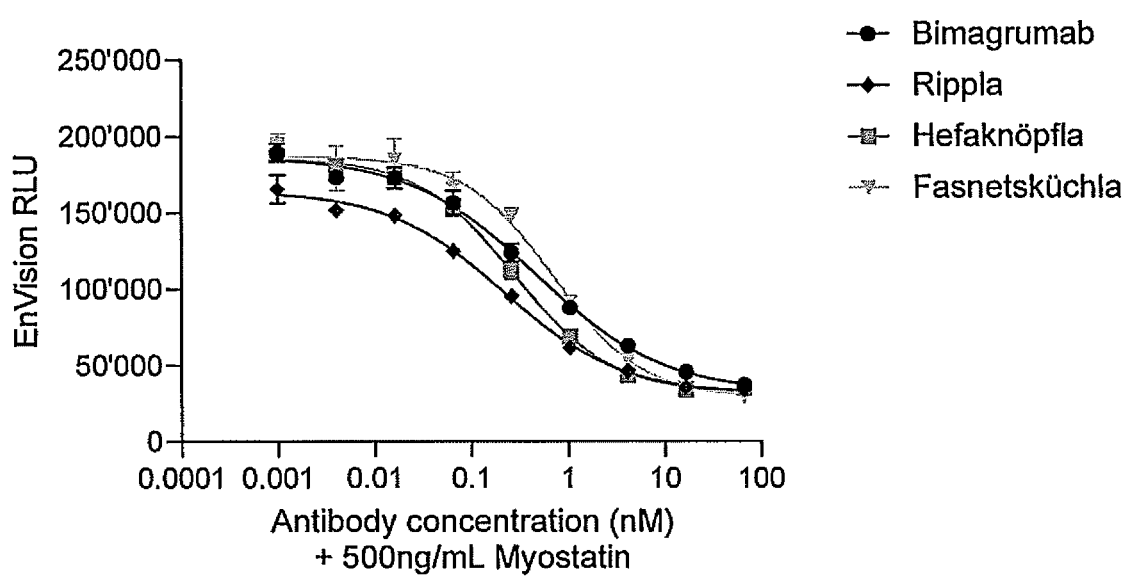
FIG. 10 shows the results of certain derivatives of bimagrumab in a Myostatin assay binding.

Additional derivatives of bimagrumab were characterized for their affinity for ActRIIA, their affinity for ActRIIB, their activity in an activin (SMAD RGA) assay and their activity in a myostatin (SMAD RGA) assay. The binders were tested in all assays as full length immunoglobulins and as Fab's. Results are summarized in the following Table. Results for selected antibodies are also shown in FIGS. 9 (Activin assay) and 10 (Myostatin assay). Shown are mean data from at least two independent experiments.

TABLE 5

|  | Affinity on ActRII A | | | Affinity on ActRII B | | | Activity in Smad RGA (Activin) | | | Activity in Smad RGA (Myostatin) | | |
| --- | --- | --- | --- | --- | --- | --- | --- | --- | --- | --- | --- | --- |
|  | IgG KD [nM] | Fab KD [nM] | Fold difference (Fab:IgG) | IgG KD [nM] | Fab KD [nM] | Fold difference (Fab:IgG) | IgG IC50 [nM] | Fab IC50 [nM] | Fold difference (Fab:IgG) | IgG IC50 [nM] | Fab IC50 [nM] | Fold difference (Fab:IgG) |
| Biiramooscht | 0.028 | 0.145 | 5.2 | 0.005 | 0.021 | 4.4 | 0.210 | 1.580 | 7.4 | 0.270 | 2.090 | 7.9 |
| Rippla | 0.042 | 0.157 | 3.8 | 0.005 | 0.006 | 1.1 | 0.090 | 0.400 | 4.6 | 0.150 | 0.780 | 5.1 |
| Hefaknöpfla | 0.015 | 0.091 | 6.1 | 0.005 | 0.228 | 47.6 | 0.130 | 4.060 | 31.5 | 0.260 | 3.700 | 14.2 |
| Duuranad | 0.009 | 0.047 | 5.4 | 0.005 | 0.360 | 67.9 | 0.300 | 6.190 | 20.5 | 0.390 | 7.850 | 20.2 |
| Wurschdsalat | 0.005 | 0.125 | 24.5 | 0.006 | 0.823 | 127.7 | 0.290 | 9.900 | 33.8 | 0.330 | 13.36 | 40.7 |
| Riaba | 0.014 | >50 | 4153. | 0.004 | 1.573 | 369.2 | 0.140 | 27.93 | 196.0 | 0.330 | 64.56 | 198.6 |
| Ochsamaulsalat | 0.020 | 0.055 | 2.8 | 0.010 | 0.062 | 6.0 | 0.430 | 1.500 | 3.5 | 0.550 | 2.320 | 4.2 |
| Fasnetsküchla | 0.029 | 0.114 | 3.9 | 0.008 | 0.026 | 3.1 | 0.430 | 1.210 | 2.8 | 0.480 | 2.320 | 4.8 |
| bimagrumab | 0.194 | 0.765 | 3.9 | 0.004 | 0.012 | 2.7 | 0.500 | 4.390 | 8.8 | 0.560 | 6.870 | 12.2 |

Additionally, selected binders were tested for their cross-reactivity to mouse ActRIIA, mouse ActRIIB and cynomolgus monkey ActRIIB. Results are summarized in the following Table (mean data from at least two independent experiments).

TABLE 6A

|  |  | Affinity KD [pM] | | | | | |
| --- | --- | --- | --- | --- | --- | --- | --- |
|  |  | Bimagrumab | Bebballesgmias | Hefaknöpfla | Duuranad | Wurschdsalat | Ochsamaulsalat |
| ActRIIA | Human | 152.5 | 67.0 | 12.3 | 21.2 | 21.8 | 23.2 |
|  | Mouse | 112.6 | 58.7 | 10.0 | 22.5 | 3.6 | 29.4 |
| ActRIIB | Human | 3.9 | 1.3 | 4.3 | 5.4 | 4.4 | 8.2 |
|  | Mouse | 0.5 | 2.6 | 0.4 | 0.9 | 1.3 | 3.4 |
|  | Cyno | 2.3 | 5.0 | 1.5 | 2.3 | 2.3 | 4.1 |

Shown in Table 6B are the results for additional selected binders in Activin SMAD RGA and Myostation SMAD RGA assays.

TABLE 6B

|  | Activin SMAD RGA (nM) | | | Myostatin SMAD RGA (nM) | | |
| --- | --- | --- | --- | --- | --- | --- |
| Antibody | IC50 (nM) | IC90 (nM) | nb of expts | IC50 (nM) | IC90 (nM) | # of expts |
| Bimagrumab | 0.3200 | 6.2000 | n = 8 | 0.2920 | 13.4700 | n = 5 |
| Backstoikäs | 0.1803 | 3.7100 | n = 1 | 0.0875 | 1.2280 | n = 1 |
| Bäradreck | 0.2565 | 4.9900 | n = 2 | 0.2554 | 4.0500 | n = 2 |
| Bebballesgmias | 0.1707 | 2.8840 | n = 2 | 0.1815 | 1.9430 | n = 2 |
| Springerle | 0.0940 | 1.3790 | n = 1 | ND | ND |  |
| Biiramooscht | 0.1611 | 1.5808 | n = 4 | 0.2221 | 2.7783 | n = 3 |
| Rippla | 0.0582 | 1.5823 | n = 6 | 0.2128 | 9.6489 | n = 5 |
| Pfitzauf | 0.2305 | 3.0255 | n = 2 | 0.0984 | 1.3500 | n = 1 |
| Ochsauga | 0.2384 | 3.1520 | n = 2 | 0.3268 | 2.2080 | n = 1 |
| Floischbrühsupp | 0.3241 | 4.6887 | n = 3 | 0.3937 | 2.6190 | n = 1 |
| Bäratatza | 0.1375 | 2.1390 | n = 2 | 0.0537 | 0.4909 | n = 1 |
| Hefaknöpfla | 0.1392 | 2.1638 | n = 6 | 0.2112 | 5.3716 | n = 5 |
| Duuranad | 0.2717 | 2.2215 | n = 4 | 0.4323 | 4.4500 | n = 3 |
| Wurschdsalat | 0.2664 | 1.8995 | n = 4 | 0.4000 | 3.8857 | n = 3 |
| Riaba | 0.1342 | 2.1402 | n = 5 | 0.2634 | 2.1760 | n = 3 |
| Ochsamaulsalat | 0.3404 | 2.5113 | n = 4 | 0.6534 | 5.5947 | n = 3 |
| Fasnetsküchla | 0.3467 | 3.8200 | n = 4 | 0.5126 | 4.6293 | n = 3 |
| Hasaschlegel | 0.7215 | 5.5645 | n = 2 | 0.9770 | 6.5910 | n = 1 |
| Hutzelbrot | 0.4219 | 3.6170 | n = 3 | 0.7300 | 3.0570 | n = 1 |
| Dürrfloischeggla | 0.4231 | 4.8620 | n = 2 | 0.6790 | 6.0870 | n = 1 |

Example 4.6: Summary of the Optimization Process so Far

Considerable achievement was in the optimization process so far. Several antibodies, for example antibody Rippla, show a strong increase of potency compared to bimagrumab, while the pattern of unspecific binding was kept constant. Another group of antibodies, for example antibody Hasaschlegel, showed a similar potency as bimagrumab, but are highly improved with respect to unspecific binding. A third group of antibodies, for example antibody Hefaknöpfla, show intermediate characteristics, i.e. both, potency and unspecific binding, were improved compared to bimagrumab.

In parallel to the optimization in a yeast-based platform, in silico optimization was performed using Schroedinger modeling software. Measurement of the affinity to ActRIIB indicated that most of the binders did not have a higher, but rather an even lower affinity to ActRIIB. One of the binders however, antibody Backstoikäs, showed an affinity to ActRIIB that was at least as good as that of bimagrumab, and also the other properties of antibody Backstoikäs tested made this antibody a possible starting point for further optimization.

Antibody Backstoikäs has the following amino acid sequence:

TABLE 7

| SEQ ID No. | Description | Sequence |
|---|---|---|
| 3 | HCDR1 | SSYIN |
| 4 | HCDR2 | TINPVSGSTSYAQKFQG |
| 5 | HCDR3 | GGWFDY |
| 43 | VH | QVQLVQSGAEVKKPGASVKVSCKASGYKFTSSYINWVRQAPGQGLEWMGTINPVSGSTSYAQKFQGRVTMTRDTSISTAYMELSRLRSDDTAVYYCARGGWFDYWGQGTLVTVSS |
| 6 | LCDR1 | TGTSSDVGSYNYVN |
| 44 | LCDR2 | GVSKRPR |
| 8 | LCDR3 | GTFAGGSYYGV |
| 45 | VI | QSALTQPASVSGSPGQSITISCTGTSSDVGSYNYVNWYQQHPGKAPKLMIYGVSKRPRGVSNRFSGSKSGNTASLTISGLQAEDEADYYCGTFAGGSYYGVFGGGTKLTVL |

Example 5: Germline Switching Approach

In a parallel approach VH/VL pairs were selected that were previously reported generally to have improved biophysical properties (MAbs (2013) 5: 445-70). More than 110 derivatives of bimagrumab, carrying various mutations in the frameworks and the CDRs were tested. The aim was to identify variants with improved biophysical properties and reduced unspecific binding, while maintaining Bimagrumab like affinities.

One of the binders, antibody Bäradreck, showed good biophysical properties and reduced unspecific binding, while maintaining Bimagrumab like affinities. These characteristics made this antibody an ideal basis for the combination with CDR optimized candidates.

Antibody Bäradreck has the following amino acid sequence:

TABLE 8

| SEQ ID No. | Description | Sequence |
|---|---|---|
| 3 | HCDR1 | SSYIN |
| 4 | HCDR2 | TINPVSGSTSYAQKFQG |
| 5 | HCDR3 | GGWFDY |
| 24 | VH | QVQLVQSGAEVKKPGSSVKVSCKASGYTFTSSYINWVRQAPGQGLEWMGTINPVSGSTSYAQKFQGRVTITADTSTSTAYMELSSLRSEDTAVYYCARGGWFDYWGQGTLVTVSS |
| 6 | LCDR1 | TGTSSDVGSYNYVN |
| 7 | LCDR2 | GVSKRPS |

TABLE 8-continued

| SEQ ID No. | Description | Sequence |
|---|---|---|
| 8 | LCDR3 | GTFAGGSYYGV |
| 46 | VL | QSALTQPRSVSGSPGQSVTISCTGTSSDVGSYNYVNWYQQHPGKAP KLMIYGVSKRPSGVPDRFSGSKSGNTASLTISGLQAEDEADYYCGT FAGGSYYGVFGGGTKLTVL |

In addition to the antibody Bäradreck which was only optimized in framework positions, the antibody Bebballesgmias contained in addition to the framework, also CDR optimized positions improving affinities towards ActRIIA and B.

Antibody Bebballesgmias has the following amino acid sequence:

TABLE 9

| SEQ ID No. | Description | Sequence |
|---|---|---|
| 3 | HCDR1 | SSYIN |
| 4 | HCDR2 | TINPVSGSTSYAQKFQG |
| 5 | HCDR3 | GGWFDY |
| 47 | VH | QVQLVQSGAEVKKPGSSVKVSCKASGYKFTSSYINWVRQAPGQGLEWM GTINPVSGSTSYAQKFQGRVTITADTSTSTAYMELSSLRSEDTAVYYC ARGGWFDYWGQGTLVTVSS |
| 6 | LCDR1 | TGTSSDVGSYNYVN |
| 44 | LCDR2 | GVSKRPR |
| 8 | LCDR3 | GTFAGGSYYGV |
| 48 | VL | QSALTQPRSVSGSPGQSVTISCTGTSSDVGSYNYVNWYQQHPGKAPKL MIYGVSKRPRGVPDRESGSKSGNTASLTISGLQAEDEADYYCGTFAGG SYYGVFGGGTKLTVL |

Figure 5:
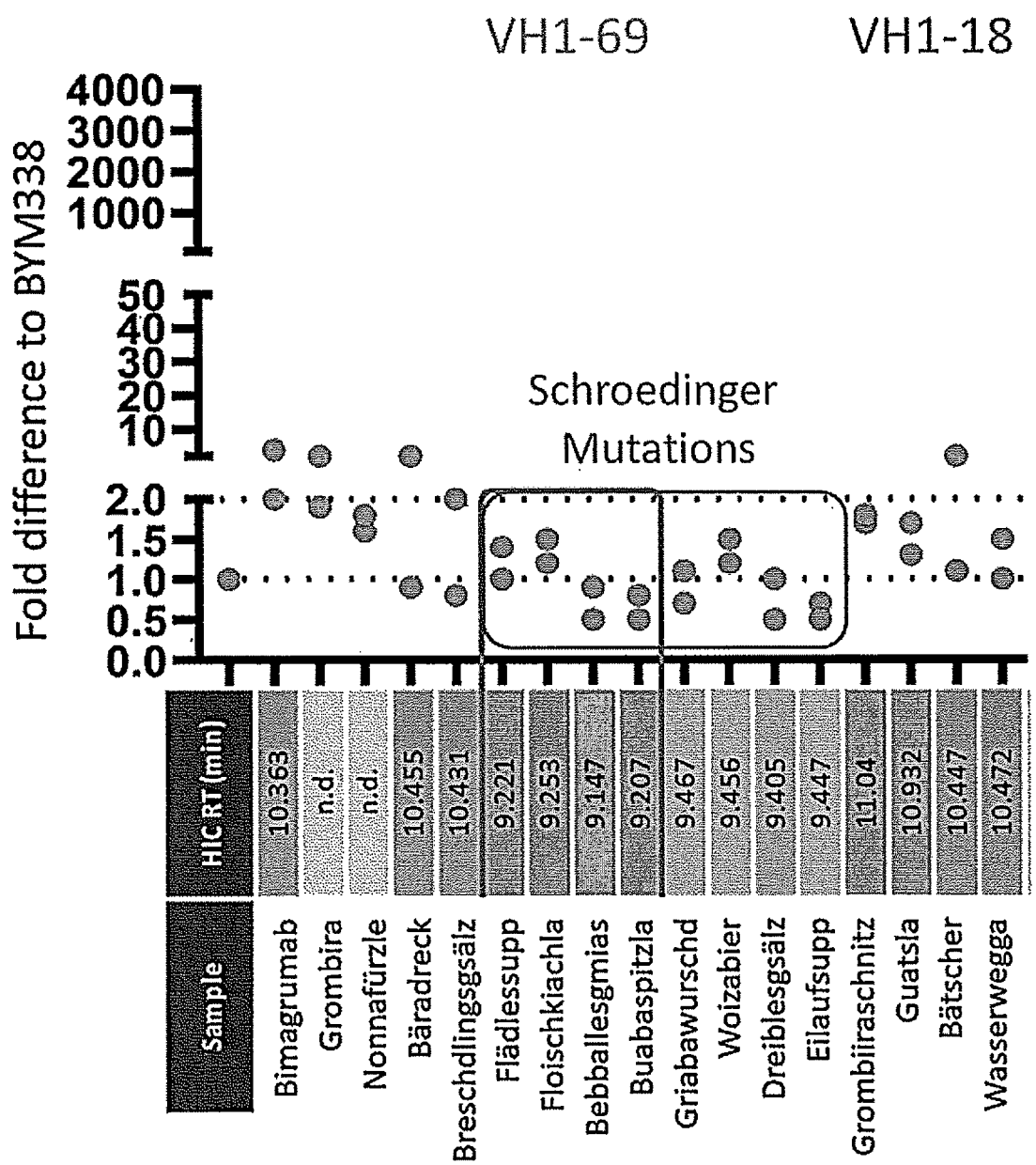
FIG. 5 shows results of the measurement of the affinity of selected binders for ActRIIA and ActRIIB.

Results of the measurements of the affinity for ActRIIA and ActRIIB are shown in FIG. 5. It can be seen that certain germline sequences led to an increase of the affinity for both, ActRIIA and ActRIIB. This was particularly pronounced for binders with a VH1-69 germline sequence. Additionally, these binders had a shorter retention time in hydrophobic interchange chromatography (HIC).

Example 6: Characterization of Selected Binders Generated in Example 5

Example 6.1: Melting Temperature

Results of the measurement of the melting temperature for selected binders is shown in Table 10. Many binders were superior or in the range of bimagrumab (mean data from at least two independent experiments).

TABLE 10

| Antibody | Cumulant radius [nm] | TM1 [° C.] | TM2 [° C.] |
|---|---|---|---|
| Bimagrumab | 5.22 | 64.9 | 73.7 |
| Bäradreck | 5.28 | 64.8 | 77.8 |
| Breschdlingsgsälz | 5.39 | 64.9 | 75.7 |
| Bebballesgmias | 5.20 | 64.8 | 78.2 |
| Buabaspitzla | 5.28 | 64.7 | 76.1 |
| Dreiblesgsälz | 5.21 | 64.7 | 78.4 |
| Eilaufsupp | 5.21 | 64.7 | 76.3 |

Example 6.2: Myostatin Inhibition

Results of the measurement of myostatin inhibition are shown in Table 11. Several binders had an IC50 better than that of bimagrumab (mean data from at least two independent experiments).

TABLE 11

| Antibody | IC50 [nM] |
|---|---|
| Bimagrumab | 0.292 |
| Bäradreck | 0.2554 |
| Flädlessupp | 0.1790 |
| Floischkiachla | 0.0976 |
| Bebballesgmias | 0.1707 |
| Buabaspitzla | 0.1331 |
| Griabawurschd | 0.1544 |
| Grombiiraschnitz | 0.3555 |
| Guatsla | 0.4330 |
| Kuddlasupp | 0.1643 |
| Laugabrezla | 1.353 |
| Leberspätzla | 2.143 |

Example 7: Combination of Improved Characteristics

Example 7.1: Generation of Additional Improved Binders

In the next optimization campaign it was tested if it is possible to combine the advantageous properties of the antibodies generated so far, combining framework candidates with CDR optimized as shown in the following Table.

TABLE 12

| SEQ ID No. | Description | Sequence |
|---|---|---|
| colspan="3" | Antibody *Mauldascha* | |
| 3 | HCDR1 | SSYIN |
| 11 | HCDR2 | TINAVSGSTSYAQKFQG |
| 5 | HCDR3 | GGWFDY |
| 6 | LCDR1 | TGTSSDVGSYNYVN |
| 13 | LCDR2 | GVSKRES |
| 14 | LCDR3 | GTFAGGKYYGV |
| 12 | VH | QVQLVQSGAEVKKPGSSVKVSCKASGYTFTSSYINWVRQAPGQGLEWMGTINAVSGSTSYAQKFQGRVTITADESTSTAYMELSSLRSEDTAVYYCARGGWFDYWGQGTLVTVSS |
| 15 | VL | QSALTQPRSVSGSPGQSVTISCTGTSSDVGSYNYVNWYQQHPGKAPKLMIYGVSKRESGVPDRFSGSKSGNTASLTISGLQAEDEADYYCGTFAGGKYYGVFGGGTKLTVL |
| colspan="3" | Antibody *Metzelsupp* | |
| 3 | HCDR1 | SSYIN |
| 11 | HCDR2 | TINAVSGSTSYAQKFQG |
| 5 | HCDR3 | GGWFDY |
| 17 | LCDR1 | TGTSSDVGSFNYVN |
| 13 | LCDR2 | GVSKRES |
| 18 | LCDR3 | GTFAGGAYYGV |
| 16 | VH | QVQLVQSGAEVKKPGSSVKVSCKASGYTFTSSYINWVRQAPGQGLEWMGTINAVSGSTSYAQKFQGRVTITADTSTSTAYMELSSLRSEDTAVYYCARGGWFDYWGQGTLVTVSS |
| 19 | VL | QSALTQPRSVSGSPGQSVTISCTGTSSDVGSFNYVNWYQQHPGKAPKLMIRGVSKRESGVPDRESGSKSGNTASLTISGLQAEDEADYYCGTFAGGAYYGVFGGGTKLTVL |
| colspan="3" | Antibody *Nonnafürzla* | |
| 3 | HCDR1 | SSYIN |
| 11 | HCDR2 | TINAVSGSTSYAQKFQG |
| 5 | HCDR3 | GGWFDY |
| 6 | LCDR1 | TGTSSDVGSYNYVN |
| 20 | LCDR2 | GVSKRDS |
| 14 | LCDR3 | GTFAGGKYYGV |
| 16 | VH | QVQLVQSGAEVKKPGSSVKVSCKASGYTFTSSYINWVRQAPGQGLEWMGTINAVSGSTSYAQKFQGRVTITADTSTSTAYMELSSLRSEDTAVYYCARGGWFDYWGQGTLVTVSS |
| 21 | VL | QSALTQPRSVSGSPGQSVTISCTGTSSDVGSYNYVNWYQQHPGKAPKLMIYGVSKRDSGVPDRFSGSKSGNTASLTISGLQAEDEADYYCGTFAGGKYYGVFGGGTKLTVL |

TABLE 12-continued

| SEQ ID No. | Description | Sequence |
|---|---|---|
| colspan=3 | Antibody *Ofaschlupfer* | |
| 3 | HCDR1 | SSYIN |
| 11 | HCDR2 | TINAVSGSTSYAQKFQG |
| 5 | HCDR3 | GGWFDY |
| 22 | LCDR1 | TGTSSDVGSKNYVN |
| 13 | LCDR2 | GVSKRES |
| 14 | LCDR3 | GTFAGGKYYGV |
| 16 | VH | QVQLVQSGAEVKKPGSSVKVSCKASGYTFTSSYINWVRQAPGQGLEWMGTINAVSGSTSYAQKFQGRVTITADTSTSTAYMELSSLRSEDTAVYYCARGGWFDYWGQGTLVTVSS |
| 23 | VL | QSALTQPRSVSGSPGQSVTISCTGTSSDVGSKNYVNWYQQHPGKAPKLMIYGVSKRESGVPDRFSGSKSGNTASLTISGLQAEDEADYYCGTFAGGKYYGVFGGGTKLTVL |
| colspan=3 | Antibody *Oierspätzla* | |
| 3 | HCDR1 | SSYIN |
| 4 | HCDR2 | TINPVSGSTSYAQKFQG |
| 5 | HCDR3 | GGWFDY |
| 6 | LCDR1 | TGTSSDVGSYNYVN |
| 13 | LCDR2 | GVSKRES |
| 18 | LCDR3 | GTFAGGAYYGV |
| 24 | VH | QVQLVQSGAEVKKPGSSVKVSCKASGYTFTSSYINWVRQAPGQGLEWMGTINPVSGSTSYAQKFQGRVTITADTSTSTAYMELSSLRSEDTAVYYCARGGWFDYWGQGTLVTVSS |
| 25 | VL | QSALTQPRSVSGSPGQSVTISCTGTSSDVGSYNYVNWYQQHPGKAPKLMIYGVSKRESGVPDRFSGSKSGNTASLTISGLQAEDEADYYCGTFAGGAYYGVFGGGTKLTVL |
| colspan=3 | Antibody *Rauchfloisch* | |
| 3 | HCDR1 | SSYIN |
| 11 | HCDR2 | TINAVSGSTSYAQKFQG |
| 5 | HCDR3 | GGWFDY |
| 26 | LCDR1 | TGTSSDVGSRNYVN |
| 13 | LCDR2 | GVSKRES |
| 27 | LCDR3 | GTFAGGDYYGV |
| 16 | VH | QVQLVQSGAEVKKPGSSVKVSCKASGYTFTSSYINWVRQAPGQGLEWMGTINAVSGSTSYAQKFQGRVTITADTSTSTAYMELSSLRSEDTAVYYCARGGWFDYWGQGTLVTVSS |
| 28 | VL | QSALTQPRSVSGSPGQSVTISCTGTSSDVGSRNYVNWYQQHPGKAPKLMIYGVSKRESGVPDRFSGSKSGNTASLTISGLQAEDEADYYCGTFAGGDYYGVFGGGTKLTVL |
| colspan=3 | Antibody *Schwardamaga* | |
| 3 | HCDR1 | SSYIN |
| 11 | HCDR2 | TINAVSGSTSYAQKFQG |
| 5 | HCDR3 | GGWFDY |
| 29 | LCDR1 | TGTSSDVGSANYVN |
| 30 | LCDR2 | GVSRRPS |

TABLE 12-continued

| SEQ ID No. | Description | Sequence |
|---|---|---|
| 14 | LCDR3 | GTFAGGKYYGV |
| 16 | VH | QVQLVQSGAEVKKPGSSVKVSCKASGYTFTSSYINWVRQAPGQGLEWMGTINAVSGSTSYAQKFQGRVTITADTSTSTAYMELSSLRSEDTAVYYCARGGWFDYWGQGTLVTVSS |
| 31 | VL | QSALTQPRSVSGSPGQSVTISCTGTSSDVGSANYVNWYQQHPGKAPKPMIYGVSRRPSGVPDRFSGSKSGNTASLTISGLQAEDEADYYCGTFAGGKYYGVFGGGTKLTVL |

Antibody *Soidawürstle*

| SEQ ID No. | Description | Sequence |
|---|---|---|
| 3 | HCDR1 | SSYIN |
| 4 | HCDR2 | TINPVSGSTSYAQKFQG |
| 5 | HCDR3 | GGWFDY |
| 33 | LCDR1 | TGTSSDVGSYNRVN |
| 13 | LCDR2 | GVSKRES |
| 34 | LCDR3 | GTFAGGRYYGV |
| 32 | VH | QVQLVQSGAEVRKPGSSVKVSCKASGYTFTSSYINWVRQAPGQGLEWMGTINPVSGSTSYAQKFQGRVTITADTSTSTAYMELSSLRSEDTAVYYCARGGWFDYWGQGTLVTVSS |
| 35 | VL | QSALTQPRSVSGSPGQSVTISCTGTSSDVGSYNRVNWYQQHPGKAPKLMIYGVSKRESGVPDRFSGSKSGNTASLTISGLQAEDEADYYCGTFAGGRYYGVFGGGTKLTVL |

Antibody *Zibebe*

| SEQ ID No. | Description | Sequence |
|---|---|---|
| 3 | HCDR1 | SSYIN |
| 11 | HCDR2 | TINAVSGSTSYAQKFQG |
| 5 | HCDR3 | GGWFDY |
| 6 | LCDR1 | TGTSSDVGSYNYVN |
| 13 | LCDR2 | GVSKRES |
| 14 | LCDR3 | GTFAGGKYYGV |
| 36 | VH | QVQLVQSGAEVKKPGSSVKVSCKASGYKFTSSYINWVRQAPGQGLEWMGTINAVSGSTSYAQKFQGRVTITADESTSTAYMELSSLRSEDTAVYYCARGGWFDYWGQGTLVTVSS |
| 15 | VL | QSALTQPRSVSGSPGQSVTISCTGTSSDVGSYNYVNWYQQHPGKAPKLMIYGVSKRESGVPDRFSGSKSGNTASLTISGLQAEDEADYYCGTFAGGKYYGVFGGGTKLTVL |

Antibody *Schnitzbrot*

| SEQ ID No. | Description | Sequence |
|---|---|---|
| 3 | HCDR1 | SSYIN |
| 11 | HCDR2 | TINAVSGSTSYAQKFQG |
| 5 | HCDR3 | GGWFDY |
| 6 | LCDR1 | TGTSSDVGSYNYVN |
| 20 | LCDR2 | GVSKRDS |
| 14 | LCDR3 | GTFAGGKYYGV |
| 37 | VH | QVQLVQSGAEVKKPGSSVKVSCKASGYKFTSSYINWVRQAPGQGLEWMGTINAVSGSTSYAQKFQGRVTITADTSTSTAYMELSSLRSEDTAVYYCARGGWFDYWGQGTLVTVSS |
| 21 | VL | QSALTQPRSVSGSPGQSVTISCTGTSSDVGSYNYVNWYQQHPGKAPKLMIYGVSKRDSGVPDRFSGSKSGNTASLTISGLQAEDEADYYCGTFAGGKYYGVFGGGTKLTVL |

TABLE 12-continued

| SEQ ID No. | Description | Sequence |
|---|---|---|
| | | Antibody *Wiebela* |
| 3 | HCDR1 | SSYIN |
| 11 | HCDR2 | TINAVSGSTSYAQKFQG |
| 5 | HCDR3 | GGWFDY |
| 22 | LCDR1 | TGTSSDVGSKNYVN |
| 13 | LCDR2 | GVSKRES |
| 14 | LCDR3 | GTFAGGKYYGV |
| 37 | VH | QVQLVQSGAEVKKPGSSVKVSCKASGYKFTSSYINWVRQAPGQGLEWMGTINAVSGSTSYAQKFQGRVTITADTSTSTAYMELSSLRSEDTAVYYCARGGWFDYWGQGTLVTVSS |
| 23 | VL | QSALTQPRSVSGSPGQSVTISCTGTSSDVGSKNYVNWYQQHPGKAPKLMIYGVSKRESGVPDRESGSKSGNTASLTISGLQAEDEADYYCGTFAGGKYYGVFGGGTKLTVL |
| | | Antibody *Krapfa* |
| 3 | HCDR1 | SSYIN |
| 11 | HCDR2 | TINAVSGSTSYAQKFQG |
| 5 | HCDR3 | GGWFDY |
| 22 | LCDR1 | TGTSSDVGSKNYVN |
| 13 | LCDR2 | GVSKRES |
| 14 | LCDR3 | GTFAGGKYYGV |
| 38 | VH | QVQLVQSGAEVKKPGSSVKVSCKASGHKFTSSYINWVRQAPGQGLEWMGTINAVSGSTSYAQKFQGRVTITADTSTSTAYMELSSLRSEDTAVYYCARGGWFDYWGQGTLVTVSS |
| 23 | VL | QSALTQPRSVSGSPGQSVTISCTGTSSDVGSKNYVNWYQQHPGKAPKLMIYGVSKRESGVPDRFSGSKSGNTASLTISGLQAEDEADYYCGTFAGGKYYGVFGGGTKLTVL |
| | | Antibody *Seela* |
| 3 | HCDR1 | SSYIN |
| 11 | HCDR2 | TINAVSGSTSYAQKFQG |
| 5 | HCDR3 | GGWFDY |
| 22 | LCDR1 | TGTSSDVGSKNYVN |
| 13 | LCDR2 | GVSKRES |
| 14 | LCDR3 | GTFAGGKYYGV |
| 37 | VH | QVQLVQSGAEVKKPGSSVKVSCKASGYKFTSSYINWVRQAPGQGLEWMGTINAVSGSTSYAQKFQGRVTITADTSTSTAYMELSSLRSEDTAVYYCARGGWFDYWGQGTLVTVSS |
| 39 | VL | QSALTQPRSVSGSPGQSVTISCTGTSSDVGSKNYVNWYQQHPGKAPKHMIYGVSKRESGVPDRESGSKSGNTASLTISGLQAEDEADYYCGTFAGGKYYGVFGGGTKLTVL |
| | | Antibody *Peitscheschdegga* |
| 3 | HCDR1 | SSYIN |
| 11 | HCDR2 | TINAVSGSTSYAQKFQG |
| 5 | HCDR3 | GGWFDY |
| 22 | LCDR1 | TGTSSDVGSKNYVN |
| 13 | LCDR2 | GVSKRES |

TABLE 12-continued

| SEQ ID No. | Description | Sequence |
|---|---|---|
| 14 | LCDR3 | GTFAGGKYYGV |
| 37 | VH | QVQLVQSGAEVKKPGSSVKVSCKASGYKFTSSYINWVRQAPGQGLEW MGTINAVSGSTSYAQKFQGRVTITADTSTSTAYMELSSLRSEDTAVY YCARGGWFDYWGQGTLVTVSS |
| 40 | VL | QSALTQPRSVSGSPGQSVTISCTGTSSDVGSKNYVNWYQQHPGKAPK LMIHGVSKRESGVPDRFSGSKSGNTASLTISGLQAEDEADYYCGTFA GGKYYGVFGGGTKLTVL |

Antibody Hegemark

| 3 | HCDR1 | SSYIN |
| 11 | HCDR2 | TINAVSGSTSYAQKFQG |
| 5 | HCDR3 | GGWFDY |
| 22 | LCDR1 | TGTSSDVGSKNYVN |
| 41 | LCDR2 | GVSKRHS |
| 14 | LCDR3 | GTFAGGKYYGV |
| 37 | VH | QVQLVQSGAEVKKPGSSVKVSCKASGYKFTSSYINWVRQAPGQGLEW MGTINAVSGSTSYAQKFQGRVTITADTSTSTAYMELSSLRSEDTAVY YCARGGWFDYWGQGTLVTVSS |
| 42 | VL | QSALTQPRSVSGSPGQSVTISCTGTSSDVGSKNYVNWYQQHPGKAPK LMIYGVSKRHSGVPDRFSGSKSGNTASLTISGLQAEDEADYYCGTFA GGKYYGVFGGGTKLTVL |

Example 7.2: Affinity to ActRIIA and ActRIIB

In preliminary experiments the affinity for ActRIIA was measured for selected antibodies. Results are shown in the following Table.

TABLE 13A

| | | Affinity KD [pM] | | | | | |
|---|---|---|---|---|---|---|---|
| | | Bimagrumab | Ofaschlupfer | Schwardamaga | Soidawüsrstel | Bebballesgmias | Bäradreck |
| ActRIIA | Fab | 1766 | 36.93 | 92.51 | 43.09 | 284.7 | 655.1 |
| | IgG | 236.9 | 38.87 | 60.98 | 34.52 | 142 | 111.9 |
| ActRIIB | Fab | 22.2 | 25.29 | 72.6 | 19.71 | 25.1 | 56.26 |
| | IgG | 6.196 | 27.68 | 29.31 | 50.85 | 16.67 | 63.77 |

In a more detailed study, the affinity for ActRIIA was measured for selected antibodies. Results are shown in the following Table (mean data from at least two independent experiments).

TABLE 13B

| | | Affinity KD [pM] | | | | | |
|---|---|---|---|---|---|---|---|
| | | Bimagrumab | Ofaschlupfer | Schwardamaga | Soidawüsrstel | Bebballesgmias | Bäradreck |
| ActRIIA | Fab | 262.2 | 20.68 | 61.21 | 43.09 | 284.7 | 655.1 |
| | IgG | 217.7 | 17.6 | 40.4 | 34.2 | 142 | 111.9 |
| ActRIIB | Fab | 3.3 | 3.3 | 13.8 | 2.6 | 2.6 | 1.4 |
| | IgG | 1.8 | 2.9 | 12.9 | 5.5 | 16.67 | 63.77 |

The experiment was repeated, in order to evaluate if the constant region of the antibodies has an influence on antibody affinity. Results are shown in Table 14 (mean data from at least two independent experiments).

TABLE 14A (values in pM):

| Antigen | Antibody format | Bimagrumab | Ofaschlupfer | Schwardamaga | Soidawürstle |
|---|---|---|---|---|---|
| Human ActRIIB | Human IgG1-PALALA-YTE | 2 | 3 | 13 | 5 |
| | Human IgG1-PALALA | 2 | 3 | 11 | 6 |
| | Mouse IgG2a-PALALA | 5 | 4 | 16 | 3 |
| | Fab | 2 | 2 | 10 | 11 |
| Human ActRIIA | Human IgG1-PALALA-YTE | 218 | 18 | 40 | 34 |
| | Human IgG1-PALALA | 197 | 20 | 36 | 25 |
| | Mouse IgG2a-PALALA | 134 | 20 | 39 | 27 |
| | Fab | 274 | 17 | 61 | 31 |
| Pig ActRIIA | Fab | 188 | 10 | 29 | 22 |
| Dog ActRIIA | Fab | 354 | 17 | 44 | 28 |
| Mouse ActRIIA | Fab | 239 | 18 | 39 | 40 |

It could be observed that the affinities of the antibodies of the present disclosure is completely independent of the antibody format used.

In a similar experiment the affinities of selected antibodies to ActRIIA and ActRIIB was measured. Results are shown in Table 14B (mean data from at least two independent experiments).

TABLE 14B

| Antibody | KD for ActRIIA [pM] | KD for ActRIIB [pM] |
|---|---|---|
| Mauldascha | 296 | 13 |
| Metzelsupp | 14 | 41 |
| Nonnafürzla | 52 | 8 |
| Ofaschlupfer | 17.6 | 2.9 |
| Oierspätzla | 45 | 57 |
| Rauchfloisch | 113 | 31 |
| Schwardamaga | 40.4 | 12.9 |
| Soidawürstle | 34.2 | 5.5 |
| Zibebe | 20 | 58 |
| Schnitzbrot | 89 | 40 |
| Wiebela | 54 | 36 |
| Krapfa | 4.7 | 591 |
| Seela | 156.7 | 11 |
| Peitscheschdegga | 334.5 | 35 |
| Hegemark | 86.9 | 43 |

Example 7.3: Reduced Unspecific Binding

Figure 6:
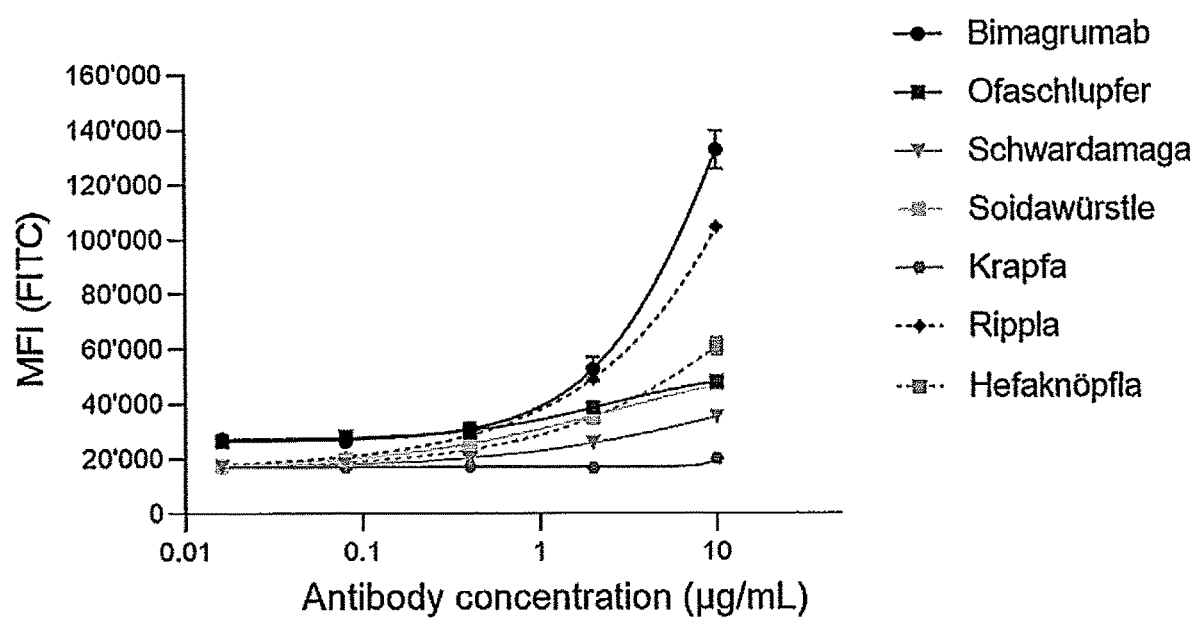
FIG. 6 shows that certain derivatives of bimagrumab show a reduced unspecific binding.

Selected antibodies were tested for unspecific binding on HEK cells (see Example 2.7). Results are shown in FIG. 6. As can be seen unspecific binding is improved for essentially all antibodies tested in this experiment. The least unspecific binding was observed for antibodies Schwardamaga and Krapfa.

Example 7.4: Improved HIC Score

Figure 7:
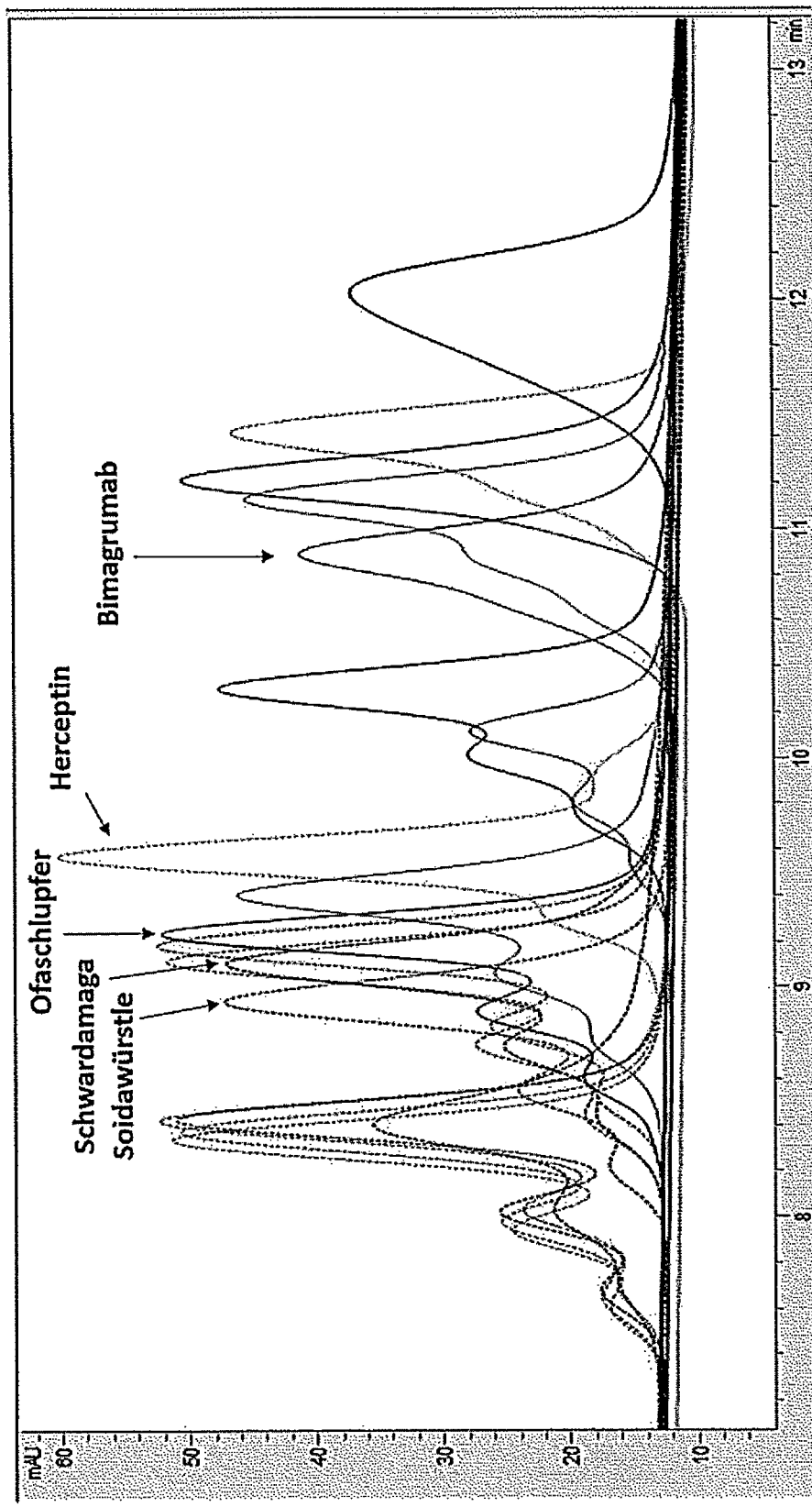
FIG. 7 shows that certain derivatives of bimagrumab have an improved HIC score.

Selected antibodies were also tested for their HIC score (see Example 2.2). The hydrophobicity increases with the retention time. Results are shown in FIG. 7. It can be seen that almost all antibodies tested had an improved HIC score compared to bimagrumab, including antibodies Ofaschlupfer, Schwardamaga and Soidawürstle.

Example 7.5: Reduced Charged Based Interactions

Figure 8:
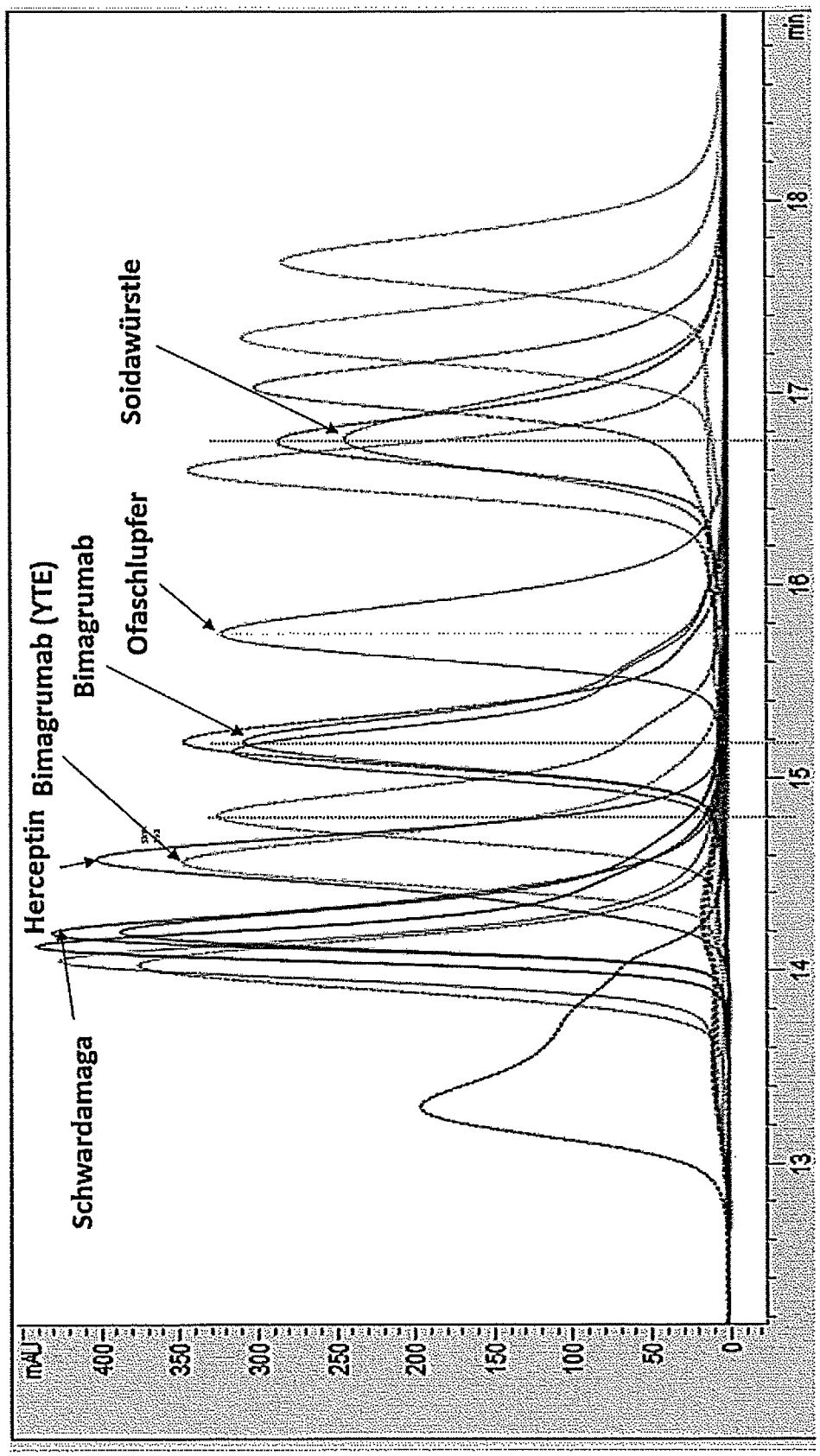
FIG. 8 shows that certain derivatives of bimagrumab have an improved Heparin score.

Selected antibodies were also tested for their charged based interactions by heparin chromatography. Results are shown in FIG. 8. Earlier elution time correlates with lower charged based interactions. It can be seen that many antibodies tested had an improved Heparin score compared to bimagrumab, including antibodies Bäradreck, Mauldascha, Metzelsupp, Nonnafürzla, Oierspätzla, Rauchfloisch and Schwardamaga.

Example 7.6: Improved Myostatin Inhibition
(SMAD RGA Assay)

Results of the measurement of myostatin inhibition are shown in Table 15. Several binders had an IC50 better than that of bimagrumab (mean data from three independent experiments).

TABLE 15

| | IC50 (nM) | fold difference to bimagrumab | IC90 (nM) | fold difference to bimagrumab | IC95 (nM) | fold difference to bimagrumab | IC99 (nM) | fold difference to bimagrumab |
|---|---|---|---|---|---|---|---|---|
| Bimagrumab (n = 5) | 0.56 | 1 | 13.47 | 1 | 55.16 | 1 | 2677.28 | 1 |
| Ofaschlupfer (n = 3) | 0.70 | 0.8 | 14.42 | 0.9 | 55.25 | 1.0 | 1242.67 | 2.2 |
| Schwardamaga (n = 3) | 0.75 | 0.7 | 14.67 | 0.9 | 41.55 | 1.3 | 425.37 | 6.3 |
| Soidawürstle (n = 3) | 0.13 | 4.3 | 6.63 | 2.0 | 34.99 | 1.6 | 2000.40 | 1.3 |

Shown in Table 16B below are the results for additional selected binders in the Myostation SMAD RGA assays.

Example 7.7: Improved Activin Inhibition (SMAD RGA Assay)

Results of preliminary experiments of the measurement of activin inhibition are shown in the following Table. Several binders had an IC50 better than that of bimagrumab.

TABLE 16A

| | IC90 (nM) | fold difference to bimagrumab | IC95 (nM) | fold difference to bimagrumab | IC99 (nM) | fold difference to bimagrumab |
|---|---|---|---|---|---|---|
| Bimagrumab (n = 2) | 9.38 | 1.0 | 37.87 | 1.0 | 829.15 | 1.0 |
| Ofaschlupfer | 2.27 | 4.1 | 4.97 | 7.6 | 28.05 | 29.6 |
| Schwardamaga | 5.34 | 1.8 | 14.23 | 2.7 | 123.8 | 6.7 |
| Soidawürstle | 2.16 | 4.3 | 8.86 | 4.3 | 200.5 | 4.1 |

Results of a more detailed study of the measurement of activin inhibition are shown in the following Table. Several binders had an IC90, IC95 and I099 better than that of bimagrumab (mean data from six independent experiments).

TABLE 16B

| | IC50 (nM) | fold difference to bimagrumab | IC90 (nM) | fold difference to bimagrumab | IC95 (nM) | fold difference to bimagrumab | IC99 (nM) | fold difference to bimagrumab |
|---|---|---|---|---|---|---|---|---|
| Bimagrumab (n = 8) | 0.32 | 1 | 6.20 | 1 | 19.55 | 1 | 206.30 | 1 |
| Ofaschlupfer (n = 6) | 0.32 | 1.0 | 3.02 | 2.1 | 7.07 | 21.8 | 47.76 | 147.2 |
| Schwardamaga (n = 6) | 0.46 | 0.7 | 5.09 | 0.8 | 12.76 | 39.3 | 99.03 | 305.1 |
| Soidawürstle (n = 6) | 0.16 | 2.0 | 1.81 | 0.3 | 4.84 | 14.9 | 19.31 | 59.5 |

Shown in Table 16C are the results for additional selected binders in Activin SMAD RGA and Myostation SMAD RGA assays.

Example 7.8: Reduced Viscosity

Binders were also rheological characterized using an Anton Paar AMCR102 cone and plate rheometer (CP20-0.5). Shear rate ramping at 20° C. was conducted to define a shear rate with Newtonian behaviour for the subsequent viscosity measurements. The shear rate ramping was carried out from 100 to 10000 1/s, and the shear rate of 4000 1/s with Newtonian flow was selected for sample analysis.

The viscosity was then measured in duplicate at 20° C. and single measurements at 5° C. at the defined shear rate. The RSD between the duplicate measurements was <2% for all candidate molecules. The measured variants were formulated in 20 mM L-Histidine, 160 mM Sucrose, 0.02% (v/v) PS80 at a sample concentration of 180 mg/mL. Tested was antibody bimagrumab (containing a LALA Fc modifi-

TABLE 16C

| | Activin SMAD RGA (nM) | | | Myostatin SMAD RGA (nM) | | |
|---|---|---|---|---|---|---|
| Antibody | IC50 (nM) | IC90 (nM) | nb of expts | IC50 (nM) | IC90 (nM) | # of expts |
| Bimagrumab | 0.3200 | 6.2000 | n = 8 | 0.2920 | 13.4700 | n = 5 |
| Mauldascha | 1.8270 | 6.7200 | n = 2 | 1.4245 | 13.3700 | n = 2 |
| Metzelsupp | 0.5734 | 3.7935 | n = 2 | 0.7130 | 7.7240 | n = 2 |
| Nonnafürzla | 0.5047 | 3.8145 | n = 2 | 1.3242 | 27.2850 | n = 2 |
| Ofaschlupfer | 0.3200 | 3.0200 | n = 7 | 0.7000 | 14.4200 | n = 4 |
| Oierspätzla | 0.3611 | 3.0570 | n = 2 | 0.9602 | 16.8395 | n = 2 |
| Rauchfloisch | 0.6685 | 5.1105 | n = 2 | 1.3135 | 18.2135 | n = 2 |
| Schwardamaga | 0.4600 | 5.0900 | n = 7 | 0.7500 | 14.6700 | n = 4 |
| Soidawürstle | 0.1600 | 1.8100 | n = 7 | 0.1300 | 6.6300 | n = 4 |
| Zibebe | 0.5425 | 7.8335 | n = 2 | 1.4599 | 19.0300 | n = 2 |
| Schnitzbrot | 0.3124 | 2.5235 | n = 2 | 0.6239 | 19.1190 | n = 2 |
| Wiebela | 0.2534 | 3.9600 | n = 2 | 0.2497 | 14.8355 | n = 2 |
| Krapfa | unstable | unstable | n = 1 | 0.0497 | 10410.0 | n = 1 |
| Seela | 0.3379 | 4.7420 | n = 1 | 0.4732 | 18.1700 | n = 1 |
| Peitscheschdegga | 0.2986 | 4.9180 | n = 1 | 2.8390 | 48.4200 | n = 1 |
| Hegemark | 0.3045 | 4.3660 | n = 1 | 0.5162 | 23.4500 | n = 1 | cation), as well as antibody Ofaschlupfer (with a wild-type Fc region and a Fc region containing a PA-LALA modification). Results are shown in Table 17 and in FIG. 11.

TABLE 17

| Binder | Fc | Viscosity at 5° C. (cP) | Viscosity at 20° C. (cp) |
| --- | --- | --- | --- |
| Bimagrumab | LALA | 29 | 15 |
| Ofaschlupfer | Wild type | 22 | 11 |
| Ofaschlupfer | PA-LALA | 21 | 12 |

The measured viscosity of Ofaschlupfer is lower at both 5° C. and 20° C., compared to bimagrumab, irrespective of the Fc part of the binders. The lower viscosity values of Ofaschlupfer is attributed to improved physiochemical properties of the molecules, such as reduced surface hydrophobicity.

Example 8: In Vivo Efficacy Study

Male BALB SCID mice at 7-8 weeks old (Jackson labs, stock 001803), were randomized into treatment groups by body weight prior to starting the experiments. Mice were given once-weekly intravenous administration with isotype control, bimagrumab (containing a LALA Fc modification), or antibodies Ofaschlupfer, Schwardamaga or Soidawürstle (all containing a PA-LALA Fc modification), for 4 weeks. Bodyweight was monitored at least twice per week throughout treatment. After 4 weeks, mice were euthanised via $CO_2$ inhalation, followed by necropsy and skeletal muscle tissue collection.

Figure 12:
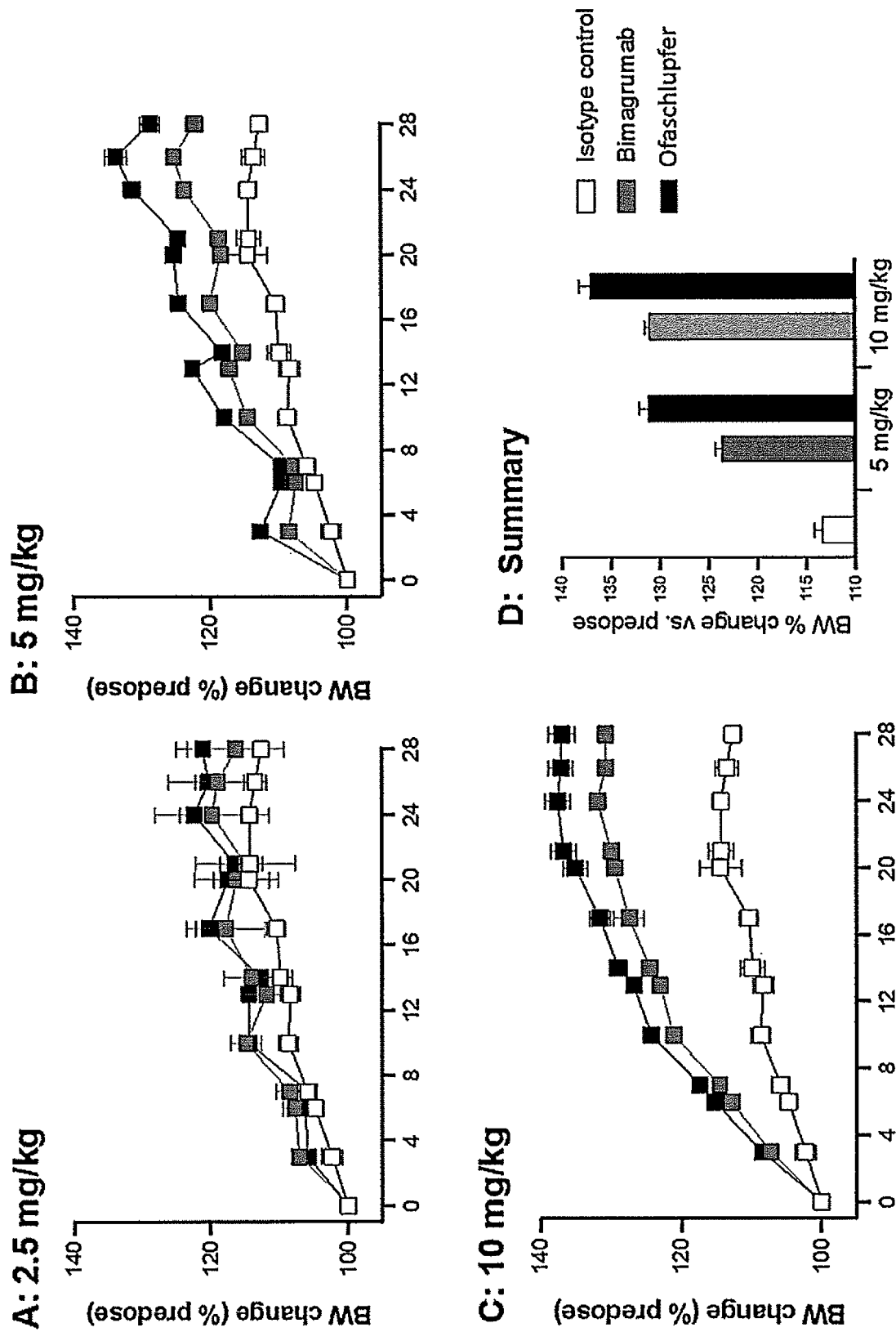
FIG. 12, views A, B, C and D, show the effect on body weight (BW) in naïve SCID mice, following weekly intravenous administration with isotype control, bimagrumab, or Ofaschlupfer, at dose levels of 2.5 mg/kg (A), 5 mg/kg (B) and 10 mg/kg (C). Data are the mean % change in BW relative to predose (+/−SEM, n=6). A bar graph summary of bodyweight changes in week 4 (day 24-28) are presented in (D).
Figure 13:
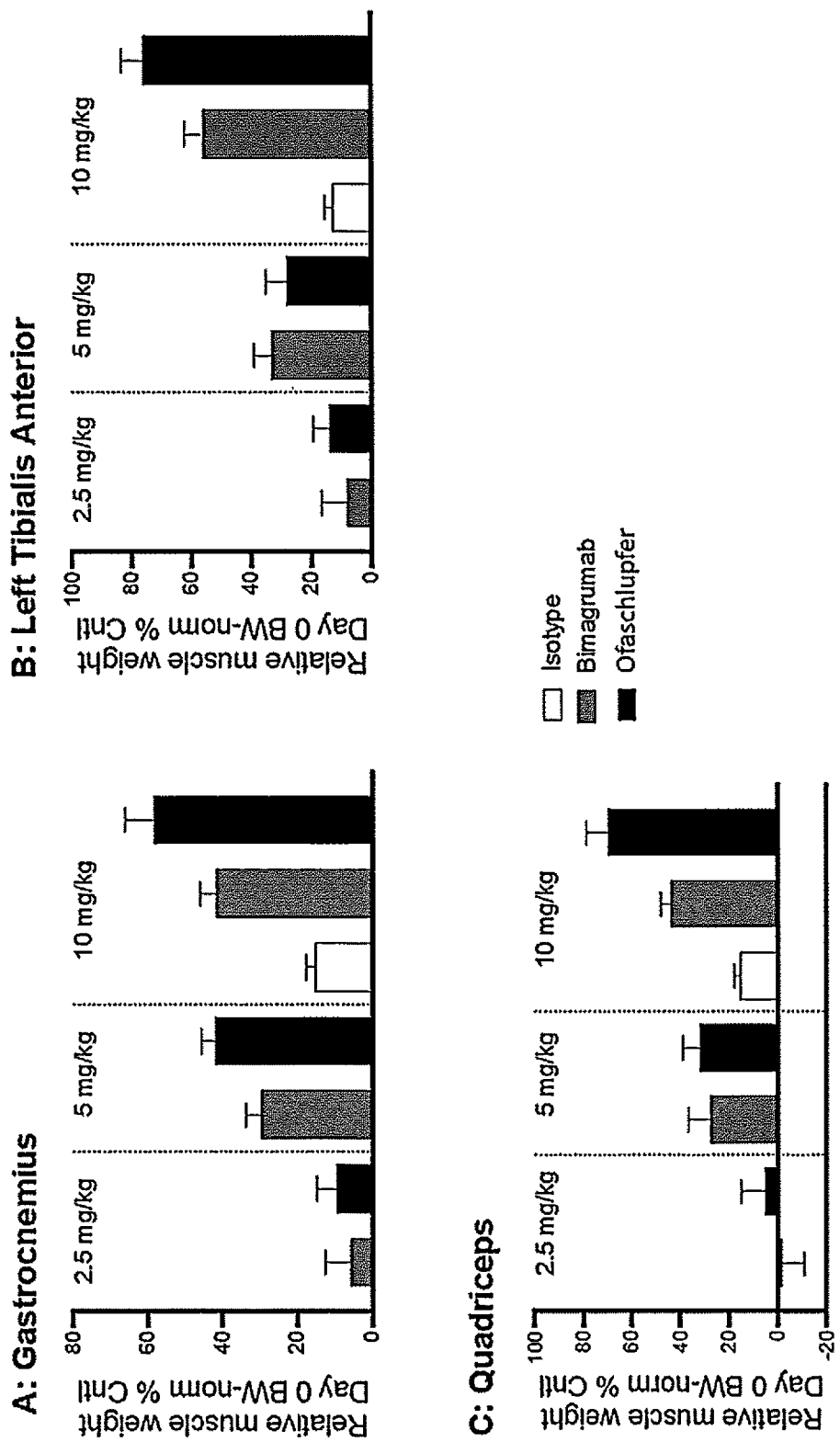
FIG. 13, views A, B and C, show the effect on muscle weight in naïve SCID mice, following weekly intravenous administration with isotype control, bimagrumab or Ofaschlupfer, at dose levels of 2.5 mg/kg (A), 5 mg/kg (B) and 10 mg/kg (C). Data are the mean BW-normalised muscle weight, expressed as % vs. isotype control group (+/−SEM, n=6-10).
Figure 14:
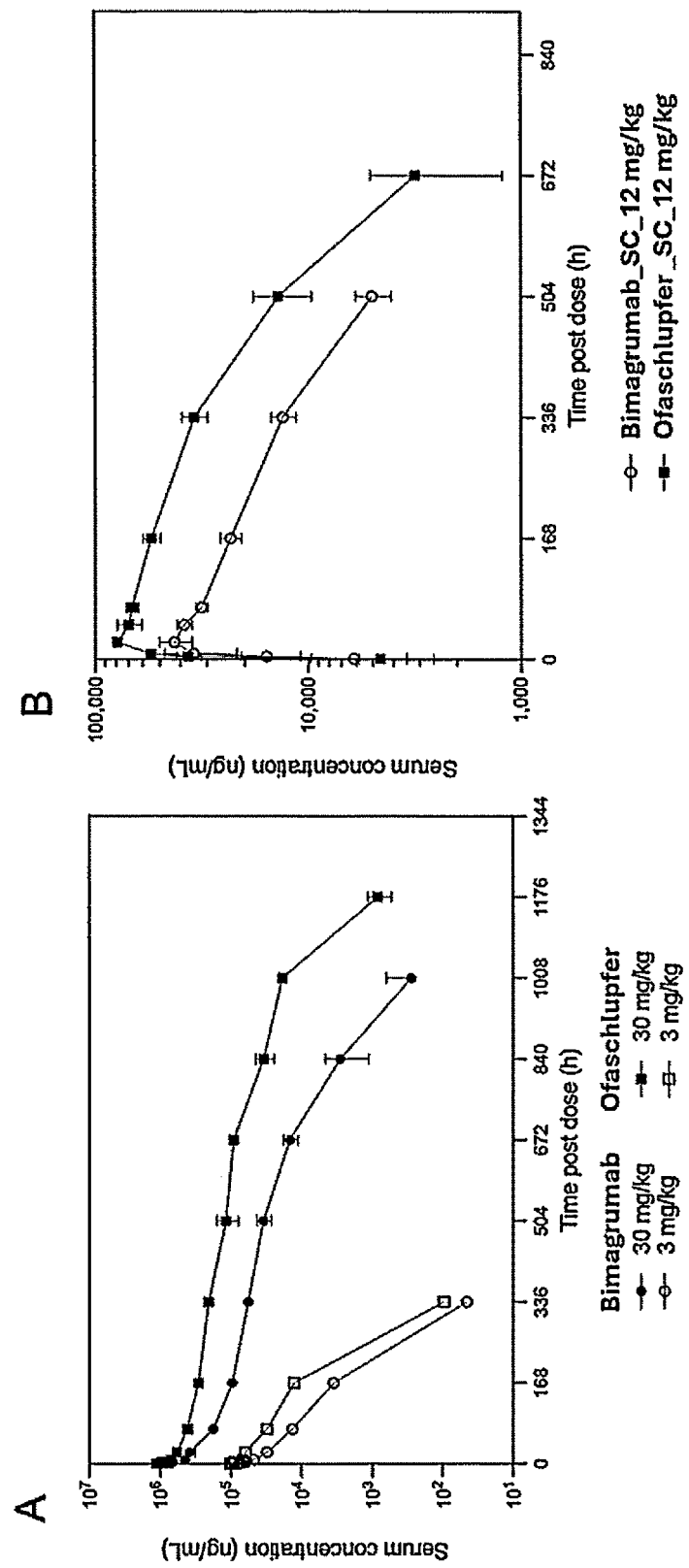
FIG. 14, views A and B, show serum concentration vs. time of Ofaschlupfer and bimagrumab in male cynomolgus monkey (A) and male minipig (B) following single intravenous (IV) or subcutanoues (SC) administration. Data are the mean+/−range of two animals per group.

Exemplary results for antibody Ofaschlupfer are shown in FIGS. 12 and 13 (essentially identical results were obtained with antibodies Schwardamaga and Soidawürstle). The results show that bimagrumab and Ofaschlupfer administration promoted an increase in body weight (FIG. 12) and skeletal muscle hypertrophy of all examined muscles (FIG. 13) in a dose-dependent manner, with BW increase and muscle hypertrophy most apparent at 5 and 10 mg/kg (FIGS. 12B and 12C; FIG. 13). The results also show that Ofaschlupfer elicits a considerably higher effect on body weight increase and muscle hypertrophy than bimagrumab at 5 and 10 mg/kg. Indeed, the bodyweight effect of Ofaschlupfer at 5 mg/kg is greater than bimagrumab at 5 mg/kg, and similar to bimagrumab at 10 mg/kg (FIG. 12D), which suggests that Ofaschlupfer elicits a 2-fold greater effect than bimagrumab (depending on dose/exposure).

Example 9: Pharmacokinetics in Cynomolgus Monkey and Minipig

Bimagrumab (in PA-LALA format) and antibody Ofaschlupfer were evaluated for their pharmacokinetic (PK) profile in cynomolgus monkey. Following single IV administration at 30 mg/kg, the PK profile of Ofaschlupfer displays higher exposures over a longer duration than bimagrumab (FIG. 16A). Indeed, Ofaschlupfer exhibits approximately 3-fold higher exposures (AUC0-inf) and 3-fold lower linear CL than bimagrumab at the same dose (Table 18).

Bimagrumab and Ofaschlupfer were also evaluated in minipig for their PK properties following IV and SC dosing. Serum concentrations of Ofaschlupfer were again significantly higher than bimagrumab and more persistent, following single SC administration at 12 mg/kg (FIG. 16B), with overall exposure (AUC0-inf) of Ofaschlupfer being more than 2-fold higher. The SC bioavailability (F) in minipig was calculated to be approximately 93% for Ofaschlupfer and 45% for bimagrumab. Interestingly, the observed F of bimagrumab in minipig is very well predictive for the reported F in human (mean popPK 41%; Clin Pharmacokinet (2023) 62(1):141-55). This gives high confidence about the predictability of Ofaschlupfer SC bioavailability in human. Overall, these results demonstrate that Ofaschlupfer has a much more favourable PK and SC absorption profile than bimagrumab.

TABLE 18

Data are the mean of two animals per group. Bioavailability (% F) was calculated as the dose-normalised AUC0-inf (SC)/dose-normalised AUC0-inf (IV).

| | Cynomolgus | | | Minipig | | | |
| --- | --- | --- | --- | --- | --- | --- | --- |
| | Dose (mg/kg) | $AUC_{0-inf}$ (h * ng/mL) | CL (mL/h/kg) | Dose (mg/kg) | $AUC_{0-inf}$ IV (h * ng/mL) | $AUC_{0-inf}$ SC (h * ng/mL) | Bioavailability, SC (% F) |
| Ofaschlupfer | 30 (IV) | 179000000 | 0.168 | 12 | 25900000 | 24100000 | 93 |
| Bimagrumab | | 64300000 | 0.467 | (IV & SC) | 24200000 | 10900000 | 45 |

The invention claimed is:

1. An antibody or antigen binding fragment thereof which binds to Activin receptor II A (ActRIIA) and/or Activin receptor II B (ActRIIB) comprising:
   a) a heavy chain variable region CDR1 comprising the amino acid sequence of SEQ ID NO: 3;
   b) a heavy chain variable region CDR2 comprising the amino acid sequence of SEQ ID NO: 11;
   c) a heavy chain variable region CDR3 comprising the amino acid sequence of SEQ ID NO: 5;
   d) a light chain variable region CDR1 comprising the amino acid sequence of SEQ ID NO: 22;
   e) a light chain variable region CDR2 comprising the amino acid sequence of SEQ ID NO: 13 and
   f) a light chain variable region CDR3 comprising the amino acid sequence of SEQ ID NO: 14.

2. The antibody or antigen binding fragment thereof of claim 1 comprising:
   a) the heavy chain variable region CDR1 consisting of the amino acid sequence of SEQ ID NO: 3;
   b) the heavy chain variable region CDR2 consisting of the amino acid sequence of SEQ ID NO: 11;
   c) the heavy chain variable region CDR3 consisting of the amino acid sequence of SEQ ID NO: 5;
   d) the light chain variable region CDR1 consisting of the amino acid sequence of SEQ ID NO: 22;
   e) the light chain variable region CDR2 consisting of the amino acid sequence of SEQ ID NO: 13; and
   f) the light chain variable region CDR3 consisting of the amino acid sequence of SEQ ID NO: 14.

3. The antibody or antigen binding fragment of claim 1 further comprising an Fc region, wherein the Fc region comprises a YTE (M252Y/S254T/T256E) mutation, wherein numbering is according to EU index of Kabat.

4. The antibody or antigen binding fragment of claim 1 further comprising an Fc region, wherein the Fc region comprises a silencing modification, wherein the silencing modification is a PA-LALA(L234A/L235A/P329A), PG-LALA(L234A/L235A/P329G), or AEASS (L234A/L235E/G237A/A330S/P331S) mutation, wherein numbering is according to EU index of Kabat.

5. The antibody or antigen binding fragment of claim 1, wherein said antibody or antigen binding fragment binds to ActRIIA and ActRIIB.

6. An antibody or antigen binding fragment thereof comprising an Fc region, a heavy chain variable region having the amino acid sequence of SEQ ID NO: 16, and a light chain variable region having the amino acid sequence of SEQ ID No: 23.

7. The antibody or antigen binding fragment thereof of claim 6, wherein the Fc region comprises a YTE (M252Y/S254T/T256E) mutation, wherein numbering is according to EU index of Kabat.

8. The antibody or antigen binding fragment thereof of claim 6, wherein the Fc region comprises a silencing modification, wherein the silencing modification is a PA-LALA (L234A/L235A/P329A), PG-LALA(L234A/L235A/P329G), or AEASS (L234A/L235E/G237A/A330S/P331S) mutation, wherein numbering is according to EU index of Kabat.

9. The antibody or antigen binding fragment of claim 6, wherein said antibody or antigen binding fragment binds to ActRIIA and ActRIIB.

10. An antibody or antigen binding fragment thereof comprising an Fc region and:
    a) a heavy chain variable region CDR1 comprising the amino acid sequence of SEQ ID NO: 3;
    b) a heavy chain variable region CDR2 comprising the amino acid sequence of SEQ ID NO: 11;
    c) a heavy chain variable region CDR3 comprising the amino acid sequence of SEQ ID NO: 5;
    d) a light chain variable region CDR1 comprising the amino acid sequence of SEQ ID NO: 22;
    e) a light chain variable region CDR2 comprising the amino acid sequence of SEQ ID NO: 13 and
    f) a light chain variable region CDR3 comprising the amino acid sequence of SEQ ID NO: 14.

11. The antibody or antigen binding fragment thereof of claim 10 comprising:
    a) the heavy chain variable region CDR1 consisting of the amino acid sequence of SEQ ID NO: 3;
    b) the heavy chain variable region CDR2 consisting of the amino acid sequence of SEQ ID NO: 11;
    c) the heavy chain variable region CDR3 consisting of the amino acid sequence of SEQ ID NO: 5;
    d) the light chain variable region CDR1 consisting of the amino acid sequence of SEQ ID NO: 22;
    e) the light chain variable region CDR2 consisting of the amino acid sequence of SEQ ID NO: 13; and
    f) the light chain variable region CDR3 consisting of the amino acid sequence of SEQ ID NO: 14.

12. The antibody or antigen binding fragment of claim 10, wherein the Fc region comprises a YTE (M252Y/S254T/T256E) mutation, wherein numbering is according to EU index of Kabat.

13. The antibody or antigen binding fragment of claim 10, wherein the Fc region comprises a silencing modification, wherein the silencing modification is a PA-LALA(L234A/L235A/P329A), PG-LALA(L234A/L235A/P329G), or AEASS (L234A/L235E/G237A/A330S/P331S) mutation, wherein numbering is according to EU index of Kabat.

14. The antibody or antigen binding fragment of claim 10, wherein said antibody or antigen binding fragment binds to ActRIIA and ActRIIB.

\* \* \* \* \*